United States Patent
Brauker et al.

(10) Patent No.: US 7,881,763 B2
(45) Date of Patent: *Feb. 1, 2011

(54) OPTIMIZED SENSOR GEOMETRY FOR AN IMPLANTABLE GLUCOSE SENSOR

(75) Inventors: James H. Brauker, San Diego, CA (US); Victoria Carr-Brendel, Pleasanton, CA (US); Paul V. Neale, San Diego, CA (US); Laura A. Martinson, San Diego, CA (US); Mark A. Tapsak, Orangeville, PA (US)

(73) Assignee: DexCom, Inc., San Diego, CA (US)

( * ) Notice: Subject to any disclaimer, the term of this patent is extended or adjusted under 35 U.S.C. 154(b) by 1172 days.

This patent is subject to a terminal disclaimer.

(21) Appl. No.: 11/415,631

(22) Filed: May 2, 2006

(65) Prior Publication Data
US 2006/0211921 A1 Sep. 21, 2006

Related U.S. Application Data

(62) Division of application No. 10/646,333, filed on Aug. 22, 2003, now Pat. No. 7,134,999.

(60) Provisional application No. 60/460,825, filed on Apr. 4, 2003.

(51) Int. Cl.
*A61B 5/1473* (2006.01)

(52) U.S. Cl. .................................. 600/345; 600/347
(58) Field of Classification Search ............... 600/309, 600/300, 316, 322, 345, 347, 365
See application file for complete search history.

(56) References Cited

U.S. PATENT DOCUMENTS 3,381,371 A 5/1968 Russell (Continued)

FOREIGN PATENT DOCUMENTS

EP 0 098 592 1/1984

(Continued)

OTHER PUBLICATIONS

Atanasov et al. Biosensor for Continuous Glucose Monitoring. Biotechnology and Bioengineering 1994, 43, 262-266.

(Continued)

*Primary Examiner*—Eric F Winakur
(74) *Attorney, Agent, or Firm*—Knobbe Martens Olson & Bear LLP

(57) ABSTRACT

An implantable sensor for use in measuring a concentration of an analyte such as glucose in a bodily fluid, including a body with a sensing region adapted for transport of analytes between the sensor and the bodily fluid, wherein the sensing region is located on a curved portion of the body such that when a foreign body capsule forms around the sensor, a contractile force is exerted by the foreign body capsule toward the sensing region. The body is partially or entirely curved, partially or entirely covered with an anchoring material for supporting tissue ingrowth, and designed for subcutaneous tissue implantation. The geometric design, including curvature, shape, and other factors minimize chronic inflammatory response at the sensing region and contribute to improved performance of the sensor in vivo.

44 Claims, 17 Drawing Sheets

U.S. PATENT DOCUMENTS

| | | |
|---|---|---|
| 3,775,182 A | 11/1973 | Patton et al. |
| 3,791,871 A | 2/1974 | Rowley |
| 3,838,033 A | 9/1974 | Mindt et al. |
| 3,898,984 A | 8/1975 | Mandel et al. |
| 3,929,971 A | 12/1975 | Roy |
| 3,943,918 A | 3/1976 | Lewis |
| 3,966,580 A | 6/1976 | Janata et al. |
| 3,979,274 A | 9/1976 | Newman |
| 4,040,908 A | 8/1977 | Clark, Jr. |
| 4,073,713 A | 2/1978 | Newman |
| 4,076,656 A | 2/1978 | White et al. |
| 4,172,770 A | 10/1979 | Semersky et al. |
| 4,197,840 A | 4/1980 | Beck et al. |
| 4,225,410 A | 9/1980 | Pace |
| 4,240,889 A | 12/1980 | Yoda et al. |
| 4,253,469 A | 3/1981 | Aslan |
| 4,255,500 A | 3/1981 | Hooke |
| 4,260,725 A | 4/1981 | Keogh et al. |
| 4,324,257 A | 4/1982 | Albarda et al. |
| 4,353,368 A | 10/1982 | Slovak et al. |
| 4,353,888 A | 10/1982 | Sefton |
| 4,374,013 A | 2/1983 | Enfors |
| 4,388,166 A | 6/1983 | Suzuki et al. |
| 4,403,984 A | 9/1983 | Ash et al. |
| 4,415,666 A | 11/1983 | D'Orazio et al. |
| 4,418,148 A | 11/1983 | Oberhardt |
| 4,431,004 A | 2/1984 | Bessman et al. |
| 4,431,507 A | 2/1984 | Nankai et al. |
| 4,436,094 A | 3/1984 | Cerami |
| 4,442,841 A | 4/1984 | Uehara et al. |
| 4,477,314 A | 10/1984 | Richter et al. |
| 4,484,987 A | 11/1984 | Gough |
| 4,494,950 A | 1/1985 | Fischell |
| 4,506,680 A | 3/1985 | Stokes |
| RE31,916 E | 6/1985 | Oswin et al. |
| 4,534,355 A | 8/1985 | Potter |
| 4,554,927 A | 11/1985 | Fussell |
| 4,571,292 A | 2/1986 | Liu et al. |
| 4,577,642 A | 3/1986 | Stokes |
| 4,603,152 A | 7/1986 | Laurin et al. |
| 4,650,547 A | 3/1987 | Gough |
| 4,655,880 A | 4/1987 | Liu |
| 4,671,288 A | 6/1987 | Gough |
| 4,680,268 A | 7/1987 | Clark, Jr. |
| 4,686,044 A | 8/1987 | Behnke et al. |
| 4,689,309 A | 8/1987 | Jones |
| 4,702,732 A | 10/1987 | Powers et al. |
| 4,703,756 A | 11/1987 | Gough et al. |
| 4,711,251 A | 12/1987 | Stokes |
| 4,721,677 A | 1/1988 | Clark, Jr. |
| 4,731,726 A | 3/1988 | Allen |
| 4,750,496 A | 6/1988 | Reinhart et al. |
| 4,753,652 A | 6/1988 | Langer et al. |
| 4,757,022 A | 7/1988 | Shults et al. |
| 4,759,828 A | 7/1988 | Young et al. |
| 4,776,944 A | 10/1988 | Janata et al. |
| 4,781,798 A | 11/1988 | Gough |
| 4,795,542 A | 1/1989 | Ross et al. |
| 4,803,243 A | 2/1989 | Fujimoto et al. |
| 4,805,624 A | 2/1989 | Yao et al. |
| 4,805,625 A | 2/1989 | Wyler |
| 4,810,470 A | 3/1989 | Burkhardt et al. |
| 4,852,573 A | 8/1989 | Kennedy |
| 4,861,830 A | 8/1989 | Ward, Jr. |
| 4,871,440 A | 10/1989 | Nagata et al. |
| 4,883,057 A | 11/1989 | Broderick |
| 4,889,744 A | 12/1989 | Quaid |
| 4,890,620 A | 1/1990 | Gough |
| 4,890,621 A | 1/1990 | Hakky |
| 4,919,141 A | 4/1990 | Zier et al. |
| 4,927,407 A | 5/1990 | Dorman |
| 4,935,345 A | 6/1990 | Guilbeau et al. |
| 4,953,552 A | 9/1990 | DeMarzo |
| 4,963,595 A | 10/1990 | Ward et al. |
| 4,970,145 A | 11/1990 | Bennetto et al. |
| 4,974,929 A | 12/1990 | Curry |
| 4,984,929 A | 1/1991 | Rock et al. |
| 4,986,271 A | 1/1991 | Wilkins |
| 4,986,671 A | 1/1991 | Sun et al. |
| 4,988,341 A | 1/1991 | Columbus et al. |
| 4,992,794 A | 2/1991 | Brouwers |
| 4,994,167 A | 2/1991 | Shults et al. |
| 5,002,572 A | 3/1991 | Picha |
| 5,007,929 A | 4/1991 | Quaid |
| 5,019,096 A | 5/1991 | Fox, Jr. et al. |
| 5,034,112 A | 7/1991 | Murase et al. |
| 5,050,612 A | 9/1991 | Matsumura |
| 5,059,654 A | 10/1991 | Hou et al. |
| 5,089,112 A | 2/1992 | Skotheim et al. |
| 5,101,814 A | 4/1992 | Palti |
| 5,108,819 A | 4/1992 | Heller et al. |
| 5,113,871 A | 5/1992 | Viljanto et al. |
| 5,130,231 A | 7/1992 | Kennedy et al. |
| 5,137,028 A | 8/1992 | Nishimura |
| 5,160,418 A | 11/1992 | Mullen |
| 5,165,407 A | 11/1992 | Wilson et al. |
| 5,171,689 A | 12/1992 | Kawaguri et al. |
| 5,190,041 A | 3/1993 | Palti |
| 5,202,261 A | 4/1993 | Musho et al. |
| 5,222,980 A | 6/1993 | Gealow |
| 5,235,003 A | 8/1993 | Ward et al. |
| 5,249,576 A | 10/1993 | Goldberger et al. |
| 5,264,104 A | 11/1993 | Gregg et al. |
| 5,269,891 A | 12/1993 | Colin |
| 5,271,736 A | 12/1993 | Picha |
| 5,282,848 A | 2/1994 | Schmitt |
| 5,298,144 A | 3/1994 | Spokane |
| 5,299,571 A | 4/1994 | Mastrototaro |
| 5,310,469 A | 5/1994 | Cunningham et al. |
| 5,314,471 A | 5/1994 | Brauker et al. |
| 5,316,008 A | 5/1994 | Suga et al. |
| 5,322,063 A | 6/1994 | Allen et al. |
| 5,324,322 A | 6/1994 | Grill et al. |
| 5,326,356 A | 7/1994 | Della Valle et al. |
| 5,328,451 A | 7/1994 | Davis et al. |
| 5,331,555 A | 7/1994 | Hashimoto et al. |
| 5,337,747 A | 8/1994 | Neftel |
| 5,340,352 A | 8/1994 | Nakanishi et al. |
| 5,344,454 A | 9/1994 | Clarke et al. |
| 5,348,788 A | 9/1994 | White |
| 5,352,351 A | 10/1994 | White |
| 5,356,786 A | 10/1994 | Heller et al. |
| 5,368,028 A | 11/1994 | Palti |
| 5,372,133 A | 12/1994 | Hogen Esch |
| 5,380,536 A | 1/1995 | Hubbell et al. |
| 5,384,028 A | 1/1995 | Ito |
| 5,387,327 A | 2/1995 | Khan |
| 5,390,671 A | 2/1995 | Lord et al. |
| 5,391,250 A | 2/1995 | Cheney et al. |
| 5,397,848 A | 3/1995 | Yang et al. |
| 5,411,647 A | 5/1995 | Johnson et al. |
| 5,411,866 A | 5/1995 | Luong |
| 5,428,123 A | 6/1995 | Ward et al. |
| 5,429,735 A | 7/1995 | Johnson et al. |
| 5,431,160 A | 7/1995 | Wilkins |
| 5,453,278 A | 9/1995 | Chan et al. |
| 5,458,631 A | 10/1995 | Xavier et al. |
| 5,462,051 A | 10/1995 | Oka et al. |
| 5,462,064 A | 10/1995 | D'Angelo et al. |
| 5,462,645 A | 10/1995 | Albery et al. |
| 5,464,013 A | 11/1995 | Lemelson |
| 5,466,356 A | 11/1995 | Schneider et al. |
| 5,469,846 A | 11/1995 | Khan |
| 5,476,094 A | 12/1995 | Allen et al. |

| Patent | Date | Inventor |
|---|---|---|
| 5,480,711 A | 1/1996 | Ruefer |
| 5,482,008 A | 1/1996 | Stafford et al. |
| 5,494,562 A | 2/1996 | Maley et al. |
| 5,496,453 A | 3/1996 | Uenoyama et al. |
| 5,497,772 A | 3/1996 | Schulman et al. |
| 5,507,288 A | 4/1996 | Bocker et al. |
| 5,508,509 A | 4/1996 | Yafuso et al. |
| 5,513,636 A | 5/1996 | Palti |
| 5,518,601 A | 5/1996 | Foos et al. |
| 5,529,066 A | 6/1996 | Palti |
| 5,531,878 A | 7/1996 | Vadgama et al. |
| 5,540,828 A | 7/1996 | Yacynych |
| 5,545,220 A | 8/1996 | Andrews et al. |
| 5,545,223 A | 8/1996 | Neuenfeldt et al. |
| 5,549,675 A | 8/1996 | Neuenfeldt et al. |
| 5,564,439 A | 10/1996 | Picha |
| 5,568,806 A | 10/1996 | Cheney, II et al. |
| 5,569,186 A | 10/1996 | Lord et al. |
| 5,569,462 A | 10/1996 | Martinson et al. |
| 5,571,395 A | 11/1996 | Park et al. |
| 5,575,930 A | 11/1996 | Tietje-Girault et al. |
| 5,582,184 A | 12/1996 | Erickson et al. |
| 5,582,697 A | 12/1996 | Ikeda et al. |
| 5,584,813 A | 12/1996 | Livingston et al. |
| 5,584,876 A | 12/1996 | Bruchman et al. |
| 5,586,553 A | 12/1996 | Halili et al. |
| 5,589,133 A | 12/1996 | Suzuki |
| 5,589,563 A | 12/1996 | Ward et al. |
| 5,593,440 A | 1/1997 | Brauker et al. |
| 5,593,852 A | 1/1997 | Heller et al. |
| 5,607,565 A | 3/1997 | Azarnia et al. |
| 5,628,890 A | 5/1997 | Carter et al. |
| 5,640,954 A | 6/1997 | Pfeiffer |
| 5,653,756 A | 8/1997 | Clarke et al. |
| 5,653,863 A | 8/1997 | Genshaw et al. |
| 5,658,330 A | 8/1997 | Carlisle et al. |
| 5,683,562 A | 11/1997 | Schaffar et al. |
| 5,686,829 A | 11/1997 | Girault |
| 5,695,623 A | 12/1997 | Michel et al. |
| 5,704,354 A | 1/1998 | Preidel et al. |
| 5,706,807 A | 1/1998 | Picha |
| 5,711,861 A | 1/1998 | Ward et al. |
| 5,713,888 A | 2/1998 | Neuenfeldt et al. |
| 5,733,336 A | 3/1998 | Neuenfeldt et al. |
| 5,735,273 A | 4/1998 | Kurnik et al. |
| 5,741,330 A | 4/1998 | Brauker et al. |
| 5,743,262 A | 4/1998 | Lepper, Jr. et al. |
| 5,756,632 A | 5/1998 | Ward et al. |
| 5,776,324 A | 7/1998 | Usala |
| 5,777,060 A | 7/1998 | Van Antwerp |
| 5,782,912 A | 7/1998 | Brauker et al. |
| 5,783,054 A | 7/1998 | Raguse et al. |
| 5,787,900 A | 8/1998 | Butler et al. |
| 5,791,344 A | 8/1998 | Schulman et al. |
| 5,795,774 A | 8/1998 | Matsumoto et al. |
| 5,798,065 A | 8/1998 | Picha |
| 5,800,420 A | 9/1998 | Gross |
| 5,800,529 A | 9/1998 | Brauker et al. |
| 5,804,048 A | 9/1998 | Wong et al. |
| 5,807,375 A | 9/1998 | Gross et al. |
| 5,807,406 A | 9/1998 | Brauker et al. |
| 5,811,487 A | 9/1998 | Schulz, Jr. et al. |
| 5,820,622 A | 10/1998 | Gross et al. |
| 5,833,603 A | 11/1998 | Kovacs et al. |
| 5,837,728 A | 11/1998 | Purcell |
| 5,840,148 A | 11/1998 | Campbell et al. |
| 5,840,240 A | 11/1998 | Stenoien et al. |
| 5,861,019 A | 1/1999 | Sun et al. |
| 5,863,400 A | 1/1999 | Drummond et al. |
| 5,871,514 A | 2/1999 | Wiklund et al. |
| 5,882,494 A | 3/1999 | Van Antwerp |
| 5,895,235 A | 4/1999 | Droz |
| 5,897,578 A | 4/1999 | Wiklund et al. |
| 5,904,708 A | 5/1999 | Goedeke |
| 5,910,554 A | 6/1999 | Kempe et al. |
| 5,913,998 A | 6/1999 | Butler et al. |
| 5,914,026 A | 6/1999 | Blubaugh, Jr. et al. |
| 5,919,215 A | 7/1999 | Wiklund et al. |
| 5,931,814 A | 8/1999 | Alex et al. |
| 5,944,661 A | 8/1999 | Swette et al. |
| 5,957,854 A | 9/1999 | Besson et al. |
| 5,961,451 A | 10/1999 | Reber et al. |
| 5,963,132 A | 10/1999 | Yoakum |
| 5,964,261 A | 10/1999 | Neuenfeldt et al. |
| 5,964,804 A | 10/1999 | Brauker et al. |
| 5,964,993 A | 10/1999 | Blubaugh et al. |
| 5,965,380 A | 10/1999 | Heller et al. |
| 5,967,986 A | 10/1999 | Cimochowski et al. |
| 5,976,085 A | 11/1999 | Kimball et al. |
| 5,985,129 A | 11/1999 | Gough et al. |
| 5,989,409 A | 11/1999 | Kurnik et al. |
| 5,999,848 A | 12/1999 | Gord et al. |
| 6,001,067 A | 12/1999 | Shults et al. |
| 6,011,984 A | 1/2000 | Van Antwerp et al. |
| 6,013,113 A | 1/2000 | Mika |
| 6,016,448 A | 1/2000 | Busacker et al. |
| 6,049,727 A | 4/2000 | Crothall |
| 6,059,946 A | 5/2000 | Yukawa et al. |
| 6,063,637 A | 5/2000 | Arnold et al. |
| 6,066,083 A | 5/2000 | Slater et al. |
| 6,066,448 A | 5/2000 | Wohlstadter et al. |
| 6,074,775 A | 6/2000 | Gartstein et al. |
| 6,081,736 A | 6/2000 | Colvin et al. |
| 6,083,710 A | 7/2000 | Heller et al. |
| 6,088,608 A | 7/2000 | Schulman et al. |
| 6,091,975 A | 7/2000 | Daddona et al. |
| 6,093,172 A | 7/2000 | Funderburk et al. |
| 6,117,290 A | 9/2000 | Say |
| 6,119,028 A | 9/2000 | Schulman et al. |
| 6,122,536 A | 9/2000 | Sun et al. |
| 6,134,461 A | 10/2000 | Say et al. |
| 6,135,978 A | 10/2000 | Houben et al. |
| 6,144,869 A | 11/2000 | Berner et al. |
| 6,144,871 A | 11/2000 | Saito et al. |
| 6,162,611 A | 12/2000 | Heller et al. |
| 6,175,752 B1 | 1/2001 | Say et al. |
| 6,187,062 B1 | 2/2001 | Oweis et al. |
| 6,200,772 B1 | 3/2001 | Vadgama et al. |
| 6,201,980 B1 | 3/2001 | Darrow et al. |
| 6,208,894 B1 | 3/2001 | Schulman et al. |
| 6,212,416 B1 | 4/2001 | Ward et al. |
| 6,230,059 B1 | 5/2001 | Duffin |
| 6,231,879 B1 | 5/2001 | Li et al. |
| 6,233,471 B1 | 5/2001 | Berner et al. |
| 6,241,863 B1 | 6/2001 | Monbouquette |
| 6,248,067 B1 | 6/2001 | Causey, III et al. |
| 6,256,522 B1 | 7/2001 | Schultz |
| 6,259,937 B1 | 7/2001 | Schulman et al. |
| 6,264,825 B1 | 7/2001 | Blackburn et al. |
| 6,268,161 B1 | 7/2001 | Han et al. |
| 6,274,285 B1 | 8/2001 | Gries et al. |
| 6,275,717 B1 | 8/2001 | Gross et al. |
| 6,284,478 B1 | 9/2001 | Heller et al. |
| 6,285,897 B1 | 9/2001 | Kilcoyne et al. |
| 6,294,281 B1 | 9/2001 | Heller |
| 6,296,615 B1 | 10/2001 | Brockway et al. |
| 6,299,578 B1 | 10/2001 | Kurnik et al. |
| 6,300,002 B1 | 10/2001 | Webb et al. |
| 6,309,351 B1 | 10/2001 | Kurnik et al. |
| 6,309,384 B1 | 10/2001 | Harrington et al. |
| 6,309,526 B1 | 10/2001 | Fujiwara et al. |
| 6,325,978 B1 | 12/2001 | Labuda et al. |
| 6,325,979 B1 | 12/2001 | Hahn et al. |
| 6,329,161 B1 | 12/2001 | Heller et al. |
| 6,330,464 B1 | 12/2001 | Colvin et al. |
| 6,343,225 B1 | 1/2002 | Clark, Jr. |

| | | | | | | |
|---|---|---|---|---|---|---|
| 6,360,888 B1 | 3/2002 | McIvor et al. | | 7,169,289 B2 | 1/2007 | Schulein et al. |
| 6,365,670 B1 | 4/2002 | Fry | | 7,192,450 B2 | 3/2007 | Brauker et al. |
| 6,366,794 B1 | 4/2002 | Moussy et al. | | 7,225,535 B2 | 6/2007 | Feldman et al. |
| 6,368,274 B1 | 4/2002 | Van Antwerp et al. | | 7,329,239 B2 | 2/2008 | Safabash et al. |
| 6,372,244 B1 | 4/2002 | Antanavich et al. | | 7,344,499 B1 | 3/2008 | Prausnitz et al. |
| 6,400,974 B1 | 6/2002 | Lesho | | 7,364,592 B2 | 4/2008 | Carr-Brendel et al. |
| 6,406,066 B1 | 6/2002 | Uegane | | 7,417,164 B2 | 8/2008 | Suri |
| 6,409,674 B1 | 6/2002 | Brockway et al. | | 7,426,408 B2 | 9/2008 | DeNuzzio et al. |
| 6,424,847 B1 | 7/2002 | Mastrototaro et al. | | 7,471,972 B2 | 12/2008 | Rhodes et al. |
| 6,442,413 B1 | 8/2002 | Silver | | 7,632,228 B2 | 12/2009 | Brauker et al. |
| 6,447,448 B1 | 9/2002 | Ishikawa et al. | | 7,637,868 B2 | 12/2009 | Saint et al. |
| 6,447,542 B1 | 9/2002 | Weadock | | 7,657,297 B2 | 2/2010 | Simpson et al. |
| 6,454,710 B1 | 9/2002 | Ballerstadt et al. | | 2002/0022883 A1 | 2/2002 | Burg |
| 6,459,917 B1 | 10/2002 | Gowda et al. | | 2002/0042090 A1 | 4/2002 | Heller et al. |
| 6,461,496 B1 | 10/2002 | Feldman et al. | | 2002/0042561 A1 | 4/2002 | Schulman et al. |
| 6,466,810 B1 | 10/2002 | Ward et al. | | 2002/0055673 A1 | 5/2002 | Van Antwerp et al. |
| 6,471,689 B1 | 10/2002 | Joseph et al. | | 2002/0151796 A1 | 10/2002 | Koulik |
| 6,475,750 B1 | 11/2002 | Han et al. | | 2002/0151816 A1 | 10/2002 | Rich et al. |
| 6,477,392 B1 | 11/2002 | Honigs et al. | | 2002/0169369 A1 | 11/2002 | Ward et al. |
| 6,477,395 B2 | 11/2002 | Schulman et al. | | 2002/0182241 A1 | 12/2002 | Borenstein et al. |
| 6,484,046 B1 | 11/2002 | Say et al. | | 2002/0188185 A1 | 12/2002 | Sohrab |
| 6,497,729 B1 | 12/2002 | Moussy et al. | | 2002/0193885 A1 | 12/2002 | Legeay et al. |
| 6,512,939 B1 | 1/2003 | Colvin et al. | | 2003/0006669 A1 | 1/2003 | Pei et al. |
| 6,514,718 B2 | 2/2003 | Heller et al. | | 2003/0023317 A1 | 1/2003 | Brauker et al. |
| 6,520,997 B1 | 2/2003 | Pekkarinen et al. | | 2003/0032874 A1 | 2/2003 | Rhodes et al. |
| 6,527,729 B1 | 3/2003 | Turcott | | 2003/0036773 A1 | 2/2003 | Whitehurst et al. |
| 6,528,584 B2 | 3/2003 | Kennedy et al. | | 2003/0036803 A1 | 2/2003 | McGhan et al. |
| 6,534,711 B1 | 3/2003 | Pollack | | 2003/0059631 A1 | 3/2003 | Al-Lamee |
| 6,537,318 B1 | 3/2003 | Ita et al. | | 2003/0065254 A1 | 4/2003 | Schulman et al. |
| 6,541,107 B1 | 4/2003 | King et al. | | 2003/0070548 A1 | 4/2003 | Clausen |
| 6,545,085 B2 | 4/2003 | Kilgour et al. | | 2003/0076082 A1 | 4/2003 | Morgan et al. |
| 6,546,268 B1 | 4/2003 | Ishikawa et al. | | 2003/0078481 A1 | 4/2003 | McIvor et al. |
| 6,547,839 B2 | 4/2003 | Zhang et al. | | 2003/0078560 A1 | 4/2003 | Miller et al. |
| 6,551,496 B1 | 4/2003 | Moles et al. | | 2003/0091433 A1 | 5/2003 | Tam et al. |
| 6,558,320 B1 | 5/2003 | Causey | | 2003/0125613 A1 | 7/2003 | Enegren et al. |
| 6,558,321 B1 | 5/2003 | Burd et al. | | 2003/0130616 A1 | 7/2003 | Steil et al. |
| 6,565,509 B1 | 5/2003 | Say et al. | | 2003/0134347 A1 | 7/2003 | Heller et al. |
| 6,569,309 B2 | 5/2003 | Otsuka et al. | | 2003/0138674 A1 | 7/2003 | Zeikus et al. |
| 6,579,498 B1 | 6/2003 | Eglise | | 2003/0181794 A1 | 9/2003 | Rini et al. |
| 6,587,705 B1 | 7/2003 | Berner et al. | | 2003/0187338 A1 | 10/2003 | Say et al. |
| 6,591,125 B1 | 7/2003 | Buse et al. | | 2003/0199745 A1 | 10/2003 | Burson et al. |
| 6,615,078 B1 | 9/2003 | Burson et al. | | 2003/0211625 A1 | 11/2003 | Cohan |
| 6,618,934 B1 | 9/2003 | Feldman et al. | | 2003/0217966 A1 | 11/2003 | Tapsak et al. |
| 6,666,821 B2 | 12/2003 | Keimel | | 2003/0225361 A1 | 12/2003 | Sabra |
| 6,695,958 B1 | 2/2004 | Adam et al. | | 2003/0235817 A1 | 12/2003 | Bartkowiak et al. |
| 6,699,383 B2 | 3/2004 | Lemire et al. | | 2004/0011671 A1 | 1/2004 | Shults et al. |
| 6,702,857 B2 | 3/2004 | Brauker et al. | | 2004/0015063 A1 | 1/2004 | DeNuzzio et al. |
| 6,702,972 B1 | 3/2004 | Markle | | 2004/0045879 A1 | 3/2004 | Shults et al. |
| 6,721,587 B2 | 4/2004 | Gough | | 2004/0087671 A1 | 5/2004 | Tamada et al. |
| 6,737,158 B1 | 5/2004 | Thompson | | 2004/0106857 A1 | 6/2004 | Gough |
| 6,741,877 B1 | 5/2004 | Shults et al. | | 2004/0143173 A1 | 7/2004 | Reghabi et al. |
| 6,773,565 B2 | 8/2004 | Ono et al. | | 2004/0158138 A1 | 8/2004 | Kilcoyne et al. |
| 6,793,632 B2 | 9/2004 | Sohrab | | 2004/0167801 A1 | 8/2004 | Say et al. |
| 6,793,802 B2 | 9/2004 | Lee et al. | | 2004/0186362 A1 | 9/2004 | Brauker et al. |
| 6,804,544 B2 | 10/2004 | van Antwerp et al. | | 2004/0199059 A1 | 10/2004 | Brauker et al. |
| 6,862,465 B2 | 3/2005 | Shults et al. | | 2005/0008671 A1 | 1/2005 | Van Antwerp |
| 6,895,263 B2 | 5/2005 | Shin et al. | | 2005/0027180 A1 | 2/2005 | Goode et al. |
| 6,931,327 B2 | 8/2005 | Goode et al. | | 2005/0027181 A1 | 2/2005 | Goode et al. |
| 6,936,006 B2 | 8/2005 | Sabra | | 2005/0027463 A1 | 2/2005 | Goode et al. |
| 6,952,604 B2 | 10/2005 | DeNuzzio et al. | | 2005/0031689 A1 | 2/2005 | Shults et al. |
| 6,965,791 B1 | 11/2005 | Hitchcock et al. | | 2005/0033132 A1 | 2/2005 | Shults et al. |
| 6,972,080 B1 | 12/2005 | Tomioka et al. | | 2005/0043598 A1 | 2/2005 | Goode et al. |
| 6,991,643 B2 | 1/2006 | Saadat | | 2005/0051427 A1 | 3/2005 | Brauker et al. |
| 7,058,437 B2 | 6/2006 | Buse et al. | | 2005/0051440 A1 | 3/2005 | Simpson et al. |
| 7,074,307 B2 | 7/2006 | Simpson et al. | | 2005/0054909 A1 | 3/2005 | Petisce et al. |
| 7,081,195 B2 | 7/2006 | Simpson et al. | | 2005/0056552 A1 | 3/2005 | Simpson et al. |
| 7,108,778 B2 | 9/2006 | Simpson et al. | | 2005/0059871 A1 | 3/2005 | Gough et al. |
| 7,110,803 B2 | 9/2006 | Shults et al. | | 2005/0090607 A1 | 4/2005 | Tapsak et al. |
| 7,115,884 B1 | 10/2006 | Walt et al. | | 2005/0096519 A1 | 5/2005 | DeNuzzio et al. |
| 7,134,999 B2 | 11/2006 | Brauker et al. | | 2005/0103625 A1 | 5/2005 | Rhodes et al. |
| 7,136,689 B2 | 11/2006 | Shults et al. | | 2005/0112169 A1 | 5/2005 | Brauker et al. |
| 7,153,265 B2 | 12/2006 | Vachon | | 2005/0121322 A1 | 6/2005 | Say |
| 7,166,074 B2 | 1/2007 | Reghabi et al. | | 2005/0139489 A1 | 6/2005 | Davies et al. |

| | | | | | | |
|---|---|---|---|---|---|---|
| 2005/0143635 | A1 | 6/2005 | Kamath et al. | FR | 2656423 | 6/1991 |
| 2005/0177036 | A1 | 8/2005 | Shults et al. | FR | 2760962 | 9/1998 |
| 2005/0181012 | A1 | 8/2005 | Saint et al. | GB | 1442303 | 7/1976 |
| 2005/0182451 | A1 | 8/2005 | Griffin et al. | GB | 2149918 | 6/1985 |
| 2005/0192557 | A1 | 9/2005 | Brauker et al. | JP | 62058154 | 3/1987 |
| 2005/0211571 | A1 | 9/2005 | Schulein et al. | JP | 62083649 | 4/1987 |
| 2005/0242479 | A1 | 11/2005 | Petisce et al. | JP | 62083849 | 4/1987 |
| 2005/0245795 | A1 | 11/2005 | Goode et al. | JP | 63067560 | 3/1988 |
| 2005/0245799 | A1 | 11/2005 | Brauker et al. | JP | 02002913 | 1/1990 |
| 2005/0251083 | A1 | 11/2005 | Carr-Brendel et al. | JP | 3-293556 | 12/1991 |
| 2005/0271546 | A1 | 12/2005 | Gerber et al. | JP | 2002-189015 | 7/2002 |
| 2005/0272989 | A1 | 12/2005 | Shah et al. | WO | WO 89/02720 | 4/1989 |
| 2006/0015020 | A1 | 1/2006 | Neale et al. | WO | WO 90/00738 | 1/1990 |
| 2006/0016700 | A1 | 1/2006 | Brister et al. | WO | WO 91/09302 | 6/1991 |
| 2006/0189856 | A1 | 8/2006 | Petisce et al. | WO | WO 92/07525 | 5/1992 |
| 2006/0200022 | A1 | 9/2006 | Brauker et al. | WO | WO 92/13271 | 8/1992 |
| 2006/0222566 | A1 | 10/2006 | Brauker et al. | WO | WO 93/14693 | 8/1993 |
| 2006/0224108 | A1 | 10/2006 | Brauker et al. | WO | WO 93/19701 | 10/1993 |
| 2006/0257995 | A1 | 11/2006 | Simpson et al. | WO | WO 96/01611 | 1/1996 |
| 2006/0257996 | A1 | 11/2006 | Simpson et al. | WO | WO 96/14026 | 5/1996 |
| 2006/0263763 | A1 | 11/2006 | Simpson et al. | WO | WO 96/25089 | 8/1996 |
| 2006/0270922 | A1 | 11/2006 | Brauker et al. | WO | WO 96/30431 | 10/1996 |
| 2006/0270923 | A1 | 11/2006 | Brauker et al. | WO | WO 96/32076 | 10/1996 |
| 2006/0281985 | A1 | 12/2006 | Ward et al. | WO | WO 96/36296 | 11/1996 |
| 2007/0027370 | A1 | 2/2007 | Brauker et al. | WO | WO 97/01986 | 1/1997 |
| 2007/0032718 | A1 | 2/2007 | Shults et al. | WO | WO 97/43633 | 11/1997 |
| 2007/0045902 | A1 | 3/2007 | Brauker et al. | WO | WO 98/24358 | 6/1998 |
| 2007/0173711 | A1 | 7/2007 | Shah et al. | WO | WO 98/38906 | 9/1998 |
| 2007/0203966 | A1 | 8/2007 | Brauker et al. | WO | WO 99/56613 | 4/1999 |
| 2007/0235331 | A1 | 10/2007 | Simpson et al. | WO | WO 00/13003 | 3/2000 |
| 2007/0259217 | A1 | 11/2007 | Logan | WO | WO 00/19887 | 4/2000 |
| 2008/0021666 | A1 | 1/2008 | Goode et al. | WO | WO 00/32098 | 6/2000 |
| 2008/0045824 | A1 | 2/2008 | Tapsak et al. | WO | WO 00/33065 | 6/2000 |
| 2008/0187655 | A1 | 8/2008 | Markle et al. | WO | WO 00/59373 | 10/2000 |
| 2008/0188722 | A1 | 8/2008 | Markle et al. | WO | WO 00/74753 | 12/2000 |
| 2008/0188725 | A1 | 8/2008 | Markle et al. | WO | WO 01/12158 | 2/2001 |
| 2008/0228051 | A1 | 9/2008 | Shults et al. | WO | WO 01/20019 | 3/2001 |
| 2008/0228054 | A1 | 9/2008 | Shults et al. | WO | WO 01/20334 | 3/2001 |
| 2008/0242961 | A1 | 10/2008 | Brister et al. | WO | WO 01/43660 | 6/2001 |
| 2008/0262334 | A1 | 10/2008 | Dunn et al. | WO | WO 01/58348 | 8/2001 |
| 2008/0305009 | A1 | 12/2008 | Gamsey et al. | WO | WO 01/88524 | 11/2001 |
| 2008/0305506 | A1 | 12/2008 | Suri | WO | WO 02/053764 | 7/2002 |
| 2008/0306368 | A1 | 12/2008 | Goode et al. | WO | WO 02/097414 | 12/2002 |
| 2009/0012379 | A1 | 1/2009 | Goode et al. | WO | WO 2005/012873 | 2/2005 |
| 2009/0018418 | A1 | 1/2009 | Markle et al. | WO | WO 2005/057168 | 6/2005 |
| 2009/0018426 | A1 | 1/2009 | Markle et al. | WO | WO 2005/026689 | 10/2005 |
| 2009/0036763 | A1 | 2/2009 | Brauker et al. | | | |
| 2009/0045055 | A1 | 2/2009 | Rhodes et al. | | | |
| 2009/0061528 | A1 | 3/2009 | Suri | | | |
| 2009/0062633 | A1 | 3/2009 | Brauker et al. | | | |
| 2009/0081803 | A1 | 3/2009 | Gamsey et al. | | | |
| 2009/0177143 | A1 | 7/2009 | Markle et al. | | | |
| 2009/0264719 | A1 | 10/2009 | Markle et al. | | | |
| 2010/0041971 | A1 | 2/2010 | Goode, Jr. et al. | | | |
| 2010/0049024 | A1 | 2/2010 | Saint et al. | | | |
| 2010/0087724 | A1 | 4/2010 | Brauker et al. | | | |
| 2010/0160760 | A1 | 6/2010 | Shults et al. | | | |

FOREIGN PATENT DOCUMENTS

| | | |
|---|---|---|
| EP | 0107634 | 5/1984 |
| EP | 0 127 958 | 12/1984 |
| EP | 0 320 109 | 6/1989 |
| EP | 0 353 328 | 2/1990 |
| EP | 0 390 390 | 10/1990 |
| EP | 0 396 788 | 11/1990 |
| EP | 0534074 | 3/1993 |
| EP | 0535898 | 4/1993 |
| EP | 0 539 625 | 5/1993 |
| EP | 0 563 795 | 10/1993 |
| EP | 0885932 | 12/1998 |
| EP | 0 967 788 | 12/1999 |
| EP | 0817809 | 7/2002 |

OTHER PUBLICATIONS

Baker et al. Dynamic concentration challenges for biosensor characterization. Biosens Bioelectron 1993, 8, 433-441.

Bani Amer, M. M. An accurate amperometric glucose sensor based glucometer with eliminated cross-sensitivity. J Med Eng Technol 2002, 26, 208-13.

Beach et al. Subminiature implantable potentiostat and modified commercial telemetry device for remote glucose monitoring. IEEE Transactions on Instrumentation and Measurement 1999, 48, 1239-1245.

Bindra et al. Pulsed amperometric detection of glucose in biological fluids at a surface-modified gold electrode. Anal Chem 1989, 61, 2566-2570.

Bode, B. W. Clinical utility of the continuous glucose monitoring system. Diabetes Technol Ther 2000, 2 Suppl 1, S35-41.

Bode et al. Continuous glucose monitoring used to adjust diabetes therapy improves glycosylated hemoglobin: a pilot study. Diabetes Res Clin Pract 1999, 46, 183-190.

Bode et al. Using the continuous glucose monitoring system to improve the management of type 1 diabetes. Diabetes Technol Ther 2000, 2 Suppl 1, S43-8.

Bott, A. W. A Comparison of Cyclic Voltammetry and Cyclic Staircase Voltammetry. Current Separations 1997, 16:1, 23-26.

Brauker et al. Neovascularization of synthetic membranes directed by membrane microarchitecture, J Biomed Mater Res 1995, 29, 1517-1524.

Brauker et al. Sustained expression of high levels of human factor IX from human cells implanted within an immunoisolation device into athymic rodents. Hum Gene Ther 1998, 9, 879-888.

Bremer et al. Benchmark data from the literature for evaluation of new glucose sensing technologies. Diabetes Technol Ther 2001, 3, 409-418.

Brunner et al. Validation of home blood glucose meters with respect to clinical and analytical approaches. Diabetes Care 1998, 21, 585-590.

D'Arrigo at al. Porous-Si based bioreactors for glucose monitoring and drugs production. Proc. of SPIE 2003, 4982, 178-184.

Dixon at al. Characterization in vitro and in vivo of the oxygen dependence of an enzyme/polymer biosensor for monitoring brain glucose. J Neurosci Methods 2002, 119, 135-142.

Ernst et al. Reliable glucose monitoring through the use of microsystem technology. Anal Bioanal Chem 2002, 373, 758-761.

Fare at al. Functional characterization of a conducting polymer-based immunoassay system. Biosens Bioelectron 1998, 13, 459-470.

Frost et al. Implantable chemical sensors for real-time clinical monitoring: progress and challenges. Curr Opin Chem Biol 2002, 6, 633-641.

Geller et al. Use of an immunoisolation device for cell transplantation and tumor immunotherapy. Ann NY Acad Sci 1997, 831, 438-451.

Gerritsen, M. Problems associated with subcutaneously implanted glucose sensors. Diabetes Care 2000, 23, 143-5.

Gerritsen et al. Influence of inflammatory cells and serum on the performance of implantable glucose sensors. J Biomed Mater Res 2001, 54, 69-75.

Gerritsen et al. Performance of subcutaneously implanted glucose sensors for continuous monitoring. Neth J Med 1999, 54, 167-179.

Gilligan et al. Evaluation of a subcutaneous glucose sensor out to 3 months in a dog model. Diabetes Care 1994, 17:8, 882-887.

Gough et al. Immobilized glucose oxidase in implantable glucose sensor technology. Diabetes Technol Ther 2000, 2, 377-380.

Gross et al. Performance evaluation of the MiniMed continuous glucose monitoring system during patient home use. Diabetes Technol Ther 2000, 2, 49-56.

Gross et al. Efficacy and reliability of the continuous glucose monitoring system. Diabetes Technol Ther 2000, 2 Suppl 1, S19-26.

Gross, Todd, "Letters to the Editor Re: Diabetes Technology & Therapeutics, 2000;2:49-56," vol. 3, No. 1, p. 130-131, 2001.

Hall et al. Electrochemical oxidation of hydrogen peroxide at platinum electrodes, Part 1. An adsorption-controlled mechanism. Electrochimica Acta 1998, 43, 579-588.

Hall et al. Electrochemical oxidation of hydrogen peroxide at platinum electrodes. Part II: effect of potential. Electrochimica Acta 1998, 43, 2015-2024.

Hall et al. Electrochemical oxidation of hydrogen peroxide at platinum electrodes. Part III: Effect of temperature. Electrochimica Acta 1999, 44, 2455-2462.

Hall et al. Electrochemical oxidation of hydrogen peroxide at platinum electrodes. Part IV: phosphate buffer dependence. Electrochimica Acta 1999, 44, 4573-4582.

Hall et al. Electrochemical oxidation of hydrogen peroxide at platinum electrodes. Part V: Inhibition by chloride. Electrochimica Acta 2000, 45, 3573-3579.

Hitchman, M. Measurement of Dissolved Oxygen, Chemical Analysis 1978, 49, 34-123.

Huang, C., O'Grady, W.E; Yeager, E. Electrochemical Generation of Oxygen. 1: The Effects of Anions and Cations on Hydrogen Chemisorption and Aniodic Oxide Film Formation on Platinum Electrode. 2: The Effects of Anions and Cations on Oxygen Generation on Platinum Electrode, pp. 1-116, Aug. 1975.

Ishikawa et al. Initial evaluation of a 290-microm diameter subcutaneous glucose sensor: glucose monitoring with a biocompatible, flexible-wire, enzyme-based amperometric microsensor in diabetic and nondiabetic humans. J Diabetes Complications 1998, 12, 295-301.

Jensen et al. Fast Wave Forms for Pulsed Electrochemical Detection of Glucose by Incorporation of Reduction Desorption of Oxidation Products. Analytical Chemistry 1997, 69, 1776-1781.

Johnson et al. In vivo evaluation of an electroenzymatic glucose sensor implanted in subcutaneous tissue. Biosens Bioelectron 1992, 7, 709-714.

Jovanovic, L. The role of continuous glucose monitoring in gestational diabetes mellitus. Diabetes Technol Ther 2000, 2 Suppl 1, S67-71.

Kargol et al. Studies on the structural properties of porous membranes: measurement of linear dimensions of solutes. Biophys Chem 2001, 91, 263-271.

Kaufman, F. R. Role of the continuous glucose monitoring system in pediatric patients. Diabetes Technol Ther 2000, 2 Suppl 1, S49-52.

Kiechle, F.L. The impact of continuous glucose monitoring on hospital point-of-care testing programs. Diabetes Technol Ther 2001, 3, 647-649.

Koschinsky et al. Sensors for glucose monitoring: technical and clinical aspects. Diabetes Metab Res Rev 2001, 17, 113-123.

Kruger et al. Psychological motivation and patient education: a role for continuous glucose monitoring. Diabetes Technol Ther 2000, 2 Suppl 1, S93-7.

Lee et al. Effects of pore size, void volume, and pore connectivity on tissue responses. Society for Biomaterials 1999, $25^{th}$ Annual Meeting, 171.

Lerner et al. An implantable electrochemical glucose sensor. Ann N Y Acad Sci 1984, 428, 263-278.

Leypoldt et al. Model of a two-substrate enzyme electrode for glucose. Anal Chem 1984, 56, 2896-2904.

Makale et al. Tissue window chamber system for validation of implanted oxygen sensors. Am J Physiol Heart Circ Physiol 2003, 284, 1-24.

Malin et al, "Noninvasive Prediction of Glucose by Near-Infrared Diffuse Reflectance Spectroscopy," Clinical Chemistry 1999, 45:9:1651-1658.

Maran et al. Continuous subcutaneous glucose monitoring in diabetic patients: a multicenter analysis. Diabetes Care 2002, 25, 347-52.

Mastrototaro, J. J.; Gross, T. M., Reproducibility of the continuous glucose monitoring system matches previous reports and the intended use of the product. *Diabetes Care*, 26:256; author reply p. 257, 2003.

Matsumoto et al. A long-term lifetime amperometric glucose sensor with a perfluorocarbon polymer coating. Biosens Bioelectron 2001, 16, 271-276.

Miller, A. Human monocyte/macrophage activation and interleukin 1 generation by biomedical polymers. J Biomed Mater Res 1988, 23, 713-731.

Miller et al. Generation of IL-1 like activity in response to biomedical polymer implants: a comparison of in vitro and in vivo models. J Biomed Mater Res 1989, 23, 1007-1026.

Miller et al. In vitro stimulation of fibroblast activity by factors generated from human monocytes activated by biomedical polymers. Journal of J Biomed Mater Res 1989, 23, 911-930.

Moussy et al. Biomaterials community examines biosensor biocompatibility. Diabetes Technol Ther 2000, 2, 473-477.

Mowery et al. Preparation and characterization of hydrophobic polymeric films that are thromboresistant via nitric oxide release. Biomaterials 2000, 21, 9-21.

Myler at al. Ultra-thin-polysiloxane-film-composite membranes for the optimisation of amperometric oxidase enzyme electrodes. Biosens Bioelectron 2002, 17, 35-43.

Nam et al. A novel fabrication method of macroporous biodegradable polymer scaffolds using gas foaming salt as a porogen additive. J Biomed Mater Res 2000, 53, 1-7.

Palmisano et al. Simultaneous monitoring of glucose and lactate by an interference and cross-talk free dual electrode amperometric biosensor based on electropolymerized thin films. Biosens Bioelectron 2000, 15, 531-539.

Pitzer et al. Detection of hypoglycemia with the GlucoWatch biographer. Diabetes Care 2001, 24, 881-5.

Poitout et al. A glucose monitoring system for on line estimation in man of blood glucose concentration using a miniaturized glucose sensor implanted in the subcutaneous tissue and a wearable control unit. Diabetologia 1993, 36, 658-663.

Postlethwaite et al. Interdigitated Array Electrode as an Alternative to the Rotated Ring-Disk Electrode for Determination of the Reaction Products of Dioxygen Reduction. Analytical Chemistry 1996, 68, 2951-2958.

Ratner, B.D. Reducing capsular thickness and enhancing angiogenesis around implant drug release systems. J Control Release 2002, 78, 211-218.

Reach, G., "Letters to the Editor Re: Diabetes Technology & Therapeutics, 2000;2:49-56," vol. 3, No. 1, p. 129-130, 2001.

Rhodes et al., Prediction of pocket-portable and implantable glucose enzyme electrode performance from combined species permeability and digital simulation analysis. Analytical Chemistry 1994, 66, 1520-1529.

Sansen et al. A smart sensor for the voltammetric measurement of oxygen or glucose concentrations. Sensors and Actuators 1990, 1, 298-302.

Sansen et al. "Glucose sensor with telemetry system." Ko, W.H. (Ed). Implantable Sensors for Closed Loop Prosthetic Systems, Ch. 12, 167-175, Future Publishing Co. (1985).

Schmidt et al. Glucose concentration in subcutaneous extracellular space. Diabetes Care 1993, 16, 695-700.

Schoemaker at al. The SCGM1 System: Subcutaneous Continuous Glucose Monitoring Based on Microdialysis Technique. Diabetes Technol Ther 2003, 5, 599-608.

Shults et al. A telemetry-instrumentation system for monitoring multiple subcutaneously implanted glucose sensors. IEEE Transactions on Biomedical Engineering 1994, 41, 937-942.

Sieminski et al. Biomaterial-microvasculature interactions. Biomaterials 2000, 21, 2233-2241.

Skyler, J. S. The economic burden of diabetes and the benefits of improved glycemic control: the potential role of a continuous glucose monitoring system. Diabetes Technol Ther 2000, 2 Suppl 1, S7-12.

Steil et al. Determination of plasma glucose during rapid glucose excursions with a subcutaneous glucose sensor. Diabetes Technol Ther 2003, 5, 27-31.

Tanenberg at al. Continuous glucose monitoring system: a new approach to the diagnosis of diabetic gastroparesis. Diabetes Technol Ther 2000, 2 Suppl 1, S73-80.

Tang et al. Fibrin(ogen) mediates acute inflammatory responses to biomaterials. J Exp Med 1993, 178, 2147-2156.

Tang et al. Inflammatory responses to biomaterials. Am J Clin Pathol 1995, 103, 466-471.

Tang et al. Mast cells mediate acute inflammatory responses to implanted biomaterials. Proc Natl Acad Sci U S A 1998, 95, 8841-8846.

Tang et al. Molecular determinants of acute inflammatory responses to biomaterials. J Clin Invest 1996, 97, 1329-1334.

Thome-Duret et al. Modification of the sensitivity of glucose sensor implanted into subcutaneous tissue. Diabetes Metab 1996, 22, 174-178.

Tibell et al. Survival of macroencapsulated allogeneic parathyroid tissue one year after transplantation in nonirnmunosuppressed humans. Cell Transplant 2001, 10, 591-9.

Tierney et al. The GlucoWatch biographer: a frequent automatic and noninvasive glucose monitor. Ann Med 2000, 32, 632-641.

Updike et al. Enzymatic glucose sensors: improved long-term performance in vitro and in vivo. ASAIO Journal 1994, 40, 157-163.

Updike et al. "Principles of long-term fully implanted sensors with emphasis on radiotelemetric monitoring of blood glucose from inside a subcutaneous foreign body capsule (FBC)." *Biosensors in the body: continuous in vivo monitoring*, Chap. 4, pp. 117-137, John Wiley & Sons Lts., (1997).

Updike et al. A subcutaneous glucose sensor with improved longevity, dynamic range, and stability of calibration. Diabetes Care 2000, 23, 208-214.

Updike et al. The enzyme electrode. Nature 1967, 214, 986-988.

Wagner et al. A. Continuous amperometric monitoring of glucose in a brittle diabetic chimpanzee with a miniature subcutaneous electrode. Proc Natl Aced Sci U S A 1998, 95, 6379-6382.

Ward at al., Rise in background current over time in a subcutaneous glucose sensor in the rabbit: relevance to calibration and accuracy. Biosensors & Bioelectronics 2000, 15, 53-61.

Ward et al. A new amperometric glucose microsensor: in vitro and short-term in vivo evaluation. Biosensors & Bioelectronics 2002, 17,181-189.

Wilkins at al. "Integrated implantable device for long-term glucose monitoring," Biosens Bioelectron 1995, 10, 485-494.

Wilson et al. Enzyme-based biosensors for in vivo measurements. Chem Rev 2000, 100:2693-2704.

Wu et al. In situ electrochemical oxygen generation with an immunoisolation device. Ann N Y Acad Sci 1999, 875, 105-125.

Yang et al. Development of needle-type glucose sensor with high selectivity. Science and Actuators B 1998, 46, 249-256.

Answers.com. "xenogenic." The American Heritage Stedman's Medical Dictionary. Houghton Mifflin Company, 2002. Answers.com Nov. 7, 2006 http://www. Answers.com/topic/xenogenic.

Armour et al. Dec. 1990. Application of Chronic Intravascular Blood Glucose Sensor in Dogs. Diabetes 39:1519-1526.

Aussedat et al. 1997. A user-friendly method for calibrating a subcutaneous glucose sensor-based hypoglycaemic alarm. Biosensors & Bioelectronics 12(11):1061-1071.

Bellucci et al. Jan. 1986. Electrochemical behaviour of graphite-epoxy composite materials (GECM) in aqueous salt solutions, Journal of Applied Electrochemistry, 16(1):15-22.

Bindra et al. 1991. Design and In Vitro Studies of a Needle-Type Glucose Senso for Subcutaneous Monitoring. Anal. Chem 63:1692-96.

Bobbioni-Harsch et al. 1993. Lifespan of subcutaneous glucose sensors and their performances during dynamic glycaemia changes in rats, J. Biomed. Eng. 15:457-463.

Cass et al. "Ferrocene-mediated enzyme electrodes for amperometric determination of glucose," Anal. Chem., 36:667-71 (1984).

Davies, et al. 1992. Polymer membranes in clinical sensor applications. I. An overview of membrane function, Biomaterials, 13(14):971-978.

Heller, "Electrical wiring of redox enzymes," Acc. Chem. Res., 23:128-134 (1990).

Heller, A. 1992. Electrical Connection of Enzyme Redox Centers to Electrodes. J. Phys. Chem. 96:3579-3587.

Hicks, 1985. In Situ Monitoring, Clinical Chemistry, 31(12):1931-1935.

Hu, et al. 1993. A needle-type enzyme-based lactate sensor for in vivo monitoring, Analytica Chimica Acta, 281:503-511.

Kawagoe et al. 1991. Enzyme-modified organic conducting salt microelectrode, Anal. Chem. 63:2961-2965.

Kerner et al. "The function of a hydrogen peroxide-detecting electroenzymatic glucose electrode is markedly impaired in human sub-cutaneous tissue and plasma," Biosensors & Bioelectronics, 8:473-482 (1993).

Maidan et al. 1992. Elimination of Electrooxidizable Interferent-Produced Currents in Amperometric Biosensors, Analytical Chemistry, 64:2889-2896.

Mastrototaro et al. "An electroenzymatic glucose sensor fabricated on a flexible substrate," Sensors and Actuators B, 5:139-44 (1991).

McKean, et al. Jul. 7, 1988. A Telemetry Instrumentation System for Chronically Implanted Glucose and Oxygen Sensors. Transactions on Biomedical Engineering 35:526-532.

Moatti-Sirat et al. 1992. Towards continuous glucose monitoring: in vivo evaluation of a miniaturized glucose sensor implanted for several days in rat subcutaneous tissue. Diabetologia 35:224-230.

Murphy, et al. 1992. Polymer membranes in clinical sensor applications. II. The design and fabrication of permselective hydrogels for electrochemical devices, Biomaterials, 13(14):979-990.

Ohara, et al. Dec. 1993. Glucose electrodes based on cross-linked bis(2,2'-bipyridine)chloroosmium(+/2+) complexed poly(1-vinylimidazole) films, Analytical Chemistry, 65:3512-3517.

Pickup et al. "In vivo molecular sensing in diabetes mellitus: an implantable glucose sensor with direct electron transfer," Diabetologia, 32:213-217 (1989).

Pishko et al. "Amperometric glucose microelectrodes prepared through immobilization of glucose oxidase in redox hydrogels," Anal. Chem., 63:2268-72 (1991).

Reach et al. 1992. Can continuous glucose monitoring be used for the treatment of diabetes? Analytical Chemistry 64(5):381-386.
Rebrin et al. "Automated feedback control of subcutaneous glucose concentration in diabetic dogs," Diabetologia, 32:573-76 (1989).
Sakakida et al. 1993. Ferrocene-Mediated Needle Type Glucose Sensor Covered with Newly Designed Biocompatible Membran, Sensors and Actuators B 13-14:319-322.
Sharkawy et al. 1996. Engineering the tissue which encapsulates subcutaneous implants. I. Diffusion properties, J Biomed Mater Res, 37:401-412.
Shaw et al. "In vitro testing of a simply constructed, highly stable glucose sensor suitable for implantation in diabetic patients," Biosensors & Bioelectronics, 6:401-406 (1991).
Shichiri et al. 1985. Needle-type Glucose Sensor for Wearable Artificial Endocrine Pancreas in Implantable Sensors 197-210.
Shichiri et al. 1986. Telemetry Glucose Monitoring Device with Needle-Type Glucose Sensor: A Useful Tool for Blood Glucose Monitoring in Diabetic Individuals. Diabetes Care, Inc. 9(3):298-301.
Shichiri et al., 1989. Membrane Design for Extending the Long-Life of an Implantable Glucose Sensor. Diab. Nutr. Metab. 2:309-313.
Sternberg et al. 1988. Study and Development of Multilayer Needle-type Enzyme-based Glucose Microsensors. Biosensors 4:27-40.
Thompson et al., In Vivo Probes: Problems and Perspectives, Department of Chemistry, University of Toronto, Canada, pp. 255-261, 1986.
Velho et al. 1989. Strategies for calibrating a subcutaneous glucose sensor. Biomed Biochim Acta 48(11/12):957-964.
von Woedtke et al. 1989. In situ calibration of implanted electrochemical glucose sensors. Biomed Biochim. Acta 48(11/12):943-952.
English translation of Office Action received Dec. 19, 2007 in Japanese App. No. 10/538680.
European Search Report for App. No. 98908875.2 dated Apr. 29, 2004.
Office Action dated Oct. 24, 2007 in U.S. Appl. No. 11/055,779.
Office Action dated Nov. 1, 2007 in U.S. Appl. No. 11/034,343.
Office Action dated Dec. 26, 2007 in U.S. Appl. No. 11/021,046.
Office Action dated Jan. 15, 2008 in U.S. Appl. No. 11/034,344.
Office Action dated Jan. 23, 2008 in U.S. Appl. No. 09/447,227.
Office Action dated Mar. 24, 2008 in U.S. Appl. No. 10/838,912.
Office Action dated Jun. 5, 2008 in U.S. Appl. No. 10/846,150.
Office Action mailed Jun. 5, 2008 in U.S. Appl. No. 10/838,909.
Office Action dated Jun. 12, 2008 in U.S. Appl. No. 09/447,227.
Office Action dated Jun. 19, 2008 in U.S. Appl. No. 11/021,162.
Office Action dated Jun. 23, 2008 in U.S. Appl. No. 11/021,046.
Office Action dated Jul. 10, 2008 in U.S. Appl. No. 11/034,343.
Office Action dated Jul. 16, 2008 in U.S. Appl. No. 10/838,912.
Office Action dated Sep. 18, 2008 in U.S. Appl. No. 11/439,630.
Office Action dated Sep. 29, 2008 in U.S. Appl. No. 12/037,830.
Office Action dated Sep. 29, 2008 in U.S. Appl. No. 12/037,812.
Office Action dated Oct. 8, 2008 in U.S. Appl. No. 10/896,637.
Office Action dated Dec. 1, 2008 in U.S. Appl. No. 11/503,367.
Office Action dated Dec. 9, 2008 in U.S. Appl. No. 10/846,150.
Office Action dated Dec. 11, 2008 in U.S. Appl. No. 09/447,227.
Office Action dated Dec. 24, 2008 in U.S. Appl. No. 10/885,476.
Office Action dated Dec. 30, 2008 in U.S. Appl. No. 11/034,343.
Office Action dated Feb. 4, 2009 in U.S. Appl. No. 10/768,889.
Office Action dated Feb. 4, 2009 in U.S. Appl. No. 11/021,046.
Office Action dated Feb. 23, 2009 in U.S. Appl. No. 11/439,630.
Office Action dated Feb. 26, 2009 in U.S. Appl. No. 12/037,830.
Office Action dated Mar. 5, 2009 in U.S. Appl. No. 10/896,637.
Office Action mailed Mar. 16, 2009 in U.S. Appl. No. 10/838,909.
Office Action dated Apr. 1, 2009 in U.S. Appl. No. 12/037,812.
Office Action dated May 26, 2009 in U.S. Appl. No. 09/447,227.
Final Office Action dated Jun. 9, 2009 in U.S. Appl. No. 10/846,150.
Final Office Action dated Jun. 23, 2009 in U.S. Appl. No. 10/885,476.
Office Action dated Jul. 20, 2009 in U.S. Appl. No. 10/896,637.
Office Action dated Jul. 24, 2009 in U.S. Appl. No. 12/037,812.
ISR for PCT/US04/08206 filed Mar. 16, 2004.
IPRP for PCT/US04/008206 filed Mar. 16, 2004.
Bard et al. 1980. Electrochemical Methods. John Wiley & Sons, pp. 173-175.
Brooks, et al. "Development of an on-line glucose sensor for fermentation monitoring," Biosensors, 3:45-56 (1987/88).
Frohnauer, et al. 2001. Graphical human insulin time-activity profiles using standardized definitions. Diabetes Technology & Therapeutics 3(3):419-429.
Loffler, et al. 1995. Separation and determination of traces of ammonia in air by means of chromatomembrane cells. Fresenius J Anal Chem 352:613-614.
Moatti-Sirat, D, et al. 1992. Evaluating in vitro and in vivo the interference of ascorbate and acetaminophen on glucose detection by a needle-type glucose sensor. Biosensors and Bioelectronics 7:345-352.
Pickup, et al. "Implantable glucose sensors: choosing the appropriate sensor strategy," Biosensors, 3:335-346 (1987/88).
Pineda, et al. 1996. Bone regeneration with resorbable polymeric membranes. III. Effect of poly(L-lactide) membrane pore size on the bone healing process in large defects. J. Biomedical Materials Research 31:385-394.
Tierney, M. J.; Garg, S.; Ackerman, N. R.; Fermi, S. J.; Kennedy, J.; Lopatin, M.; Potts, R. O.; Tamada, J. A. 2000. Effect of acetaminophen on the accuracy of glucose measurements obtained with the GlucoWatch biographer. Diabetes Technol Ther 2:199-207.
Turner and Pickup, "Diabetes mellitus: biosensors for research and management," Biosensors, 1:85-115 (1985).
Wilson, et al. 1992. Progress toward the development of an implantable sensor for glucose. Clin. Chem. 38(9):1613-1617.
Office Action dated Apr. 9, 2003 in U.S. Appl. No. 09/916,386.
Office Action dated Sep. 5, 2006 in U.S. Appl. No. 09/916,711.
Office Action dated Feb. 14, 2006 in U.S. Appl. No. 09/916,711.
Office Action dated Jul. 1, 2005 in U.S. Appl. No. 09/916,711.
Office Action dated Jul. 23, 2004 in U.S. Appl. No. 09/916,711.
Office Action dated Dec. 23, 2004 in U.S. Appl. No. 09/916,711.
Office Action dated Feb. 11, 2004 in U.S. Appl. No. 09/916,711.
Office Action dated Sep. 24, 2003 in U.S. Appl. No. 09/916,711.
Office Action dated Dec. 7, 1998 in U.S. Appl. No. 08/811,473.
Office Action dated Jul. 17, 2007 in U.S. Appl. No. 09/447,227.
Office Action dated Mar. 9, 2007 in U.S. Appl. No. 09/447,227.
Office Action dated Aug. 1, 2006 in U.S. Appl. No. 09/447,227.
Office Action dated Apr. 4, 2006 in U.S. Appl. No. 09/447,227.
Office Action dated Sep. 22, 2005 in U.S. Appl. No. 09/447,227.
Office Action dated Nov. 28, 2003 in U.S. Appl. No. 09/447,227.
Office Action dated Jul. 9, 2003 in U.S. Appl. No. 09/447,227.
Office Action dated Jan. 16, 2003 in U.S. Appl. No. 09/447,227.
Office Action dated Jul. 15, 2002 in U.S. Appl. No. 09/447,227.
Office Action dated Jan. 17, 2002 in U.S. Appl. No. 09/447,227.
Office Action dated Aug. 15, 2001 in U.S. Appl. No. 09/447,227.
Office Action dated Aug. 14, 2001 in U.S. Appl. No. 09/489,588.
Office Action dated Feb. 27, 2002 in U.S. Appl. No. 09/489,588.
Office Action dated Jun. 12, 12003 in U.S. Appl. No. 09/489,588.
Office Action dated Sep. 21, 2004 in U.S. Appl. No. 10/657,843.
Office Action dated Sep. 21, 2004 in U.S. Appl. No. 09/916,858.
Office Action dated Mar. 22, 2004 in U.S. Appl. No. 09/916,858.
Office Action dated Aug. 14, 2006 in U.S. Appl. No. 11/039,269.
Office Action dated Feb. 24, 2006 in U.S. Appl. No. 11/039,269.
Office Action dated Nov. 2, 2005 in U.S. Appl. No. 11/039,269.
Office Action dated May 4, 2005 in U.S. Appl. No. 11/039,269.
Office Action dated Feb. 24, 2006 in U.S. Appl. No. 10/646,333.
Office Action dated Jun. 6, 2003 in U.S. Appl. No. 10/646,333.
Office Action dated Sep. 22, 2004 in U.S. Appl. No. 10/646,333.
Office Action dated Oct. 16, 2006 in U.S. Appl. No. 10/647,065.
Office Action dated May 22, 2006 in U.S. Appl. No. 10/896,772.
Office Action dated Dec. 14, 2005 in U.S. Appl. No. 10/896,772.
Office Action dated Jul. 19, 2005 in U.S. Appl. No. 10/896,772.
Office Action dated Jan. 11, 2005 in U.S. Appl. No. 10/896,772.
Office Action dated May 11, 2006 in U.S. Appl. No. 10/897,377.
Office Action dated Oct. 18, 2005 in U.S. Appl. No. 10/897,377.
Office Action dated Feb. 9, 2006 in U.S. Appl. No. 10/897,312.
Office Action dated Jan. 27, 2006 in U.S. Appl. No. 11/007,635.
Office Action dated May 23, 2007 in U.S. Appl. No. 11/055,779.
Office Action dated Sep. 21, 2007 in U.S. Appl. No. 10/838,912.
Poitout, et al. 1991. In Vitro and In Vivo Evaluation in Dogs of a Miniaturized Glucose Sensor, ASAIO Transactions, 37:M298-M300.

Office Action dated Aug. 19, 2009 in U.S. Appl. No. 11/021,046.
Office Action dated Aug. 7, 2009 in U.S. Appl. No. 12/037,830.
Office Action dated Sep. 2, 2009 in U.S. Appl. No. 11/439,630.
Supplementary European Search Report for App. No. 04759640.8 mailed Apr. 24, 2009.
Aalders et al. 1991. Development of a wearable glucose sensor; studies in healthy volunteers and in diabetic patients. The International Journal of Artificial Organs 14(2):102-108.
Abe et al. 1992. Characterization of glucose microsensors for intracellular measurements. Anal. Chem. 64(18):2160-2163.
Abel et al. 1984. Experience with an implantable glucose sensor as a prerequisite of an artificial beta cell, Biomed. Biochim. Acta 43(5):577-584.
Abel et al. 2002. Biosensors for in vivo glucose measurement: can we cross the experimental stage. Biosens Bioelectron 17:1059-1070.
Alcock & Turner. 1994. Continuous Analyte Monitoring to Aid Clinical Practice. IEEE Engineering in Med. & Biol. Mag. 13:319-325.
American Heritage Dictionary, 4th Edition. 2000. Houghton Mifflin Company, p. 82.
Amin et al. 2003. Hypoglycemia prevalence in prepubertal children with type 1 diabetes on standard insulin regimen: Use of continuous glucose monitoring system. Diabetes Care 26(3):662-667.
Asberg et al. 2003. Hydrogels of a Conducting Conjugated Polymer as 3-D Enzyme Electrode. Biosensors Bioelectronics. pp. 199-207.
Atanasov et al. 1997. Implantation of a refillable glucose monitoring-telemetry device. Biosens Bioelectron 12:669-680.
Bailey et al. 2007. Reduction in hemoglobin A1c with real-time continuous glucose monitoring: results from a 12-week observational study. Diabetes Technology & Therapeutics 9(3):203-210.
Bessman et al., Progress toward a glucose sensor for the artificial pancreas, Proceedings of a Workshop on Ion-Selective Microelectrodes, Jun. 4-5, 1973, Boston, MA, 189-197.
Biermann et al. 2008. How would patients behave if they were continually informed of their blood glucose levels? A simulation study using a "virtual" patient. Diab. Thechnol. & Therapeut., 10:178-187.
Bisenberger et al. 1995. A triple-step potential waveform at enzyme multisensors with thick-film gold electrodes for detection of glucose and sucrose. Sensors and Actuators, B 28:181-189.
Bland et al. 1990. A note on the use of the intraclass correlation coefficient in the evaluation of agreement between two methods of measurement. Comput. Biol. Med. 20(5):337-340.
Boedeker Plastics, Inc. 2009. Polyethylene Specifications Data Sheet, http://www.boedeker.com/polye_p.htm [Aug. 19, 2009 3:36:33 PM].
Boland et al. 2001. Limitations of conventional methods of self-monitoring of blood glucose. Diabetes Care 24(11):1858-1862.
Bowman, L.; Meindl, J. D. 1986. The packaging of implantable integrated sensors. IEEE Trans Biomed Eng BME33(2):248-255.
Brauker et al. 1996. Local Inflammatory Response Around Diffusion Chambers Containing Xenografts Transplantation 61(12):1671-1677.
Brauker et al. 2001. Unraveling Mysteries at the Biointerface: Molecular Mediator of Inhibition of Blood vessel Formation in the Foreign Body Capsule Revealed. Surfacts Biomaterials 6. 1;5.
Braunwald, 2008. Biomarkers in heart failure. *N. Engl. J. Med.*, 358: 2148-2159.
Bruckel et al. 1989. In vivo measurement of subcutaneous glucose concentrations with an enzymatic glucose sensor and a wick method. Klin Wochenschr 67:491-495.
Cai et al. 2004. A wireless, remote query glucose biosensor based on a pH-sensitive polymer. Anal Chem 76(4):4038-4043.
Campanella et al. 1993. Biosensor for direct determination of glucose and lactate in undiluted biological fluids. Biosensors & Bioelectronics 8:307-314.
Candas et al (1994). "An adaptive plasma glucose controller basedon a nonlinear insulin/glucose model." *IEEE Transactions on Biomedical Engineering*, 41(2): 116-124.
Cassidy et al., Apr. 1993. Novel electrochemical device for the detection of cholesterol or glucose, Analyst, 118:415-418.
Cellulose Acetate, Product Description, Product No. 419028, Sigma-Aldrich Corp., St. Louis, MO. Apr. 7, 2005.
Chase et al. 2001. Continuous subcutaneous glucose monitoring in children with type 1 diabetes. Pediatrics 107:222-226.
Chatterjee et al. 1997. Poly(ether Urethane) and poly(ether urethane urea) membranes with high $H_2S/CH_4$ selectivity, Journal of Membrane Science 135:99-106.
Chen et al. 2006. A noninterference polypyrrole glucose biosensor. Biosensors and Bioelectronics 22:639-643.
Ciba® Irgacure® 2959 Photoinitiator, Product Description, Ciba Specialty Chemicals Inc., Basel, Switzerland, Apr. 2, 1998.
Claremont et al. 1986. Subcutaneous implantation of a ferrocene-mediated glucose sensor in pigs. Diabetologia 29:817-821.
Claremont et al. Jul. 1986. Potentially-implantable, ferrocene-mediated glucose sensor. J. Biomed. Eng. 8:272-274.
Clark et al. 1981. One-minute electrochemical enzymic assay for cholesterol in biological materials, Clin. Chem. 27(12):1978-1982.
Clark et al. 1987. Configurational cyclic voltammetry: increasing the specificity and reliablity of implanted electrodes, IEEE/Ninth Annual Conference of the Engineering in Medicine and Biology Society, pp. 0782-0783.
Clark et al. 1988. Long-term stability of electroenzymatic glucose sensors implanted in mice. Trans Am Soc Artif Intern Organs 34:259-265.
CLSI. Performance metrics for continuous interstitial glucose monitoring; approved guideline, CLSI document POCT05-A. Wayne, PA: Clinical and Laboratory Standards Institute: 2008 28(33), 72 pp.
Colangelo et al. 1967. Corrosion rate measurements in vivo, Journal of Biomedical Materials Research, 1:405-414.
Colowick et al. 1976. Methods in Enzymlology, vol. XLIV, Immobilized Enzymes. New York: Academic Press.
Cox et al. 1985. Accuracy of perceiving blood glucose in IDDM. Diabetes Care 8(6):529-536.
Csoregi et al., 1994. Design, characterization, and one-point in vivo calibration of a subcutaneously implanted glucose electrode. Anal Chem. 66(19):3131-3138.
Dai et al. 1999. Hydrogel Membranes with Mesh Size Asymmetry Based on the Gradient Crosslink of Poly(vinyl alcohol). Journal of Membrane Science 156:67-79.
Danielsson et al. 1988. Enzyme thermistors, Methods in Enzymology, 137:181-197.
Dassau et al., In silico evaluation platform for artifical pancreatic β-cell development-a dynamic simulator for closed loop control with hardware-in-the-loop, Diabetes Technology & Therapeutics, 11(3):1-8, 2009.
Davis et al. 1983. Bioelectrochemical fuel cell and sensor based on a quinoprotein, alcohol dehydrogenase. *Enzyme Microb. Technol.*, vol. 5, September, 383-388.
Direct 30/30® Blood Glucose Sensor, (Markwell Medical) Catalog, © 1990, ELCO Diagnostics Company.
DuPont[1] Dimension AR® (Catalog), 1998.
Durliat et al. 1976. Spectrophotometric and electrochemical determinations of L(+)-lactate in blood by use of lactate dehydrogenase from yeast, Clin. Chem. 22(11):1802-1805.
Edwards Lifesciences. Accuracy for your and your patients. Marketing materials, 4 pp. 2002.
El Degheidy et al. 1986. Optimization of an implantable coated wire glucose sensor. J. Biomed Eng. 8: 121-129.
El-Khatib et al. 2007. Adaptive closed-loop control provides blood-glucose regulation using dual subcutaneous insulin and glucagon infusion in diabetic swine, Journal of Diabetes Science and Technology, 1(2):181-192.
El-Sa'ad et al. 1990. Moisture Absorption by Epoxy Resins: the Reverse Thermal Effect. Journal of Materials Science 25:3577-3582.
Fahy et al., An analysis: hyperglycemic intensive care patients need continuous glocuse monitoring—easier said than done, Journal of Diabetese Science and Technology, 2(2):201-204, Mar. 2008.
Feldman et al. 2003. A continuous glucose sensor based on wired enzyme technology—results from a 3-day trial in patients with type 1 diabetes. Diabetes Technol Ther 5(5):769-779.
Fischer et al. 1987. Assessment of subcutaneous glucose concentration: validation of the wick technique as a reference for implanted electrochemical sensors in normal and diabetic dogs, Diabetologia 30:940-945.
Fischer et al. 1989. Oxygen Tension at the Subcutaneous Implantation Site of Glucose Sensors. Biomed. Biochem 11/12:965-972.

Fischer et al. 1995. Hypoglycaemia-warning by means of subcutaneous electrochemical glucose sensors: an animal study, Horm. Metab. Rese. 27:53.

Freedman et al. 1991. Statistics, Second Edition, W.W. Norton & Company, p. 74.

Gabbay et al. 2008. Optical coherence tomography-based continuous noninvasive glucose monitoring in patients with diabetes. Diab. Thechnol. & Therapeut., 10:188-193.

Ganesan et al., Gold layer-based dual crosslinking procedure of glucose oxidase with ferrocene monocarboxylic acid provides a stable biosensor, Analytical Biochemistry 343:188-191, 2005.

Ganesh et al., Evaluation of the VIA® blood chemistry monitor for glucose in healthy and diabetic volunteers, Journal of Diabetese Science and Technology, 2(2):182-193, Mar. 2008.

Gao et al. 1989. Determination of Interfacial parameters of cellulose acetate membrane materials by HPLC, *J. Liquid Chromatography*, VI. 12, n. 11, 2083-2092.

Garg et al. 2004. Improved Glucose Excursions Using an Implantable Real-Time continuous Glucose Sensor in Adults with Type I Diabetes. Diabetes Care 27:734-738.

Gilligan et al. 2004, Feasibility of continuous long-term glucose monitoring from a subcutaneous glucose sensor in humans. Diabetes Technol Ther 6:378-386.

Godsland et al. 2001. Maximizing the Success Rate of Minimal Model Insulin Sensitivity Measurement in Humans: The Importance of Basal Glucose Levels. The Biochemical Society and the Medical Research Society, 1-9.

Gouda et al., Jul. 4, 2003. Thermal inactiviation of glucose oxidase, The Journal of Biological Chemistry, 278(27):24324-24333.

Gough et al. 2003. Frequency characterization of blood glucose dynamics. Annals of Biomedical Engineering 31:91-97.

Gregg et al. 1990. Cross-Linked Redox Gels Containing Glucose Oxidase for Amperometric Biosensor Applications. Anal. Chem. 62:258-263.

Guerci et al., Clinical performance of CGMS in type 1 diabetic patents treated by continuous subcutaneous insulin infusion using insulin analogs, Diabetes Care, 26:582-589, 2003.

Guo et al., Modification of cellulose acetate ultrafiltration membrane by gamma ray radiation, Shuichuli Jishi Bianji Weiyuanhui, 23(6):315-318, 1998 (Abstract only).

Hamilton Syringe Selection Guide. 2006. Syringe Selection. www.hamiltoncompany.com.

Harrison et al. 1988. Characterization of perfluorosulfonic acid polymer coated enzyme electrodes and a miniaturized integrated potentiostat for glucose analysis in whole blood. Anal. Chem. 60:2002-2007.

Hashiguchi et al. (1994). "Development of a miniaturized glucose monitoring system by combining a needle-type glucose sensor with microdialysis sampling method: Long-term subcutaneous tissue glucose monitoring in ambulatory diabetic patients," *Diabetes C*.

Heller, A. 1999. Implanted electrochemical glucose sensors for the management of diabetes. Annu Rev Biomed Eng 1:153-175.

Heller, A. 2003. Plugging metal connectors into enzymes. Nat Biotechnol 21:631-2.

Hoel, Paul G. 1976. Elementary Statistics, Fourth Edition. John Wiley & Sons, Inc.. pp. 113-114.

Hrapovic et al. 2003. Picoamperometric detection of glucose at ultrasmall platinum-based biosensors: preparation and characterization. Anal Chem 75:3308-3315.

http://www.merriam-webster.com/dictionary, definition for "aberrant," Aug. 19, 2008, p. 1.

Huang et al., "A 0.5mW Passive Telemetry IC for Biomedical Applications," Proceedings of the 23rd European Solid-State Circuits Conference (ESSCIRC '97), pp. 172-175, Sep. 1997, Southampton, UK.

Hunter et al. 2000. Minimally Invasive Glucose Sensor and Insulin Delivery System. MIT Home Automation and Healthcare Consortium. Progress Report No. 25.

Jaffari et al., Recent advances in amperometric glucose biosensors for in vivo monitoring, Physiol. Meas. 16 (1995) 1-15.

Jeutter, D. C. 1982. A transcutaneous implanted battery recharging and biotelemeter power switching system. IEEE Trans Biomed Eng 29:314-321.

Johnson (1991). "Reproducible electrodeposition of biomolecules for the fabrication of miniature electroenzymatic biosensors," *Sensors and Actuators B*, 5:85-89.

Johnson, R.C. et al. 1997. Abstract: Neovascularization of cell transplantation devices: Role of membrane architecture and encapsulated tissue, *Abstracts of Papers, Am. Chem. Soc.*, 214:2 p. 305-PMSE.

Kacaniklic May-Jun. 1994. Electroanalysis, 6(5-6):381-390.

Kamath et al. Calibration of a continuous glucose monitor: effect of glucose rate of change, Eighth Annual Diabetes Technology Meeting, Nov. 13-15, 2008, p. A88.

Kang et al. 2003. In vitro and short-term in vivo characteristics of a Kel-F thin film modified glucose sensor. Anal Sci 19:1481-1486.

Karube et al. 1993. Microbiosensors for acetylcholine and glucose Biosensors & Bioelectronics 8:219-228.

Kaufman et al. 2001. A pilot study of the continuous glucose monitoring system. Diabetes Care 24(12):2030-2034.

Keedy et al. 1991. Determination of urate in undiluted whole blood by enzyme electrode. *Biosensors & Bioelectronics*, 6: 491-499.

Kerner et al. 1988. A potentially implantable enzyme electrode for amperometric measurement of glucose, Horm Metab Res Suppl. 20:8-13.

Klueh et al. 2003. Use of Vascular Endothelia Cell Growth Factor Gene Transfer To Enhance Implantable Sensor Function in Vivo, Biosensor Function and Vegf-Gene Transfer, pp. 1072-1086.

Klueh et al. 2007. Inflammation and glucose sensors: use of dexamethasone to extend glucose sensor function and life span in vivo. Journal of Diabetes Science and Technology 1(4):496-504.

Ko, Wen H. 1985. Implantable Sensors for Closed-Loop Prosthetic Systems, Futura Pub. Co., Inc., Mt. Kisco, NY, Chapter 15:197-210.

Kondo et al. 1982. A miniature glucose sensor, implantable in the blood stream. Diabetes Care. 5(3):218-221.

Koschinsky et al. 1988. New approach to technical and clinical evaluation of devices for self-monitoring of blood glucose. Diabetes Care 11(8): 619-619.

Kost et al. 1985. Glucose-sensitive membranes containing glucose oxidase: activitiy, swelling, and permeability studies, Journal of Biomedical Materials Research 19:1117-1133.

Koudelka et al. 1989. In vivo response of microfabricated glucose sensors to glycemia changes in normal rats. Biomed Biochim Acta 48(11-12):953-956.

Koudelka et al. 1991. In-vivo behaviour of hypodermically implanted microfabricated glucose sensors. Biosensors & Bioelectronics 6:31-36.

Kraver et al. 2001. A mixed-signal sensor interface microinstrument. Sensors and Actuators A 91:266-277.

Kulys et al., 1994. Carbon-paste biosensors array for long-term glucose measurement, Biosensors& Beioelectronics, 9:491-500.

Kunjan et al., Automated blood sampling and glocuse sensing in critical care settings, Journal of Diabetes Science and Technology 2(3):194-200, Mar. 2008.

Kunzler et al. 1993. Hydrogels based on hydrophilic side chain siloxanes. Poly Mat Sci and Eng 69:226-227.

Kunzler et al. Aug. 21, 1995. Contact lens materials. Chemistry & Industry. 651-655.

Kurtz et al. 2005. Recommendations for blood pressure measurement in humans and experimental animals, Part 2: Blood pressure measurement in experimental animals, A statement for professionals from the subcommittee of professional and public education of.

Ladd et al., Structure Determination by X-ray Crystallography, 3rd ed. Plenum, 1996, Ch. 1, pp. xxi-xxiv and 1-58.

Lehmann et al. May 1994. Retrospective valication of a physiological model of glucose-iunsulin interaaction in tyhpe 1 diabetes mellitus, Med. Eng. Phys. 16:193-202.

Lewandowski et al. 1988. Evaluation of a miniature blood glucose sensor. Trans Am Soc Artif Intern Organs 34:255-258.

Linke et al. 1994. Amperometric biosensor for in vivo glucose sensing based on glucose oxidase immobilized in a redox hydrogel. Biosensors & Bioelectronics 9:151-158.

Lowe, 1984. Biosensors, Trends in Biotechnology, 2(3):59-65.

Luong et al. 2004. Solubilization of Multiwall Carbon Nanotubes by 3-Aminopropyltriethoxysilane Towards the Fabrication of Electrochemical Biosensors with Promoted Electron Transfer. Electroanalysis 16(1-2):132-139.

Lyandres et al. (2008). Progress toward an in vivo surface-enhanced raman spectroscopy glucose sensor. *Diabetes Technology & Therapeutics*, 10(4): 257-265.

Lyman D. 1960. Polyurethanes. I. The Solution Polymerization of Diisocyanates with Ethylene Glycol. J. Polymer Sci XLV:45:49.

Madaras et al. 1996. Microfabricated amperometric creatine and creatinine biosensors. Analytica Chimica Acta 319:335-345.

March, W. F. 2002. Dealing with the delay. Diabetes Technol Ther 4(1):49-50.

Marena et al. 1993. The artifical endocrine pancreas in clinical practice and research. Panminerva Medica 35(2):67-74.

Mascini et al. 1989. Glucose electrochemical probe with extended linearity for whole blood. *J Pharm Biomed Anal* 7(12): 1507-1512.

Mastrototaro, J. J. 2000. The MiniMed continuous glucose monitoring system. Diabetes Technol Ther 2(Suppl 1):S13-8.

Matsumoto et al. 1998. A micro-planar amperometeric glucose sensor unsusceptible to interference species. Sensors and Actuators B 49:68-72.

Matthews et al. 1988. An amperometric needle-type glucose sensor testing in rats and man. Diabetic Medicine 5:248-252.

Mazze et al. 2008. Characterizing glucose exposure for individuals with normal glucose tolerance using continuous glucose monitoring and ambulatory glucose profile analysis. Diab. Thechnol. & Therapeut., 10:149-159.

McCartney et al. 2001. Near-infrared fluorescence lifetime assay for serum glucose based on allophycocyanin-labeled concanavalin A. Anal Biochem 292:216-221.

McGrath et al. 1995. The use of differential measurements with a glucose biosensor for interference compensation during glucose determinations by flow injection analysis. Biosens Bioelectron 10:937-943.

Memoli et al. 2002. A comparison between different immobilised glucoseoxidase-based electrodes. J Pharm Biomed Anal 29:1045-1052.

Merriam-Webster Online Dictionary. Definition of "acceleration". http://www.merriam-webster.com/dictionary/Acceleration Jan. 11, 2010.

Merriam-Webster Online Dictionary. Definition of "nominal." http://www.m-w.com/dictionary/nominal Apr. 23, 2007.

Merriam-Webster Online Dictionary. Definition of "system". http://www.merriam-webster.com/dictionary/System Jan. 11, 2010.

Meyerhoff et al. 1992. On line continuous monitoring of subcutaneous tissue glucose in men by combining portable glucosensor with microdialysis. Diabetologia 35:1087-1092.

Moatti-Sirat et al., Reduction of acetaminophen interference in glucose sensors by a composite Nafion membrane: demonstration in rats and man, Diabetologia 37(6):610-616, Jun. 1994.

Morff et al. 1990. Microfabrication of reproducible, economical, electroenzymatic glucose sensors, Annual International Conference of the IEEE Engineering in Medicine and Biology Society, 12(2):0483-0484.

Mosbach et al. 1975. Determination of heat changes in the proximity of immobilized enzymes with an enzyme termistor and its use for the assay of metobolites, Biochim. Biophys. Acta. (Enzymology), 403:256-265.

Motonaka et al. 1993. Determination of cholesteral and cholesteral ester with novel enzyme microsensors, Anal. Chem. 65:3258-3261.

Muslu. 1991. Trickling filter performance. Apllied Biochemistry and Biotechnology 37:211-224.

Nafion® 117 Solution Product Description, Product No. 70160, Sigma-Aldrich Corp., St. Louis, MO. Apr. 7, 2005.

Nakayama et al. 1992. Surface fixation of hydrogels: heparin and glucose oxidase hydrogelated surfaces. ASAIO Journal M421-M424.

Ohara et al. 1994. "Wired" enzyme electrodes for amperometric determination of glucose or lactate in the presence of interfering substances. Anal Chem 66:2451-2457.

Okuda et al. 1971. Mutarotase effect on micro determinations of D-glucose and its anomers with β-D-glucose oxidase. Anal Biochem 43:312-315.

Oxford English Dictionary Online. Definition of "impending". http://www.askoxford.com/results/?view=dev dict&field-12668446 Impending&branch= Jan. 11, 2010.

Panetti 2002. Differential effects of sphingosine 1-phosphate and lysophosphatidic acid on endothelial cells. Biochimica et Biophysica Acta 1582:190-196.

Park et al. 2002. Gas separation properties of polysiloxane/polyether mixed soft segment urethane urea membranes, *J. Membrane Science*, 204: 257-269.

Patel et al. 2003. Amperometric glucose sensors based on ferrocene containing polymeric electron transfer systems-a preliminary report. Biosens Bioelectron 18:1073-6.

Peacock et al. 2008. Cardiac troponin and outcome in acute heart failure. N. Engl. J. Med., 358: 2117-2126.

Pegoraro et al. 1995. Gas transport properties of siloxane polyurethanes, Journal of Applied Polymer Science, 57:421-429.

Pfeiffer, E.F. 1990. The glucose sensor: the missing link in diabetes therapy, Horm Metab Res Suppl. 24:154-164.

Pfeiffer et al. 1992. On line continuous monitoring of subcutaneous tissue glucose is feasible by combining portable glucosensor with microdialysis. Horm. Metab. Res. 25:121-124.

Phillips and Smith. 1988. Bromedical Applications of Polyurethanes: Implications of Failure Mechanisms. J. Biomat. Appl. 3:202-227.

Pichert et al. 2000. Issues for the coming age of continuous glucose monitoring Diabetes Educ 26(6):969-980.

Pickup et al. 1988. Progress towards in vivo glucose sensing with a ferrocene-mediated amperometric enzyme electrode. 34-36.

Pickup et al. 1989. Potentially-implantable, amperometric glucose sensors with mediated electron transfer: improving the operating stability. Biosensors 4:109-119.

Pickup et al. 1993. Developing glucose sensors for in vivo use. Elsevier Science Publishers Ltd (UK), TIBTECH vol. 11: 285-291.

Pinner et al., Cross-linking of cellulose acetate by ionizing radiation, Nature, vol. 184, 1303-1304, Oct. 24, 1959.

Poitout et al. 1994. Development of a glucose sensor for glucose monitoring in man: the disposable implant concept. Clinical Materials 15:241-246.

Prabhu et al. 1981. Electrochemical studies of hydrogen peroxide at a platinum disc electrode, Electrochimica Acta 26(6):725-729.

Quinn et al. 1995. Kinetics of glucose delivery to subcutaneous tissue in rats measured with 0.3-mm amperometric microsensors. The American Physiological Society E155-E161.

Quinn et al. 1997. Biocompatible, glucose-permeable hydrogel for in situ coating of implantable biosensors. Biomaterials 18:1665-1670.

Rabah et al., 1991. Electrochemical wear of graphite anodes during electrolysis of brine, Carbon, 29(2):165-171.

Reach et al. 1986. A Method for Evaluating in vivo the Functional Characteristics of Glucose Sensors. Biosensors 2:211-220.

Reach, G. 2001. Which threshold to detect hypoglycemia? Value of receiver-operator curve analysis to find a compromise between sensitivity and specificity. Diabetes Care 24(5):803-804.

Rebrin et al. 1992. Subcutaenous glucose monitoring by means of electrochemical sensors: fiction or reality? J. Biomed. Eng. 14:33-40.

Reusch. 2004. Chemical Reactivity. Organometallic Compounds. Virtual Textbook of Organic Chem. pp. 1-16, http://www.cem.msu.edu/~reusch/VirtualText/orgmetal.htm.

Rigla et al. 2008. Real-time continuous glucose monitoring together with telemedical assitance improves glycemic control and glucose stability in pump-treated patients. Diab. Thechnol. & Therapeut., 10:194-199.

Rivers et al., Central venous oxygen saturation monitoring in the critically ill patient, Current Opinion in Critical Care, 7:204-211, 2001.

Sachlos et al. 2003. Making Tissue Engineering Scaffolds Work. Review on the Application of Sold Freeform Fabrication Technology to the Production of Tissue Engineering Scaffolds. European Cells and Materials 5:29-40.

Sakakida et al. 1992. Development of Ferrocene-Mediated Needle-Type Glucose Sensor as a Measure of True Subcutaneous Tissue Glucose Concentrations. Artif. Organs Today 2(2):145-158.

Salardi et al. 2002. The glucose area under the profiles obtained with continuous glucose monitoring system relationships with HbA1c in pediatric type 1 diabetic patients. Diabetes Care 25(10):1840-1844.

San Diego Plastics, Inc. 2009. Polyethylene Data Sheet, http://www.sdplastics.com/polyeth.html.

Sanders et al. 2003. Fibrous Encapsulation of Single Polymer Microfibers Depends on their Vertical Dimension in subcutaneous Tissue Polymer Microfibers pp. 1181-1187.

Schmidtke et al., Measurement and modeling of the transient difference between blood and subcutaneous glucose concentrations in the rat after injection of insulin. *Proc Natl Aced Sci U S A*. 1998, 95, 294-299.

Schoonen et al. 1990. Development of a potentially wearable glucose sensor for patients with diabetes mellitus: design and in-vitro evaluation. Biosensors & Bioelectronics 5:37-46.

Schuler et al. 1999. Modified gas-permeable silicone rubber membranes for covalent immobilisation of enzymes and their use in biosensor development. Analyst 124:1181-1184.

Selam, J. L. 1997. Management of diabetes with glucose sensors and implantable insulin pumps. From the dream of the 60s to the realities of the 90s. ASAIO J, 43:137-142.

Service et al. 1970. Mean amplitude of glycemic excursions, a measure of diabetic instability. Diabetes, 19: 644-655.

Service et al. 1987. Measurements of glucose control. Diabetes Care, 10: 225-237.

Service, R. F. 2002. Can sensors make a home in the body? Science 297:962-3.

Shichiri et al. 1982. Wearable artificial endocrine pancrease with needle-type glucose sensor. Lancet 2:1129-1131.

Shichiri et al. 1983. Glycaemic Control in Pancreatectomized Dogs with a Wearable Artificial Endocrine Pancreas. Diabetologia 24:179-184.

Slater-Maclean et al. 2008. Accuracy of glycemic measurements in the critically ill. Diab. Thechnol. & Therapeut., 10:169-177.

Sokol et al. 1980, Immobilized-enzyme rate-determination method for glucose analysis, Clin. Chem. 26(1):89-92.

Sriyudthsak et al. 1996. Enzyme-epoxy membrane based glucose analyzing system and medical applications. Biosens Bioelectron 11:735-742.

Stern et al., 1957. Electrochemical polarization: 1. A theoretical analysis of the shape of polarization curves, Journal of the Electrochemical Society, 104(1):56-63.

Sternberg et al. 1988. Covalent enzyme coupling on cellulose acetate membranes for glucose sensor development. Anal. Chem. 69:2781-2786.

Stokes. 1988. Polyether Polyurethanes: Biostable or Not? J. Biomat. Appl. 3:228-259.

Suh et al. 2002. Behavior of fibroblasts on a porous hyaluronic acid incorporated collagen matrix. Yonsei Medical Journal 43(2):193-202.

Sumino T. et al. 1998. Preliminary study of continuous glucose monitoring with a microdialysis technique. Proceedings of the IEEE, 20(4):1775-1778.

Takegami et al. 1992. Pervaporation of ethanol water mixtures using novel hydrophobic membranes containing polydimethylsiloxane, Journal of Membrance Science, 75(93-105).

Tatsuma et al. 1991. Oxidase/peroxidase bilayer-modified electrodes as sensors for lactate, pyruvate, cholesteral and uric acid, Analytica Chimica Acta, 242:85-89.

Thome et al. 1995. -Abstract—Can the decrease in subcutaneous glucose concentration precede the decrease in blood glucose level? Proposition for a push-pull kinetics hypothesis, Horm. Metab. Res. 27:53.

Thomé-Duret et al. 1996. Modification of the sensitivity of glucose sensor implanted into subcutaneous tissue. Diabetes Metabolism, 22:174-178.

Thomé-Duret et al. 1998. Continuous glucose monitoring in the free-moving rat. Metabolism, 47:799-803.

Torjman et al., Glucose monitoring in acute care: technologies on the horizon, Journal of Deabetes Science and Technology, 2(2):178-181, Mar. 2008.

Trecroci, D. 2002. A Glimpse into the Future- Continuous Monitoring of Glucose with a Microfiber. Diabetes Interview 42-43.

Tse and Gough. 1987. Time-Dependent Inactivation of Immobilized Glucose Oxidase and Catalase. Biotechnol. Bioeng. 29:705-713.

Turner et al. 1984. Carbon Monoxide: Acceptor Oxidoreductase from Pseudomonas Thermocarboxydovorans Strain C2 and its use in a Carbon Monoxide Sensor. Analytica Chimica Acta, 163: 161-174.

Turner, A.P.F. 1988. Amperometric biosensor based on mediator-modified electrodes. Methods in Enzymology 137:90-103.

Unger et al. 2004. Glucose control in the hospitalized patient. Emerg Med 36(9):12-18.

Updike et al. 1988. Laboratory Evaluation of New Reusable Blood Glucose Sensor. Diabetes Care, 11:801-807.

Utah Medical Products Inc., Blood Pressure Tranducers product specifications. 6 pp. 2003-2006, 2003.

Vadgama, P. Nov. 1981. Enzyme electrodes as practical biosensors. Journal of Medical Engineering & Technology 5(6):293-298.

Vadgama. 1988. Diffusion limited enzyme electrodes. NATO ASI Series: Series C, Math and Phys. Sci. 226:359-377.

Van den Berghe 2004. Tight blood glucose control with insulin in "real-life" intensive care. Mayo Clin Proc 79(8):977-978.

Velho et al. 1989. In vitro and in vivo stability of electrode potentials in needle-type glucose sensors. Influence of needle material. Diabetes 38:164-171.

Wade Jr., L.G. Organic Chemistry, Chapter 17, Reactions of Aromatic Compounds pp. 762-763, 1987.

Wang et al. 1994. Highly Selective Membrane-Free, Mediator-Free Glucose Biosensor. Anal. Chem. 66:3600-3603.

Wang et al. 1997. Improved ruggedness for membrane-based amperometric sensors using a pulsed amperometric method. Anal Chem 69:4482-4489.

Ward et al. 2000. Understanding Spontaneous Output Fluctuations of an Amperometric Glucose Sensor: Effect of Inhalation Anesthesia and e of a Nonenzyme Containing Electrode. ASAIO Journal 540-546.

Wientjes, K. J. C. 2000. Development of a glucose sensor for diabetic patients (Ph.D. Thesis).

Wikipedia 2006. "Intravenous therapy," http://en.wikipedia.org/wiki/Intravenous_therapy, Aug. 15, 2006, 6 pp.

Wiley Electrical and Electronics Engineering Dictionary. 2004. John Wiley & Sons, Inc. pp. 141, 142, 548, 549.

Wilkins et al. 1988. The coated wire electrode glucose sensor, Horm Metab Res Suppl., 20:50-55.

Wilkins et al. 1996. Glucose monitoring: state of the art and future possibilities. Med Eng Phys 18:273-288.

Wood, W. et al. Mar. 1990. Hermetic Sealing with Epoxy. Mechanical Engineering 1-3.

Woodward. 1982. How Fibroblasts and Giant Cells Encapsulate Implants: Considerations in Design of Glucose Sensor. Diabetes Care 5:278-281.

Worsley et al., Measurement of glucose in blood with a phenylboronic acid optical sensor, Journal of Diabetes Science and Technology, 2(2):213-220, Mar. 2008.

Wright et al., Bioelectrochemical dehalogenations via direct electrochemistry of poly(ethylene oxide)- modified myoglobin, Electrochemistry Communications 1 (1999) 603-611.

Yamasaki, Yoshimitsu. Sep. 1984. The development of a needle-type glucose sensor for wearable artificial endocrine pancreas. Medical Journal of Osaka University 35(1-2):25-34.

Yamasaki et al. 1989. Direct measurement of whole blood glucose by a needle-type sensor. Clinica Chimica Acta. 93:93-98.

Yang et al (1996). "A glucose biosensor based on an oxygen electrode: In-vitro performances in a model buffer solution and in blood plasma," Biomedical Instrumentation & Technology, 30:55-61.

Yang, et al. 2004. A Comparison of Physical Properties and Fuel Cell Performance of Nafion and Zirconium Phosphate/Nafion Composite Membranes. Journal Of Membrane Science 237:145-161.

Ye et al. 1993. High Current Density 'Wired' Quinoprotein Glucose Dehydrogenase Electrode. Anal. Chem. 65:238-241.

Zamzow et al. 1990. Development and evaluation of a wearable blood glucose monitor, ASAIO Transactions; 36(3): pp. M588-M591.

Zethelius et al. 2008. Use of multiple biomarkers to improve the prediction of death from cardiovascular causes. N. Engl. J. Med., 358: 2107-2116.

Zhang et al (1993). Electrochemical oxidation of $H_2O_2$ on Pt and Pt + Ir electrodes in physiological buffer and its applicability to $H_2O_2$-based biosensors. *J. Electroanal. Chem.*, 345:253-271.

Zhang et al.1993. In vitro and in vivo evaluation of oxygen effects on a glucose oxidase based implantable glucose sensor. Analytica Chimica Acta, 281:513-520.

Zhang et al. 1994. Elimination of the acetaminophen interference in an implantable glucose sensor. Analytical Chemistry 66(7):1183-1188.

Zhu et al. (1994). "Fabrication and characterization of glucose sensors based on a microarray $H_2O_2$ electrode." *Biosensors & Bioelectronics*, 9: 295-300.

Zhu et al. 2002. Planar amperometric glucose sensor based on glucose oxidase immobilized by chitosan film on prussian blue layer. Sensors, 2:127-136.

Office Action dated Dec. 8, 2009 in U.S. Appl. No. 09/447,227.
Office Action dated Jan. 14, 2010 in U.S. Appl. No. 09/447,227.
Office Action dated Feb. 26, 2010 in U.S. Appl. No. 11/546,157.
Office Action dated Jan. 7, 2010 in U.S. Appl. No. 10/846,150.
Office Action dated Jun. 4, 2010 in U.S. Appl. No. 10/846,150.
Office Action dated Feb. 23, 2010 in U.S. Appl. No. 12/037,830.
Office Action dated Jun. 11, 2010 in U.S. Appl. No. 12/037,830.
Office Action dated Jun. 4, 2010 in U.S. Appl. No. 12/037,812.
Office Action dated Mar. 5, 2010 in U.S. Appl. No. 11/416,058.
Office Action dated Mar. 4, 2010 in U.S. Appl. No. 11/416,346.
Office Action dated Nov. 17, 2006 in U.S. Appl. No. 10/842,716.
Office Action dated May 21, 2007 in U.S. Appl. No. 10/842,716.
Office Action dated Oct. 8, 2008 in U.S. Appl. No. 10/842,716.
Office Action dated Jul. 10, 2009 in U.S. Appl. No. 10/842,716.
Office Action dated Feb. 16, 2010 in U.S. Appl. No. 10/842,716.
Office Action dated Jul. 9, 2010 in U.S. Appl. No. 10/842,716.
Office Action dated Jan. 13, 2010 in U.S. Appl. No. 12/139,305.
Office Action dated Jan. 22, 2010 in U.S. Appl. No. 11/439,630.
Office Action dated Dec. 31, 2009 in U.S. Appl. No. 11/503,367.
Office Action dated Feb. 3, 2010 in U.S. Appl. No. 11/503,367.
Office Action dated Jun. 21, 2010 in U.S. Appl. No. 12/137,396.

OPTIMIZED SENSOR GEOMETRY FOR AN IMPLANTABLE GLUCOSE SENSOR

This application is a division of U.S. application Ser. No. 10/646,333 filed Aug. 22, 2003 now U.S. Pat. No. 7,134,999, which claims the benefit of priority under 35 U.S.C. §119(e) to U.S. Provisional Application No. 60/460,825, filed Apr. 4, 2003, the contents of which are hereby incorporated by reference in their entirety.

FIELD OF THE INVENTION

The present invention relates generally to implantable sensors that measure the concentration of an analyte in a biological fluid. The sensor geometry optimizes the healing at the sensor-tissue interface and is less amenable to accidental movement due to shear and rotational forces than other sensor configurations.

BACKGROUND OF THE INVENTION

Implantable analyte sensors that are placed in the subcutaneous tissue or other soft tissue sites must develop and sustain a stable biointerface that allows the continuous and timely transport of analytes across the interface between the tissue and the device. For example, in the case of a glucose sensor, glucose must be able to freely diffuse from surrounding blood vessels to a membrane of the sensor. Glucose sensors may be implanted in the subcutaneous tissue or other soft tissue. Such devices include glucose oxidase based amperometric sensors that sense glucose for weeks, months or longer after implantation.

While the utility of such devices for glucose sensing has been demonstrated, the consistency of function for such devices is not optimal. For a particular device, the sensor may, for example: 1) fail to function (namely, fail to track glucose effectively) in a stable manner during the first few weeks after implantation; 2) not work at all during the first few weeks, but subsequently begin to function in a stable manner; 3) function well during the first few weeks, lose function, then regain effectiveness or never recover function; or 4) work immediately, and continue to function with high accuracy throughout the course of a several month study.

Glucose sensors with improved acceptance within the host tissue and decreased variability of response are required for reliable functionality in vivo. Accordingly, the present invention discloses systems and methods for providing this improved functionality and consistency of analyte sensor in a host.

SUMMARY OF THE INVENTION

A sensor, especially a sensor suitable for implantation into soft tissue that provides accurate analyte measurements while offering consistency of function is highly desirable.

Accordingly, in a first embodiment an implantable sensor is provided for use in measuring a concentration of an analyte in a bodily fluid, the sensor including a body including a sensing region adapted for transport of analytes between the sensor and the bodily fluid, wherein the sensing region is located on a curved portion of the body such that when a foreign body capsule forms around the sensor, a contractile force is exerted by the foreign body capsule toward the sensing region.

In an aspect of the first embodiment, the sensor is a subcutaneous sensor.

In an aspect of the first embodiment, the sensor is an intramuscular sensor.

In an aspect of the first embodiment, the sensor is an intraperitoneal sensor.

In an aspect of the first embodiment, the sensor is an intrafascial sensor.

In an aspect of the first embodiment, the sensor is suitable for implantation in an axillary region.

In an aspect of the first embodiment, the sensor is suitable for implantation in a soft tissue of a body.

In an aspect of the first embodiment, the sensor is suitable for implantation at the interface between two tissue types.

In an aspect of the first embodiment, the sensor includes a plurality of sensor regions.

In an aspect of the first embodiment, the plurality of sensor regions are located on curved portions of the body.

In an aspect of the first embodiment, the body includes a first major surface and a second major surface, and wherein the sensing region is located on the first surface, and wherein the second surface is flat.

In an aspect of the first embodiment, the body includes a first major surface and a second major surface, and wherein the sensing region is located on the first major surface, and wherein the second major surface includes a curvature.

In an aspect of the first embodiment, the body includes a first major surface and a second major surface, and wherein the sensor region is situated at a position on the first major surface offset from a center point of the first major surface.

In an aspect of the first embodiment, the body includes a first major surface and a second major surface, and wherein the sensor region is situated on the first major surface approximately at a center point of the first major surface.

In an aspect of the first embodiment, the body includes a first surface and a second surface, and wherein the sensor region is situated approximately at an apex of the first surface.

In an aspect of the first embodiment, the body includes a first surface and a second surface, and wherein the first surface, when viewed from a direction perpendicular to a center of the first surface, has a substantially rectangular profile.

In an aspect of the first embodiment, the body includes a first surface and a second surface, and wherein the first surface, when viewed from a direction perpendicular to a center of the first surface, has a substantially rectangular profile with rounded corners.

In an aspect of the first embodiment, the body includes a first surface and a second surface, and wherein the first surface, when viewed from a direction perpendicular to a center of the first surface, has a substantially oval profile.

In an aspect of the first embodiment, the body includes a first surface and a second surface, and wherein the first surface, when viewed from a direction perpendicular to a center of the first surface, has a substantially circular profile.

In an aspect of the first embodiment, the body is substantially cuboidal defined by six faces, eight vertices, and twelve edges, wherein at least one of the faces includes the sensing region.

In an aspect of the first embodiment, at least two of the faces are substantially curved.

In an aspect of the first embodiment, at least four of the faces are substantially curved.

In an aspect of the first embodiment, all six of the faces are substantially curved.

In an aspect of the first embodiment, the edges are substantially rounded.

In an aspect of the first embodiment, the vertices are substantially rounded.

In an aspect of the first embodiment, the entire body is curved.

In an aspect of the first embodiment, the body is substantially cylindrical defined by a curved lateral surface and two ends, and wherein the sensor region is located on the lateral surface.

In an aspect of the first embodiment, the body is substantially cylindrical defined by a curved lateral surface and two ends, and wherein at least one of the ends includes the substantially curved portion on which the sensor region is located.

In an aspect of the first embodiment, the body is substantially spherical.

In an aspect of the first embodiment, the body is substantially ellipsoidal.

In an aspect of the first embodiment, the body includes a first surface on which the sensing region is located and a second surface, and wherein the first surface includes anchoring material thereon for supporting tissue ingrowth.

In an aspect of the first embodiment, the second surface is located opposite the first surface, and wherein the second surface includes anchoring material thereon for supporting tissue ingrowth.

In an aspect of the first embodiment, the second surface is located opposite the first surface, and wherein the second surface is substantially smooth and includes a biocompatible material that is non-adhesive to tissues.

In an aspect of the first embodiment, the second surface is curved.

In an aspect of the first embodiment, a mechanical anchoring mechanism is formed on the body.

In an aspect of the first embodiment, the curved portion includes a plurality of radii of curvature.

In an aspect of the first embodiment, the curved portion includes a radius of curvature between about 0.5 mm and about 10 cm.

In an aspect of the first embodiment, the curved portion includes a radius of curvature between about 1 cm and about 5 cm.

In an aspect of the first embodiment, the curved portion includes a radius of curvature between about 2 cm and about 3 cm.

In an aspect of the first embodiment, the curved portion includes a radius of curvature between about 2.5 cm and about 2.8 cm.

In an aspect of the first embodiment, the sensor includes a major surface and wherein the curved portion is located on at least a portion of the major surface.

In an aspect of the first embodiment, the body further includes a flat portion adjacent the curved portion.

In an aspect of the first embodiment, an interface between the flat portion and the curved portion includes a gradual transition.

In an aspect of the first embodiment, the body includes a first major surface on which the sensing region is located and a second major surface, and wherein the first and second major surfaces together account for at least about 40% of the surface area of the device.

In an aspect of the first embodiment, the first and second major surfaces together account for at least about 50% of the surface area of the device.

In an aspect of the first embodiment, the body includes a first major surface on which the sensing region is located and a second major surface, wherein the first major surface has edges between which a width of the first major surface can be measured, and wherein the sensing region is spaced away from the edges by a distance that is at least about 10% of the width of the first major surface.

In an aspect of the first embodiment, the sensing region is spaced away from the edges by a distance that is at least about 15% of the width of the first major surface.

In an aspect of the first embodiment, the sensing region is spaced away from the edges by a distance that is at least about 20% of the width of the first major surface.

In an aspect of the first embodiment, the sensing region is spaced away from the edges by a distance that is at least about 25% of the width of the first major surface.

In an aspect of the first embodiment, the sensing region is spaced away from the edges by a distance that is at least about 30% of the width of the first major surface.

In an aspect of the first embodiment, the spacing of the sensing region from the edges is true for at least two width measurements, which measurements are taken generally transverse to each other.

In an aspect of the first embodiment, the body includes a first major surface on which the sensing region is located and a second major surface, wherein the first major surface is at least slightly convex.

In an aspect of the first embodiment, a reference plane may be defined that touches the first major surface at a point spaced in from edges of the first major surface, and is generally parallel to the first major surface, and is spaced away from opposite edges of the first major surface due to convexity of the first major surface, and wherein a location of an edge is the point at which a congruent line or a normal line is angled 45 degrees with respect to the reference plane.

In an aspect of the first embodiment, the reference plane is spaced from the edges a distance that is at least about 3% from the edges, and not more than 50% of the width.

In an aspect of the first embodiment, the reference plane is spaced from the edges a distance that is at least about 3% from the edges, and not more than 25% of the width.

In an aspect of the first embodiment, the reference plane is spaced from the edges a distance that is at least about 3% from the edges, and not more than 15% of the width.

In an aspect of the first embodiment, the body includes a first major surface on which the sensing region is located, and wherein edges of the first major surface are rounded and transition smoothly away from the first major surface.

In an aspect of the first embodiment, the body defines a surface area, and wherein between 10 % and 100% of the surface area is convexly curved.

In an aspect of the first embodiment, the body defines a surface area, and wherein a substantial portion of the surface area is convexly curved.

In an aspect of the first embodiment, the body defines a surface area, and where at least about 90 % of the surface area is convexly curved.

In an aspect of the first embodiment, the body includes plastic.

In an aspect of the first embodiment, the plastic is selected from the group consisting of thermoplastic and thermoset.

In an aspect of the first embodiment, the thermoset is epoxy.

In an aspect of the first embodiment, the thermoset is silicone.

In an aspect of the first embodiment, the thermoset is polyurethane.

In an aspect of the first embodiment, the plastic is selected from the group consisting of metal, ceramic, and glass.

In an aspect of the first embodiment, a porous biointerface material that covers at least a portion of the sensing region.

In an aspect of the first embodiment, the biointerface material includes interconnected cavities dimensioned and arranged to create contractile forces that counteract with the generally uniform downward fibrous tissue contracture caused by the foreign body capsule in vivo and thereby interfere with formation of occlusive cells.

In an aspect of the first embodiment, the sensor is a glucose sensor.

In a second embodiment, an implantable sensor is provided for use in measuring a concentration of an analyte in a bodily fluid, the sensor including: a body including a sensing region on a major surface of the body, wherein the major surface includes a continuous curvature substantially across the entire surface such that when a foreign body capsule forms around the sensor, a contractile force is exerted by the foreign body capsule toward the sensing region.

In a third embodiment, a wholly implantable sensor is provided to measure a concentration of an analyte in a bodily fluid, including: a wholly implantable body including a sensing region adapted for transport of analytes between the sensor and the bodily fluid, wherein the sensing region is located on a curved portion of a first surface of the body and wherein the first surface includes anchoring material thereon for supporting tissue ingrowth.

In a fourth embodiment, an implantable sensor is provided to measure a concentration of an analyte in a bodily fluid, including: a body having a first major surface and, opposite thereto, a second major surface, wherein the first major surface is generally planar, slightly convex, and has rounded edges, with a sensor region located on the first major surface that is spaced away from the rounded edges, wherein the first major surface is sufficiently convex that when a foreign body capsule forms around the sensor, contractile forces are exerted thereby generally uniformly towards the sensing region.

In a fifth embodiment, an implantable sensor is provided for use in measuring a concentration of an analyte in a bodily fluid, the sensor including: a body, the body including a sensing region adapted for transport of analytes between the sensor and the bodily fluid, wherein the sensing region is located on a curved portion of the body, and wherein a thermoset material substantially encapsulates the body outside the sensing region.

In a sixth embodiment, an implantable sensor for use in measuring a concentration of an analyte in a bodily fluid, the sensor including: sensing means for measuring a concentration of analyte in a bodily fluid; and housing means for supporting the sensing means, wherein the sensing means is located on a curved portion of housing means such that when a foreign body capsule forms around the housing means, a contractile force is exerted by the foreign body capsule toward the sensing means.

In a seventh embodiment, an implantable drug delivery device is provided that allows transport of analytes between the device and a bodily fluid, the device including: a body including an analyte transport region adapted for transport of analytes between the device and the bodily fluid, wherein the transport region is located on a curved portion of the body such that when a foreign body capsule forms around the device, a contractile force is exerted by the foreign body capsule toward the analyte transport region.

In an eighth embodiment, an implantable cell transplantation device is provided that allows transport of analytes between the device and a bodily fluid, the device including: a body including an analyte transport region adapted for transport of analytes between the device and the bodily fluid, wherein the transport region is located on a curved portion of the body such that when a foreign body capsule forms around the device, a contractile force is exerted by the foreign body capsule toward the analyte transport region.

BRIEF DESCRIPTION OF THE DRAWINGS

FIGS. 10A and 10C are views of the sensor with the sensing body in a collapsed state, FIGS. 10B and 10D are views of the sensor with the sensing body in an expanded state.

13B is a side schematic view of an analyte sensor with anchoring material on a first major surface on which the sensing region is located, and wherein a second major surface is substantially smooth.

Figure 14A:
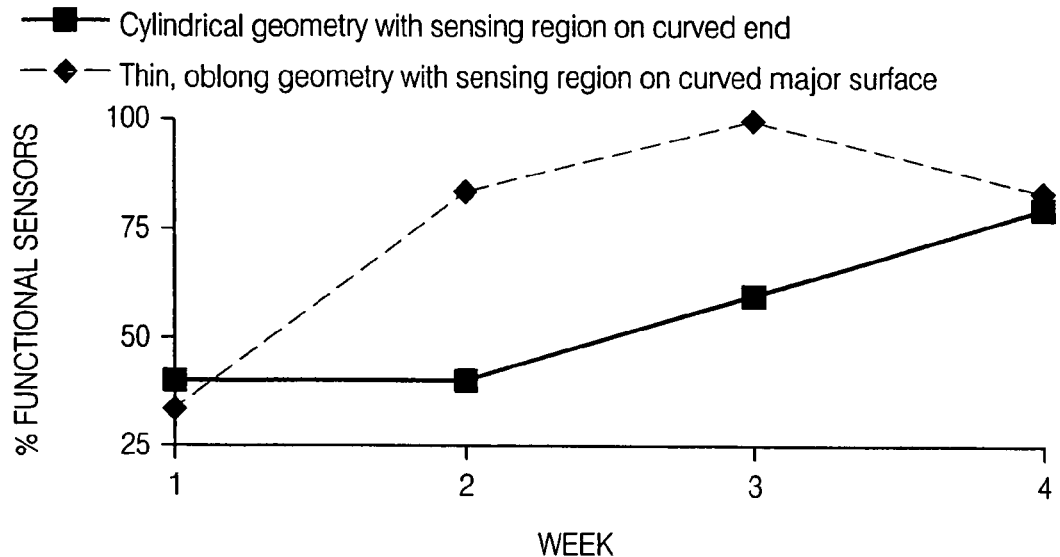

FIG. 14A is a graph showing the percentage of functional sensors from a study of two different sensor geometries implanted in a host.

Figure 14B:
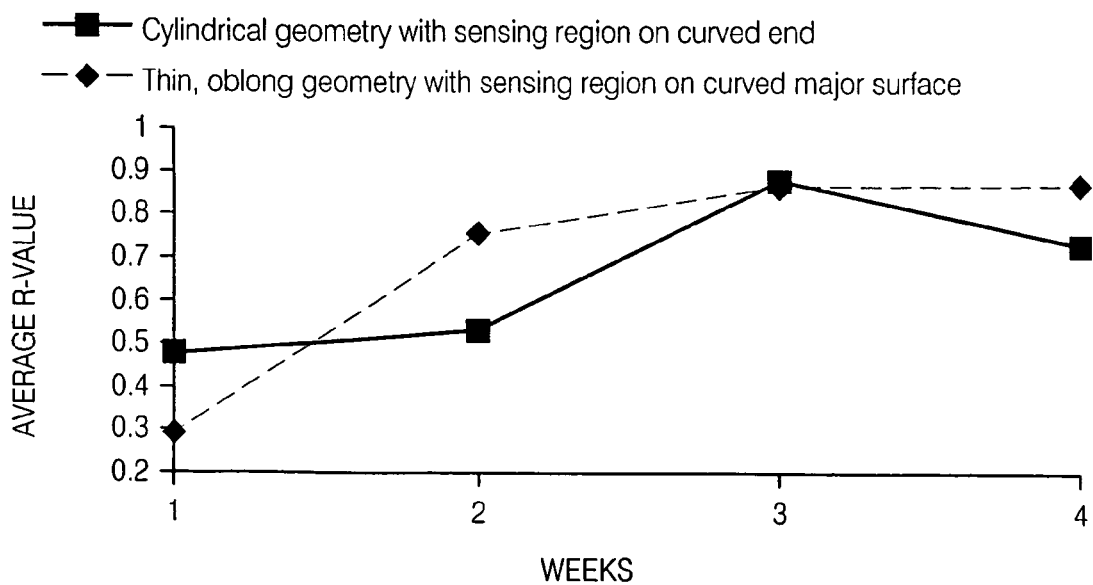

FIG. 14B is a graph showing the average R-value of sensors from a study of two different sensor geometries implanted in a host.

DETAILED DESCRIPTION OF THE PREFERRED EMBODIMENT

The following description and examples illustrate some exemplary embodiments of the disclosed invention in detail. Those of skill in the art will recognize that there are numerous variations and modifications of this invention that are encompassed by its scope. Accordingly, the description of a certain exemplary embodiment should not be deemed to limit the scope of the present invention.

Definitions

In order to facilitate an understanding of the disclosed invention, a number of terms are defined below.

The term "analyte," as used herein, is a broad term and is used in its ordinary sense, including, without limitation, to refer to a substance or chemical constituent in a biological fluid (for example, blood, interstitial fluid, cerebral spinal fluid, lymph fluid or urine) that can be analyzed. Analytes may include naturally occurring substances, artificial substances, metabolites, and/or reaction products. In some embodiments, the analyte for measurement by the sensor heads, devices, and methods is glucose. However, other analytes are contemplated as well, including but not limited to acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carbon dioxide; carnitine; carnosinase; CD4; ceruloplasmin; chenodeoxycholic acid; chloroquine; cholesterol; cholinesterase; conjugated 1-β hydroxy-cholic acid; cortisol; creatine kinase; creatine kinase MM isoenzyme; cyclosporin A; d-penicillamine; de-ethyl-chloroquine; dehydroepiandrosterone sulfate; DNA (acetylator polymorphism, alcohol dehydrogenase, alpha 1-antitrypsin, cystic fibrosis, Duchenne/Becker muscular dystrophy, glucose-6-phosphate dehydrogenase, hemoglobinopathies, A,S,C,E, D-Punjab, beta-thalassemia, hepatitis B virus, HCMV, HIV-1, HTLV-1, Leber hereditary optic neuropathy, MCAD, RNA, PKU, *Plasmodium vivax*, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free β-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; glucose-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17 alpha-hydroxyprogesterone; hypoxanthine phosphoribosyl transferase; immunoreactive trypsin; lactate; lead; lipoproteins ((a), B/A-1, β); lysozyme; mefloquine; netilmicin; oxygen; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis, Echinococcus granulosus, Entamoeba histolytica*, enterovirus, *Giardia duodenalisa, Helicobacter pylori*, hepatitis B virus, herpes virus, HIV-1, IgE (atopic disease), influenza virus, *Leishmania donovani*, leptospira, measles/mumps/rubella, *Mycobacterium leprae, Mycoplasma pneumoniae, Myoglobin, Onchocerca volvulus*, parainfluenza virus, *Plasmodium falciparum*, poliovirus, *Pseudomonas aeruginosa*, pH, respiratory syncytial virus, rickettsia (scrub typhus), *Schistosoma mansoni, Toxoplasma gondii, Trepenoma pallidium, Trypanosoma cruzi*/rangeli, vesicular stomatis virus, *Wuchereria bancrofti*, yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin. Salts, sugar, protein, fat, vitamins and hormones naturally occurring in blood or interstitial fluids may also constitute analytes in certain embodiments. The analyte may be naturally present in the biological fluid, for example, a metabolic product, a hormone, an antigen, an antibody, and the like. Alternatively, the analyte may be introduced into the body, for example, a contrast agent for imaging, a radioisotope, a chemical agent, a fluorocarbon-based synthetic blood, or a drug or pharmaceutical composition, including but not limited to insulin; ethanol; cannabis (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbituates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body may also be analyzed, such as, for example, ascorbic acid, uric acid, dopamine, noradrenaline, 3-methoxytyramine (3MT), 3,4-Dihydroxyphenylacetic acid (DOPAC), Homovanillic acid (HVA), 5-Hydroxytryptamine (5HT), and 5-Hydroxyindoleacetic acid (FHIAA).

By the terms "evaluated", "monitored", "analyzed", and the like, it is meant that an analyte may be detected and/or measured.

The terms "sensor head" and "sensing region" as used herein are broad terms and are used in their ordinary sense, including, without limitation, the region of a monitoring device responsible for the detection of a particular analyte. In one embodiment, the sensing region generally comprises a non-conductive body, a working electrode (anode), a reference electrode, and a counter electrode (cathode) passing through and secured within the body forming an electrochemically reactive surface at one location on the body and an electronic connective means at another location on the body, and a multi-region membrane affixed to the body and covering the electrochemically reactive surface. The counter electrode generally has a greater electrochemically reactive surface area than the working electrode. During general operation of the sensor a biological sample (for example, blood or interstitial fluid) or a portion thereof contacts (directly or after passage through one or more membranes or domains) an enzyme (for example, glucose oxidase); the reaction of the biological sample (or portion thereof) results in the formation of reaction products that allow a determination of the analyte (e.g., glucose) level in the biological sample. In preferred embodiments, the multi-region membrane further comprises an enzyme domain and an electrolyte phase, namely, a free-flowing liquid phase comprising an electrolyte-containing fluid described further below. While the preferred embodiments are generally illustrated by a sensor as described above, other sensor head configurations are also contemplated. While electrochemical sensors (including coulometric, voltammetric, and/or amperometric sensors) for the analysis of glucose are generally contemplated, other sensing mechanisms, including but not limited to optochemical sensors, biochemical sensors, electrocatalytic sensors, optical sensors, piezoelectric sensors, thermoelectric sensors, and acoustic sensors may be used. A device may include one sensing region, or multiple sensing regions. Each sensing region can be employed to determine the same or different analytes. The sensor region may include the entire surface of the device, a substantial portion of the surface of the device, or only a small portion of the surface of the device. Different sensing mechanisms may be employed by different sensor regions on the same device, or a device may include one or more sensor regions and also one or more regions for drug delivery, immunoisolation, cell transplantation, and the like. It may be noted that the preferred embodiments, the "sensor head" is the part of the sensor that houses the electrodes, while the "sensing region" includes the sensor head and area that surrounds the sensor head, particularly the area in such proximity to the sensor head that effects of the foreign body capsule on the sensor head.

The term "foreign body capsule" or "FBC," as used herein, is a broad term and is used in its ordinary sense, including, without limitation, body's response to the introduction of a foreign object; there are three main layers of a FBC: 1) the innermost layer, adjacent to the object, is composed generally of macrophages, foreign body giant cells, and occlusive cell layers; 2) the intermediate FBC layer, lying distal to the first layer with respect to the object, is a wide zone (e.g., about 30-100 microns) composed primarily of fibroblasts, contractile fibrous tissue fibrous matrix; and 3) the outermost FBC layer is loose connective granular tissue containing new blood vessels. Over time, this FBC tissue becomes muscular in nature and contracts around the foreign object so that the object remains tightly encapsulated.

The term "subcutaneous," as used herein, is a broad term and is used in its ordinary sense, including, without limitation, under the skin.

The term "intramuscular," as used herein, is a broad term and is used in its ordinary sense, including, without limitation, within the substance of a muscle.

The term "intraperitoneal," as used herein, is a broad term and is used in its ordinary sense, including, without limitation, within the peritoneal cavity, which is the area that contains the abdominal organs.

The term "intrafascial," as used herein, is a broad term and is used in its ordinary sense, including, without limitation, within the fascia, which is a sheet or band of fibrous tissue such as lies deep to the skin or forms an investment for muscles and various other organs of the body.

The term "axillary region," as used herein, is a broad term and is used in its ordinary sense, including, without limitation, the pyramidal region between the upper thoracic wall and the arm, its base formed by the skin and apex bounded by the approximation of the clavicle, coracoid process, and first rib; it contains axillary vessels, the brachial plexus of nerves, many lymph nodes and vessels, and loose areolar tissue.

The term "apex," as used herein, is a broad term and is used in its ordinary sense, including, without limitation, the uppermost point; for example the outermost point of a convexly curved portion.

The term "cuboidal," as used herein, is a broad term and is used in its ordinary sense, including, without limitation, a polyhedron composed of six faces, eight vertices, and twelve edges, wherein the faces.

The term "convex," as used herein, is a broad term and is used in its ordinary sense, including, without limitation, outwardly protuberant; that is, an object is convex if for any pair of points within the object, any point on the line that joins them is also within the object. A convex portion is a portion of an object that is convex in that portion of the object. For example, a solid cube is convex, but anything that is hollow or has a dent in it is not convex.

The term "curvature," "curved portion," and "curved," as used herein, are broad terms and is used in their ordinary sense, including, without limitation, one or more arcs defined by one or more radii.

The term "cylindrical," as used herein, is a broad term and is used in its ordinary sense, including, without limitation, a solid of circular or elliptical cross section in which the centers of the circles or ellipses all lie on a single line. A cylinder defines a lateral surface and two ends.

The term "ellipsoidal," as used herein, is a broad term and is used in its ordinary sense, including, without limitation, closed surface of which all plane sections are either ellipses or circles. An ellipsoid is symmetrical about three mutually perpendicular axes that intersect at the center.

The term "spherical," as used herein, is a broad term and is used in its ordinary sense, including, without limitation, a solid that is bounded by a surface consisting of all points at a given distance from a point constituting its center.

The term "anchoring material," as used herein, is a broad term and is used in its ordinary sense, including, without limitation, biocompatible material that is non-smooth, and particularly comprises an architecture that supports tissue ingrowth in order to facilitate anchoring of the material into bodily tissue in vivo. Some examples of anchoring materials include polyester, polypropylene cloth, polytetrafluoroethylene felts, expanded polytetrafluoroethylene, and porous silicone, for example.

The term "mechanical anchoring mechanism," as used herein, is a broad term and is used in its ordinary sense, including, without limitation, mechanical mechanisms (e.g., prongs, spines, barbs, wings, hooks, helical surface topography, gradually changing diameter, or the like), which aids in immobilizing the sensor in the subcutaneous space, particularly prior to formation of a mature foreign body capsule The term "biocompatible," as used herein, is a broad term and is used in its ordinary sense, including, without limitation, compatibility with living tissue or a living system by not being toxic.

The term "non-adhesive to tissue," as used herein, is a broad term and is used in its ordinary sense, including, without limitation, a material or surface of a material to which cells and/or cell processes do not adhere at the molecular level, and/or to which cells and/or cell processes do not adhere to the surface of the material.

The term "plastic," as used herein, is a broad term and is used in its ordinary sense, including, without limitation, polymeric materials that have the capability of being molded or shaped, usually by the application of heat and pressure. Polymers that are classified as plastics can be divided into two major categories: thermoplastic and thermoset.

The term "thermoplastic," as used herein, is a broad term and is used in its ordinary sense, including, without limitation, polymeric materials such as polyethylene and polystyrene that are capable of being molded and remolded repeatedly. The polymer structure associated with thermoplastics is that of individual molecules that are separate from one another and flow past one another.

The term "thermoset," as used herein, is a broad term and is used in its ordinary sense, including, without limitation, polymeric materials such as epoxy, silicone, and polyurethane that cannot be reprocessed upon reheating. During their initial processing, thermosetting resins undergo a chemical reaction that results in an infusible, insoluble network. Essentially, the entire heated, finished article becomes one large molecule. For example, the epoxy polymer undergoes a cross-linking reaction when it is molded at a high temperature. Subsequent application of heat does not soften the material to the point where it can be reworked and indeed may serve only to break it down.

The term "substantially," as used herein, is a broad term and is used in its ordinary sense, including, without limitation, refers to an amount greater than 50 percent, preferably greater than 75 percent and, most preferably, greater than 90 percent.

The term "host," as used herein is a broad term and is used in its ordinary sense, including, without limitation, both humans and animals.

The term "R-value," as used herein, is a broad term and is used in its ordinary sense, including, without limitation, one conventional way of summarizing the correlation of data; that is, a statement of what residuals (e.g., root mean square deviations) are to be expected if the data are fitted to a straight line by the a regression.

Overview

In a preferred embodiment, the sensor heads, devices, and methods of the preferred embodiments may be used to determine the level of glucose or other analytes in a host. The level of glucose is a particularly important measurement for individuals having diabetes in that effective treatment depends on the accuracy of this measurement.

Although the description that follows is primarily directed at implantable glucose sensors, the methods of the preferred embodiments are not limited to either electrochemical sensing or glucose measurement. Rather, the methods may be applied to any implantable sensor that detects and quantifies an analyte present in biological fluids (including, but not limited to, amino acids and lactate), including those analytes that are substrates for oxidase enzymes (see, e.g., U.S. Pat. No. 4,703,756 to Gough et al., hereby incorporated by reference), as well as to implantable sensors that detect and quantify analytes present in biological fluids by analytical methods other than electrochemical methods, as described above. The methods may also offer benefits and be suitable for use with implantable devices, other than sensors, that are concerned with the transport of analytes, for example, drug delivery devices, cell transplantation devices, tracking devices, or any other foreign body implanted subcutaneously or in other soft tissue of the body, for example, intramuscular, intraperitoneal, intrafascial, or in the axial region.

Methods and devices that may be suitable for use in conjunction with aspects of the preferred embodiments are disclosed in copending applications including U.S. application Ser. No. 09/916,386 filed Jul. 27, 2001 and entitled "MEMBRANE FOR USE WITH IMPLANTABLE DEVICES"; U.S. application Ser. No. 09/916,711 filed Jul. 27, 2001 and entitled "SENSOR HEAD FOR USE WITH IMPLANTABLE DEVICE"; U.S. application Ser. No. 09/447,227 filed Nov. 22, 1999 and entitled "DEVICE AND METHOD FOR DETERMINING ANALYTE LEVELS"; U.S. application Ser. No. 10/153,356 filed May 22, 2002 and entitled "TECHNIQUES TO IMPROVE POLYURETHANE MEMBRANES FOR IMPLANTABLE GLUCOSE SENSORS"; U.S. application Ser. No. 09/489,588 filed Jan. 21, 2000 and entitled "DEVICE AND METHOD FOR DETERMINING ANALYTE LEVELS"; U.S. application Ser. No. 09/636,369 filed Aug. 11, 2000 and entitled "SYSTEMS AND METHODS FOR REMOTE MONITORING AND MODULATION OF MEDICAL DEVICES"; and U.S. application Ser. No. 09/916,858 filed Jul. 27, 2001 and entitled "DEVICE AND METHOD FOR DETERMINING ANALYTE LEVELS," as well as issued patents including U.S. Pat. No. 6,001,067 issued Dec. 14, 1999 and entitled "DEVICE AND METHOD FOR DETERMINING ANALYTE LEVELS"; U.S. Pat. No. 4,994,167 issued Feb. 19, 1991 and entitled "BIOLOGICAL FLUID MEASURING DEVICE"; and U.S. Pat. No. 4,757,022 filed Jul. 12, 1988 and entitled "BIOLOGICAL FLUID MEASURING DEVICE." All of the above patents and patent applications are incorporated in their entirety herein by reference.

Such medical devices, including implanted analyte sensors, drug delivery devices and cell transplantation devices require close vascularization and transport of solutes across the device-tissue interface for proper function. These devices generally include a biointerface membrane, which encases the device or a portion of the device to prevent access by host inflammatory cells, immune cells, or soluble factors to sensitive regions of the device.

Nature of the Foreign Body Capsule

Biointerface membranes stimulate a local inflammatory response, called the foreign body response (FBR) that has long been recognized as limiting the function of implanted devices that require solute transport. The FBR has been well described in the literature.

Figure 1:
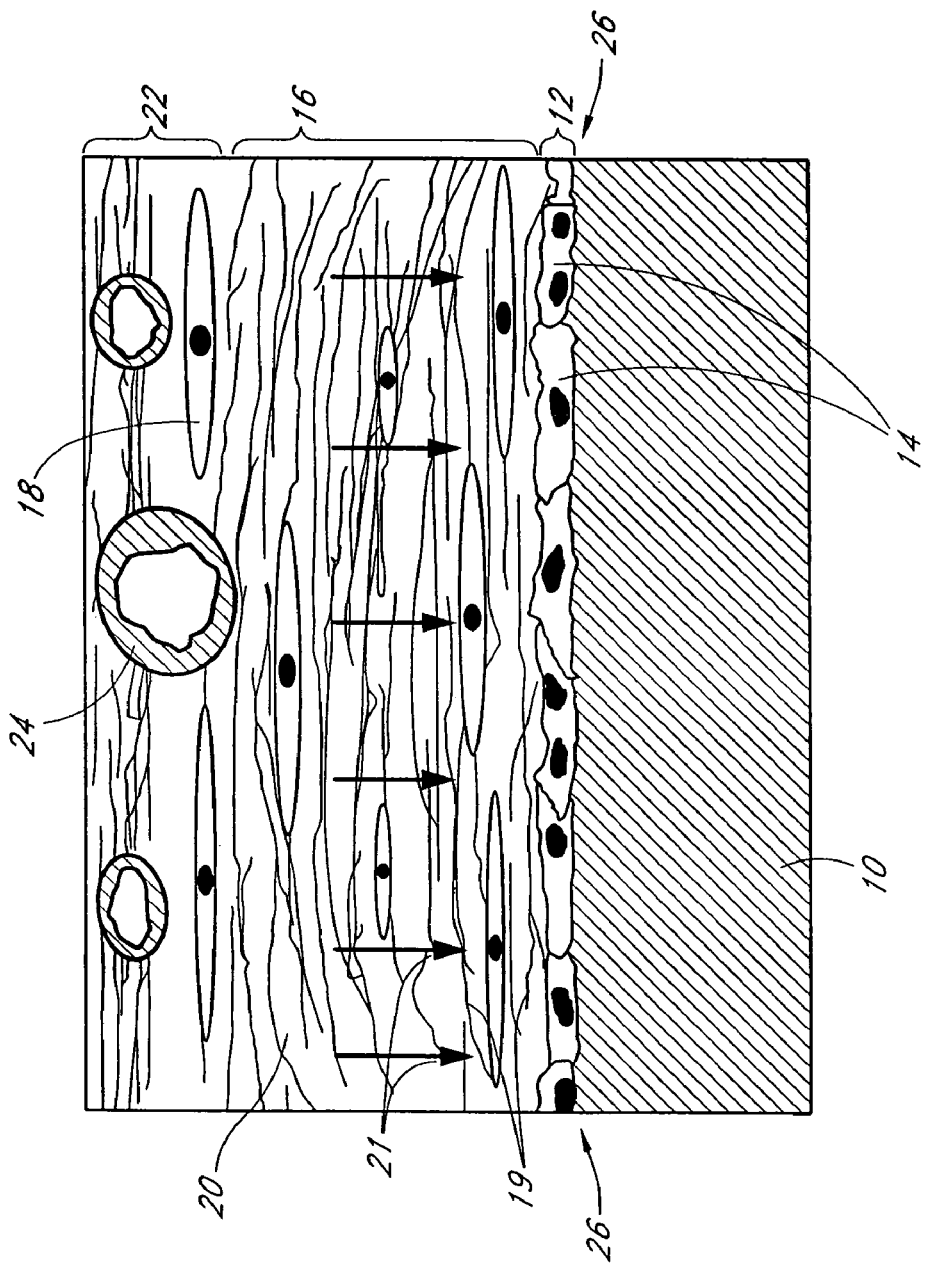
FIG. 1 is an illustration of classical foreign body response to an object implanted under the skin.

FIG. 1 is a schematic drawing that illustrates a classical foreign body response (FBR) to an object implanted under the skin. There are three main regions of a FBR. The innermost FBR region 12, adjacent to the device, is composed generally of macrophages and foreign body giant cells 14 (herein referred to as the barrier cell layer). These cells form a monolayer of closely opposed cells over the entire surface of a microscopically smooth, macroscopically smooth (but microscopically rough), or microporous (i.e., less than about 1 µm pore size) membrane. The intermediate FBR region 16 (herein referred to as the fibrous zone), lying distal to the first region with respect to the device, is a wide zone (about 30-1000 microns) composed primarily of fibroblasts 18, contractile fibrous tissue 19, and fibrous matrix 20 (shown as empty space, which is actually filled with this fibrous matrix). It may be noted that the organization of the fibrous zone, and particularly the contractile fibrous tissue 19, contributes to the formation of the monolayer of closely opposed cells due to the contractile forces 21 around the surface of the foreign body (e.g., membrane 10). The outermost FBR region 22 is loose connective granular tissue containing new blood vessels 24 (herein referred to as the vascular zone). Over time, the foreign body capsule becomes muscular due to differentiation of fibroblasts into myofibroblasts and contracts around the foreign body so that the foreign body remains tightly encapsulated.

Sensor Geometry

It has been observed that the variability of function observed in implanted sensors may sometimes occur in several different devices implanted within the same host (e.g., human or animal). Accordingly, this observation suggests that individual variability of hosts may not be a significant factor in the observed variability. Data suggest that a major factor in the variability is the individual nature of how the surrounding tissue heals around each device. Accordingly, the present invention discloses methods and systems for selecting an appropriate geometry for a device that requires transport of analytes in vivo, such that the healing of the host tissue around the device is optimized. Optimizing the host response includes minimizing variability, increasing transport of analytes, and controlling motion artifact in vivo, for example.

Figure 2A:
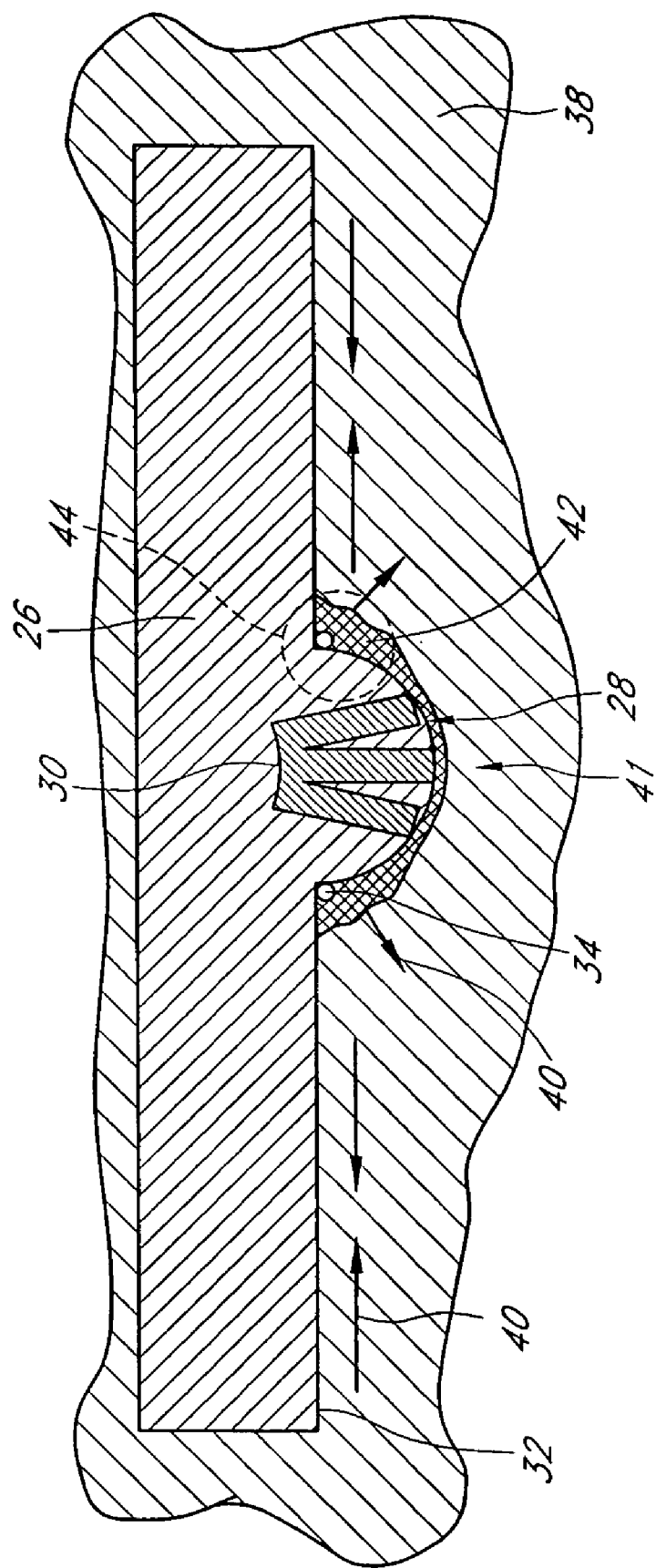
FIG. 2A is schematic side view of a prior art device that has a sensing region with an abrupt inside turn, causing a suboptimal foreign body response.
Figure 2B:
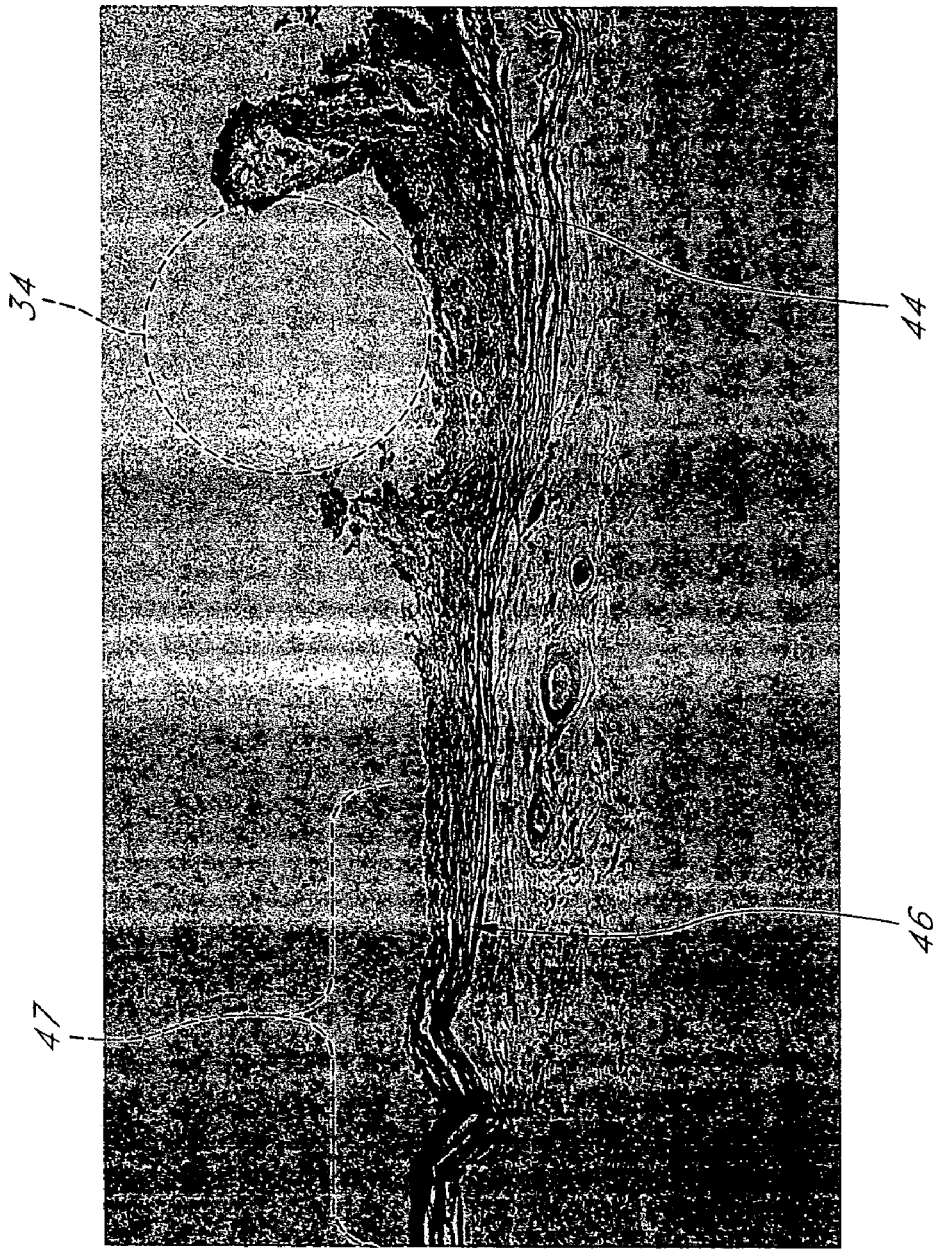
FIG. 2B is a photomicrograph of the foreign body response to a portion of the device of FIG. 2A, after formation of the foreign body capsule and subsequent explantation, showing thickened immune response adjacent to the abrupt inside turn.

FIG. 2A is schematic side view of a prior art device that has a sensing region with an abrupt inside turn, causing suboptimal foreign body response. FIG. 2B is a photomicrograph of the type of device of FIG. 2A after formation of the foreign body capsule and subsequent explantation, showing thickened host response adjacent the abrupt inside turn and lymphocytic infiltrate.

Particularly, FIG. 2A depicts a sensor 26 wherein a dome sensor head 28 incorporating the sensing electrodes 30 or other sensing devices or means protrudes above a large, flat surface 32 of the device. Particularly noteworthy is the abrupt change in curvature of an approximately 90-degree turn between the sensor head 28 and the flat surface 32. Additionally, an O-ring 34 encircles the device to hold a biointerface membrane (not shown) over the dome sensor head 28 of the device and causes further discontinuity of the surface between the sensor head and the flat surface of the sensor body.

A wide variability in the healing of the tissue adjacent to the sensor dome of the device is observed. Particularly, the foreign body capsule is thickest in the area 42 adjacent to the discontinuous surface (e.g., O-ring and sensor head-sensor body interface). This thickest portion is a result of tissue contracture that occurs during the foreign body response, resulting in forces being applied to the portion of the device interfacing with the tissue. Notably, because the device of FIG. 2A has an inside turn where the dome meets the top plate at the O-ring, the forces 40 exerted by contracture pull outwards, and thus away from the device-tissue interface. This causes inflammation in the region of the inside turn. Greater tissue trauma and the formation of barrier cell layers are typically observed adjacent to the region of the device wherein the dome meets the top plate. It is believed that outward forces produced by tissue contraction cause wounding in this site, which stimulates higher levels of inflammation, resulting in occlusion. It should be noted that this more "turbulent area" 42 is marked by an increase chronic inflammatory response which is most occlusive at the discontinuous surface are, but spreads to include the thickening in sensing area 41 that may effect the transport of analytes and thus the function of the sensor in vivo.

FIG. 2B is a photomicrograph of the foreign body capsule, after a device having the sensor configuration of FIG. 2A was explanted from a host. The right side of the photomicrograph shows a thickening of the tissue response with inflammatory cells present near the inside turn (within 44). The o-ring 34 was located approximately as shown by the dashed line, which contributed to the thickening of the tissue response due to the abruptness of the surface area. It may be noted that the tissue response thins near the center of the dome (at 46 (the fold in the section near the center of the dome is an artifact of sample preparation)). The electrodes are located within the sensing region 47 as shown on the photomicrograph, over which occlusive cells extend from the thickened response 44. That is, the thickening of the tissues in the "turbulent area", which is the area adjacent to the discontinuous surfaces at the inside turn, leads to the subsequent formation of barrier cell layers that may continue over the sensor head and block the transport of analytes across the device-tissue interface over time. The nature of the response suggests that trauma to the tissue may have occurred during or after the initial wound healing. If trauma occurs during wound healing, complete healing never occurs and the tissue stays in a hyper-inflammatory state during the entire course of the implant period. Alternatively, if trauma occurs subsequent to the initial wound healing, the wound heals but is re-injured, perhaps repeatedly, over time. Either of these trauma-induced wounding mechanisms may lead to improper healing and the growth of occlusive cells at the biointerface. It may be noted that it is the combination of the severity of the inside turn and its proximity to the sensing region that forms the occlusive cell layer, which may cause blockage of analyte transport to the sensor. In some alternative embodiments, certain turns (e.g., inside turns or otherwise) on the surface of the sensor body may not adversely effect the transport of analytes; for example, turns that are located at a sufficient distance from the sensing region may not produce a thickened inflammatory host response adjacent the sensing region and/or turns that are sufficiently gradual and/or lack abruptness may not adversely effect the host response adjacent the sensing regions.

The tissue response resulting in the growth of occlusive cells as described above tends to occur due to the contraction of the surrounding wound tissue. It is therefore desirable to ensure stable wound healing that does not change after the initial healing. As illustrated by the photomicrograph of FIG. 2B, the geometry of the device depicted does not favor stable healing because tissue contracture results in the pulling away of tissues from the device surface at the junction between the dome and top plate.

Figure 3A:
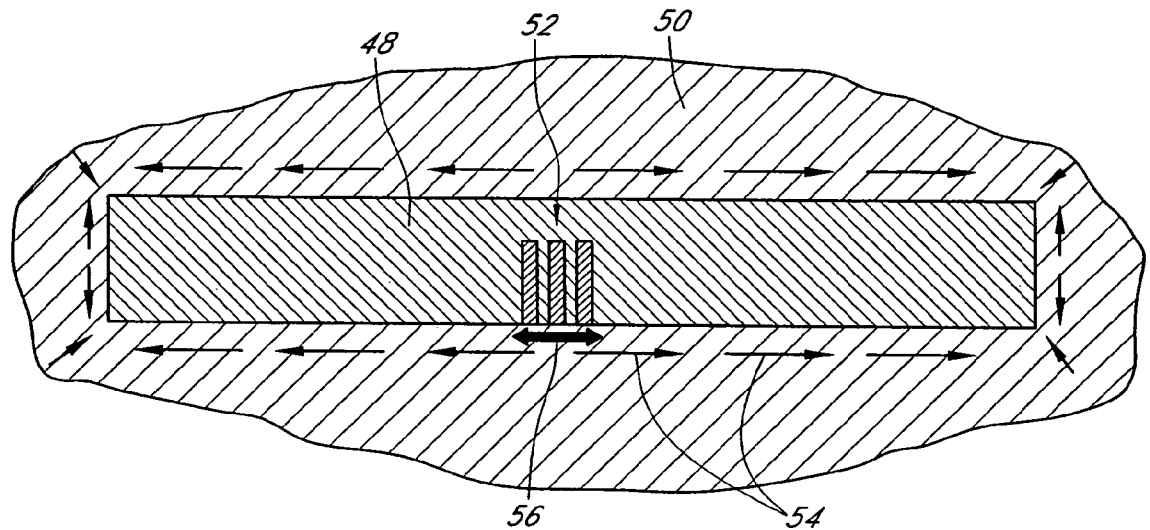
FIG. 3A is a schematic side view of another prior art device that has flattened surfaces across the entire device, and particularly across the sensing region, causing sub-optimal foreign body capsule healing.

FIG. 3A is a schematic side view of another prior art device that has flattened surfaces across the entire device, and particularly across the sensing region, creating sub-optimal foreign body capsule healing. In the sensor of FIG. 3A, all surfaces are flat and all edges and corners are sharp; there is no curvature or convexity, particularly in the sensing region. Consequently, contractile forces 54 pull laterally and outwardly along the flat surfaces, including the sensing region, which is the area proximal to the electrodes 52, as the FBC tightens around the device. Lateral contractile forces 54 caused by the FBC 50 along the flat surfaces are believed increase motion artifact and tissue damage due to shear forces 56 between the device 52 and the tissue. In other words, rather than firmly holding the tissue adjacent the sensing region with a downward force against the sensing region (such as will be shown with the geometry of the present invention), a lateral movement (indicated by arrow 56) is seen in the tissue adjacent to the sensing region, causing trauma-induced wounding mechanisms that may lead to improper healing and the growth of occlusive cells at the biointerface. This is especially harmful in the sensing region, which requires substantially consistent transport of analytes, because it is known that thickening of the FBC from chronic inflammation and occlusive cells decreases or blocks analyte transport to the device.

It may be noted that some prior art devices attempt to minimize tissue trauma by rounding edges and corners, however the effects of tissue trauma will still be seen in the flat surfaces (e.g., sensing region) of the device such as described above, thereby at least partially precluding function of a device requiring analyte transport. Similarly, placement of the sensing region, or a plurality of sensing regions, away from the center of the device (such as seen in some prior art devices) would not significantly improve the effects of the lateral contractile forces along the flat surface of the sensing region(s), because it is the flat surface, whether at the center and/or off center, that causes in the occlusive tissue trauma in vivo.

It may be noted that the thickness of the FBC appears to increase around the central portion of the device and be thinner around the ends. It is believed that this phenomenon is due to the loose and counteracting lateral contractile forces near the center of the device, while a tighter contractile force near the ends of the device indicates tighter control of the FBC.

Figure 3B:
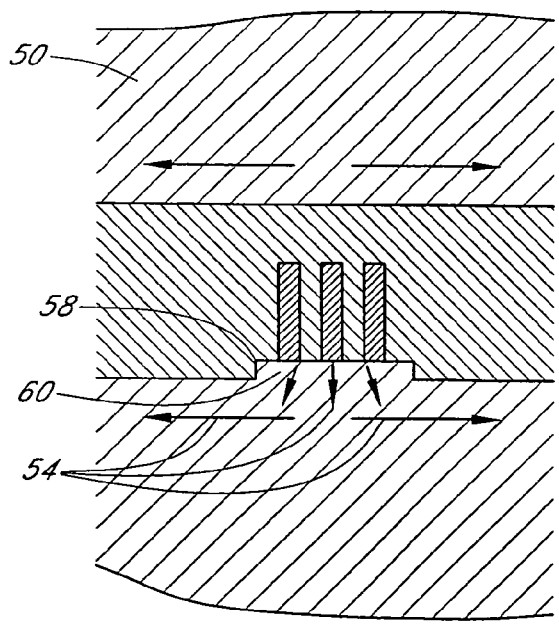
FIG. 3B is a schematic side view of the sensing region of yet another device that has flattened surfaces across the entire device, and an inset sensing region, which is an example of another device that causes sub-optimal foreign body capsule healing in implantable sensors.

FIG. 3B is a schematic side view of the sensing region of yet another prior art device that has flattened surfaces across the device, however includes an inset sensing region. The device of FIG. 3B is similar to the device of FIG. 3A, and is another example of a disadvantageous device due to suboptimal foreign body capsule healing. Particularly, the inset portion 58, whether bounded by sharp or rounded edges, will cause contractile forces 54 of the foreign body capsule to pull outwardly and laterally. The inset region of the device will experience increased trauma-induced wounding mechanisms that may lead to improper healing and the growth of occlusive cells at the biointerface as compared to FIG. 3A. In other words, both flat and inset (e.g., concave) sensing regions will cause tissue wounding and chronic inflammatory response leading to decreased transport of analytes, increased time lag, and decreased device function.

In contrast to the prior art, a preferred embodiment of the present invention provides a sensor geometry that includes a sensing region adapted for transport of analytes between the sensor and the bodily fluid, wherein the sensing region is located on a curved portion of the sensor body such that when a foreign body capsule forms around the sensor, a contractile force is exerted by the foreign body capsule toward the sensing region. This contractile force provides sufficient support to maintain the foreign body capsule in close proximity to the sensing region without substantial motion artifact or shearing forces, thereby minimizing inflammatory trauma, minimizing the thickness of the foreign body capsule, and maximizing the transport of analytes through the foreign body capsule. Additionally, the overall design described herein ensures more stable wound healing, and therefore better acceptance in the body.

It may be noted that the disadvantageous outward forces (e.g., forces 40 as described with reference to FIG. 2A, and forces 54 such as described with reference to FIG. 3B) refer to forces that cause motion of the foreign body capsule relative to the device as a whole. In other words, the discontinuity of the surface on which the sensing region is located creates outward forces of the FBC as a whole, which unfortunately allows motion of the device within the FBC. These outside forces 40 create a thickened FBC due to chronic inflammatory response responsive to motion of the device within the FBC such as described with reference to FIGS. 2 and 3. It may be noted however that a biointerface material with interconnected cavities in at least a portion thereof may be placed over the sensor head such as described with reference to copending U.S. patent application Ser. No. 10/647,065 filed Aug. 22, 2003 and entitled "POROUS MEMBRANE FOR USE WITH IMPLANTABLE DEVICES", which is incorporated herein in its entirety by reference. This biointerface material advantageously causes disruption of the contractile forces caused by the fibrous tissue of the FBC within the cavities of the biointerface material. Particularly, the biointerface material includes interconnected cavities with a multiple-cavity depth, which may affect the tissue contracture that typically occurs around a foreign body. That is, within the cavities of the biointerface material, forces from the foreign body response contract around the solid portions that define the cavities and away from the device. This architecture of the interconnected cavities of the biointerface material is advantageous because the contractile forces caused by the downward tissue contracture that may otherwise cause cells to flatten against the device and occlude the transport of analytes, is instead translated to and/or counteracted by the forces that contract around the solid portions (e.g., throughout the interconnected cavities) away from the device. Therefore, the mechanisms of the present invention (e.g., geometric configurations described herein) are designed to increase downward forces on the sensor head in order to decrease motion of the device relative to the FBC as a whole, which complements the mechanisms of the biointerface material that causes disruption of the contractile forces within the biointerface material in order to deflect the forces toward the solid portions within the biointerface and away from the device itself, both of which mechanisms work to prevent the formation of occlusive cells that block analyte transport. Therefore, a biointerface material such as described above may be placed over at least a portion (e.g., some or all) of the sensing region of the devices of the present invention to aid in preventing the formation of occlusive cells (e.g., barrier cell layer) and increasing the transport of analytes.

Figure 4:
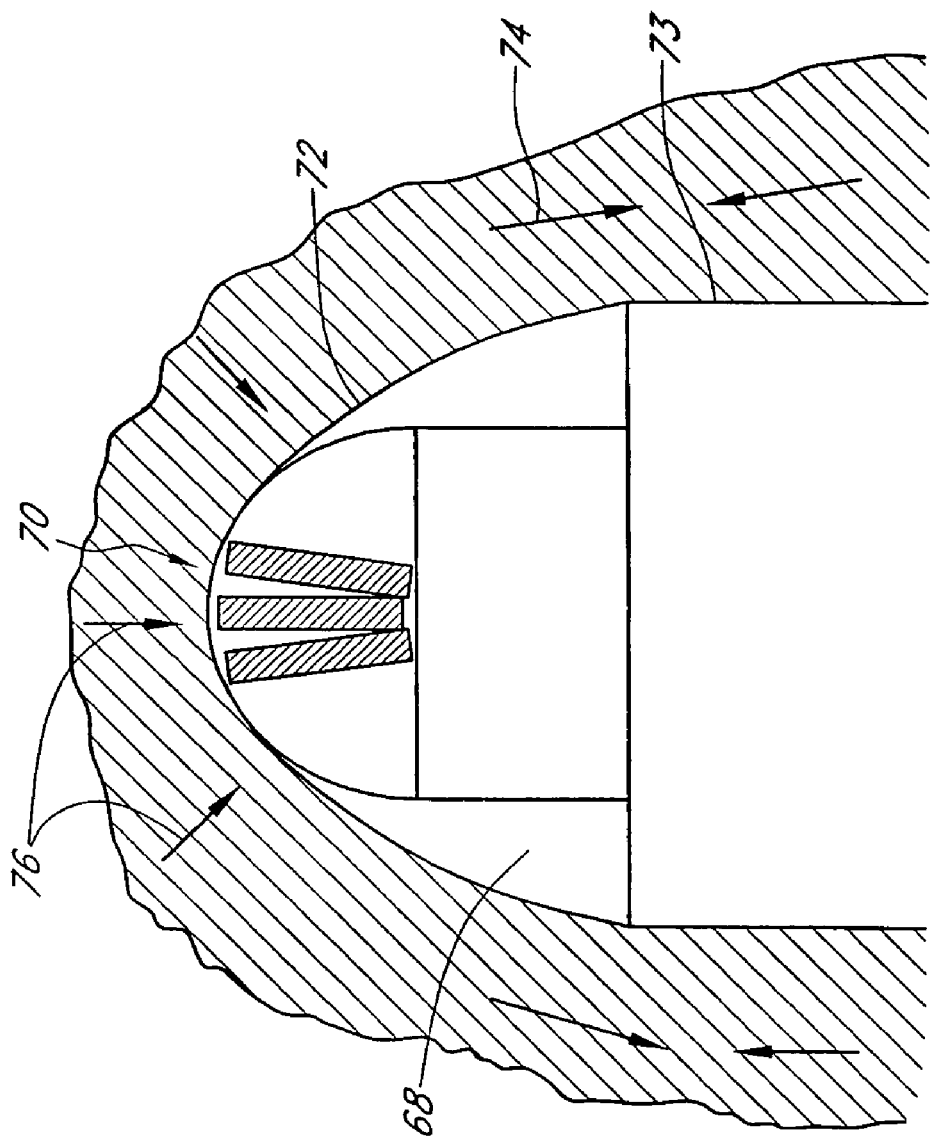
FIG. 4 is a cross-sectional view of the sensing region of an analyte sensor in one embodiment of the present invention, wherein the sensing region is continuously curved, thereby causing contractile forces from the foreign body capsule to press downwardly on the sensing region.

FIG. 4 is a cross-sectional view of the sensing region of an analyte sensor in one embodiment, wherein the sensing region is continuously curved, thereby causing contractile forces from the foreign body capsule to press downward thereon. The sensing region is located on an end of sensor that extends longitudinally (not shown). Particularly, the curved sensor region 70 includes no abrupt edges or discontinuous surfaces to ensure stable wound healing. For example, such a device 68 may be cylindrical with a collet that meets the head, as depicted in FIG. 4. The collet produces a continuous curvature from the sensor dome 72 to the wall of the cylinder 73. When this design is employed, tissue contracture (depicted by the arrows 74) results in forces oriented in towards the device interface along the entire surface of the dome (depicted by arrows 76). Thus, the foreign body capsule is pulled down against the surface of the device. Injury and re-injury is thereby minimized or even prevented because there are no outward forces produced by tissue contracture as in the design depicted in the devices of FIGS. 2 and 3. Improved biointerface healing is observed for this geometry, as evidenced by improved in vivo performance. A device with a design similar to that depicted in FIG. 4 was the subject of animal testing, which is described in more detail with reference to FIGS. 11A and 11B.

Figure 5A:
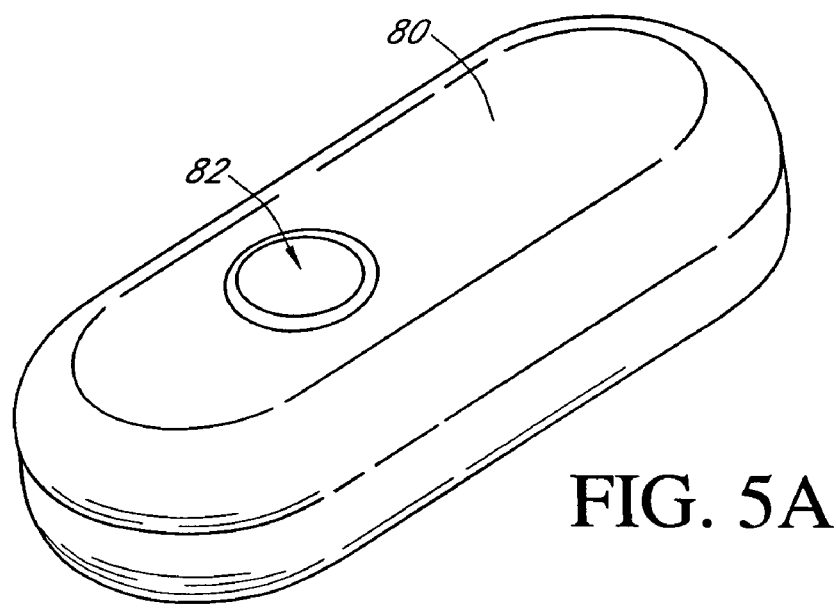
FIG. 5A is a perspective view of an analyte sensor in another embodiment, including a thin oblong body, a curved sensing region, and an overall curved surface on which the sensing region is located, thereby causing contractile forces from the foreign body capsule to press downward on the sensor head.
Figure 5B:
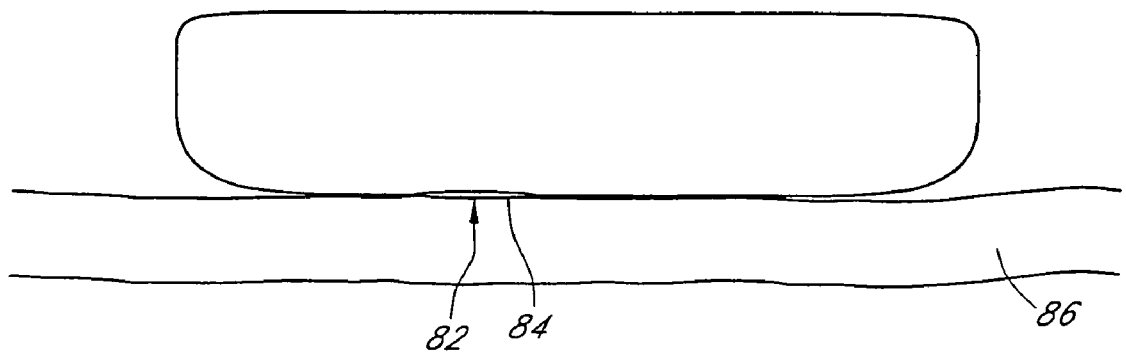
FIG. 5B is the analyte sensor of FIG. 5A shown implanted with the sensing region adjacent to the fascia underlying the subcutaneous space, and overlaying adjacent muscle.
Figure 5C:
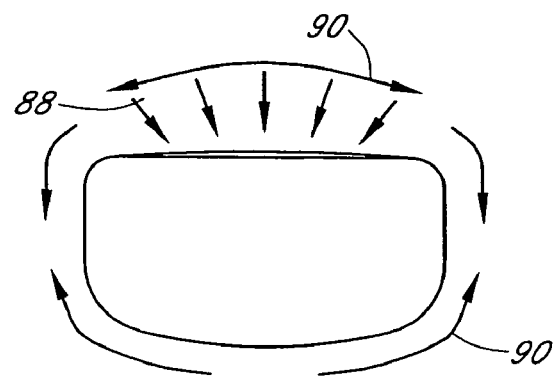
FIG. 5C is an end view of the analyte sensor of FIG. 5A showing the contractile forces caused by the foreign body capsule.
Figure 5D:
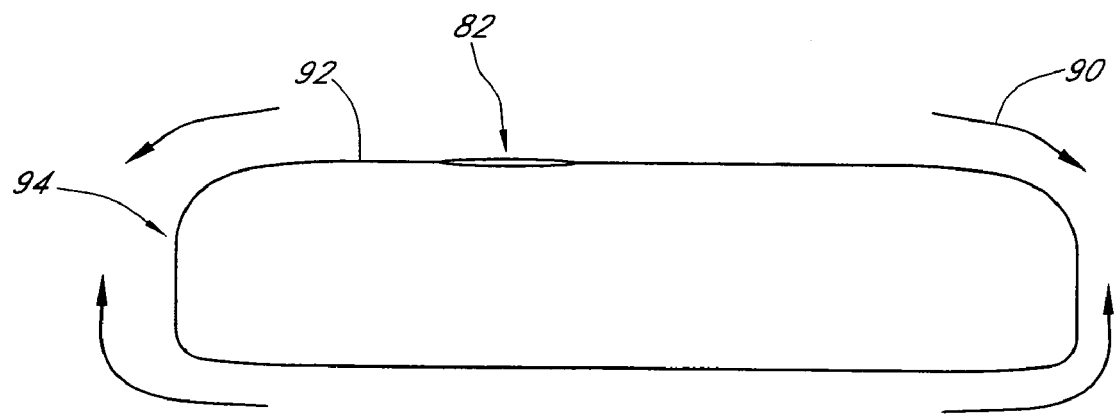
FIG. 5D is a side view of the analyte sensor of FIG. 5A.

FIG. 5A is a perspective view of an analyte sensor in another embodiment, including a thin ellipsoidal geometry, a curved sensing region, and an overall curved surface on which the sensing region is located, thereby causing contractile forces from the foreign body capsule to press downward on the sensor head. FIG. 5B is the analyte sensor of FIG. 5A shown implanted with the sensing region adjacent to the muscle fascia underlying the subcutaneous space. FIG. 5C is an end view of the analyte sensor of FIG. 5A showing the contractile forces that would be caused by a foreign body capsule. FIG. 5D is a side view of the analyte sensor of FIG. 5A.

In this embodiment, the analyte sensor 80 includes the sensing region 82 located on a curved portion of the sensor body, and including no abrupt edge or discontinuous surface in the proximity of the sensing region. Additionally, the overall curvature of the surface on which the sensing region is located, including rounded edges, invokes a generally uniform FBC around that surface, decreasing inflammatory response and increasing analyte transport at the device-tissue interface 84.

In one aspect of this embodiment, the sensor geometry particularly suited for healing at the device-tissue interface 84 when the sensor is implanted between two tissue planes. That is, the geometry includes a thin, substantially oval sensor, wherein the sensor head is positioned on one of the major surfaces of the sensor rather than at the tip, as illustrated in FIG. 4. When implanted, the sensor is oriented such that the sensor head is adjacent to the fascia underlying the subcutaneous space.

Perpendicular forces 88, depicted in FIG. 5C by arrows pointing down, reduce or eliminate shear forces with the tissue at the sensor head. While lateral forces 90 may appear to create shear forces at the sensor head, several features of the sensor mitigate these forces. For example, the sensor is much thinner and is immediately adjacent to the fascia, underlying the fat, making it less prone to movement. As another example, the sensor may be sutured to the tough fascia, which further prevents lateral forces from being conveyed to the sensor head; while in other preferred embodiments, an anchoring material or other method of attachment may be employed. As yet another example, in order to facilitate proper healing, the side of the sensor upon which the sensor head is situated preferably has a curved radius extending from lateral side to lateral side. As depicted in the side view and end view (FIGS. 5C and 5D), the sensor head is positioned at the apex of the radius. When surrounding tissue contracts as it heals, the radius serves to optimize the forces 88 exerted down onto the curved surface, especially the forces in the lateral directions 90, to keep the tissue uniformly in contact with the surface and to produce a thinner foreign body capsule. The curvature ensures that the head is resting against the tissue and that when tissue contraction occurs, forces are generated downward on the head so that the tissue attachment is maintained. It may be noted that the downward forces bring the tissue into contact with porous biointerface materials used for ingrowth-mediated attachment and for biointerface optimization, such as described above and in copending U.S. patent application Ser. No. 10/647,065 filed Aug. 22, 2003 and entitled "POROUS MEMBRANE FOR USE WITH IMPLANTABLE DEVICES". While it is preferable to have a curved radius extending longitudinally, in certain embodiments it may be acceptable to incorporate a longitudinally flat surface or longitudinal surface with another configuration. In a device as depicted in FIG. 5C, the radius of curvature in the lateral direction is preferably about 2.7 cm.

It may be noted that any curved surface can be deconvoluted to a series of radii, as is appreciated by one skilled in the art. It is generally preferred to have a radius of curvature in the lateral, longitudinal or other direction of from about 0.5 mm or less to about 10 cm or more. More preferably the radius of curvature is from about 1, 2, 3, 4, 5, 6, 7, 8, or 9 mm to about 5, 6, 7, 8, or 9 cm, even more preferably the radius of curvature is from about 1, 1.25, 1.5, 1.75, 2 or 2.25 cm to about 3, 3.25, 3.5, 3.75, 4, 4.25, 4.5, or 4.75 cm, and most preferably the radius of curvature is from about 2.5 or 2.6 cm to about 2.7, 2.8, or 2.9 cm. Radii of curvature in the longitudinal direction are generally preferred to be larger than those in the lateral direction. However, in certain embodiments the radii of curvature may be approximately the same, or smaller in the longitudinal direction.

In one embodiment, the preferred shape of the device can be defined in the context of a reference plane. In such an embodiment, the device has a first major surface and a second major surface opposite the first major surface, where the first major surface includes a sensor. The first and second major surfaces together preferably account for at least about 40% or 50% of the surface area of the device. The first major surface has edges between which a width of the first major surface can be measured, and the sensor is preferably spaced away from the edges by a distance that is at least about 10% of the width, and preferably at least about 15%, 20%, 25%, or 30% of the width of the first major surface. It is understood that the first major surface may have multiple edges and that multiple widths can be measured, and in the context of the foregoing, a width should be configured to run from one edge to an opposite edge. Preferably, spacing of the sensor from the edges specified above is true for at least two width measurements, which measurements are taken generally transverse to each other.

With the sensor situated on the first major surface of the device, a reference plane can be imagined that is congruent to the first major surface, which first major surface is preferably at least slightly convex. This plane, which would then touch the first major surface at a point spaced in from the edges of the first major surface, would be generally parallel to the first major surface and would additionally be spaced away from opposite edges of the first major surface due to the convex nature of the first major surface. In preferred embodiments, the reference plane would be spaced from the edges a distance that is at least about 3%, 4%, or 5% of the width between those edges, and more preferably 6%, 7%, 8% or more from the edges, but at the same time the distance is preferably not more than 50%, 40%, or 30% of the width, and may well be not more than 25%, 20%, or 15% of the width between the edges. In preferred embodiments, the edges of the first major surface are rounded, so that they transition smoothly away from the first major surface. In this situation, the location of the edge can be configured to be the point at which a congruent line and/or a normal line would be angled 45 degrees with respect to the reference plane.

In preferred embodiments, the sensor body defines a surface area, and wherein between 10% and 100% of the surface area is convexly curved. In some preferred embodiments a substantial portion of the surface area is convexly curved. In one preferred embodiment, at least about 90% of the surface area is convexly curved. In other preferred embodiments, 10, 20, 30, 40, 50, 60, 70, 80, 90, or 100% of the surface area is curved.

Figure 6:
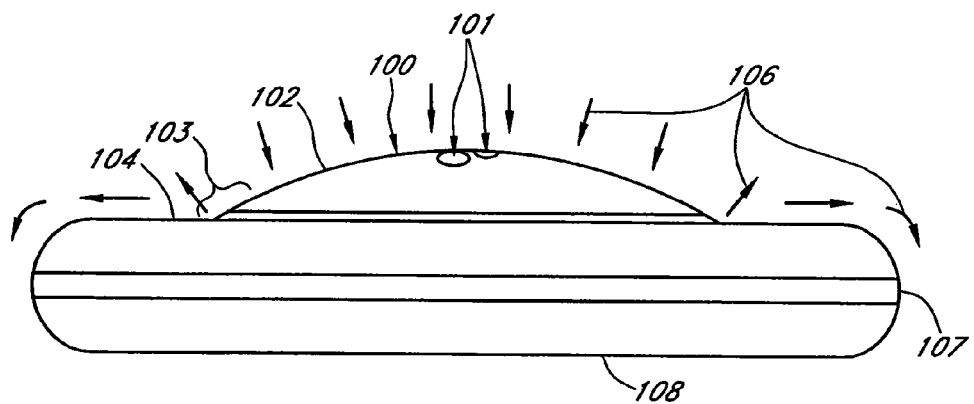
FIG. 6 is a perspective view of sensor geometry in an alternative environment wherein the sensor includes a curved sensor region and a flat region, wherein the interface between the flat region and the curved region includes a gradual transition.

FIG. 6 is a perspective view of a sensor geometry in an alternative embodiment wherein the sensor includes a curved sensor region and a flat region, wherein the interface between the flat region and the curved region includes a gradual transition. The implantable sensor includes a major surface 100 with a curved portion 102 on which the sensing region 101 is located and a flat portion 104 adjacent to the curved portion 102. Although the major surface is not entirely curved in this embodiment, the interface 103 between the curved and flat portions has a gradual transition and is located sufficiently distal from the sensing region 101 (where the transport of analytes is required) that any chronic inflammation caused by the turn at the interface 103 will not likely translate to the sensing region 101. In other words, the contractile forces 106 from a foreign body capsule that forms around the sensor in vivo will tend to contract toward the sensing region 101; although some outward and lateral forces are seen at the interface 103 and flat surface 104, they are spaced sufficiently far from the sensing region such that any chronic inflammatory response will not likely cover the sensing region 101 and block analyte transport. Anchoring material may cover some part or the majority of the major surface 100, may encircle the circumference of the sensor body 107, and/or may cover some part or the entire surface 108 opposite the sensing region, such as described in more detail elsewhere herein.

Figure 7:
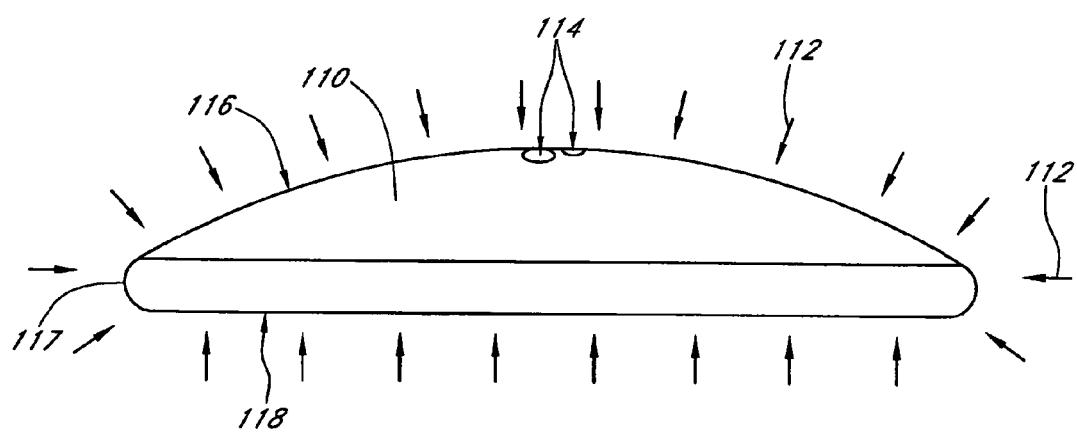
FIG. 7 is a perspective view of sensor geometry in an alternative embodiment wherein the entire sensor body is curved.

FIG. 7 is a perspective view of a sensor geometry in an alternative embodiment wherein the entire sensor body is curved. The implantable sensor has a curvature over the entire surface area of the sensor body 110. The curvature includes a variety of different radii at varying locations of the sensor body, and the contractile forces 112 from a FBC that forms around the sensor in vivo will tend to contract toward the entire sensor body 110, including the sensing region 114 on a first major side 116. Accordingly, this embodiment optimizes foreign body healing by minimizing the chronic inflammatory response that is otherwise caused by motion within the FBC. In other words, the FBC holds tightly to the sensor body 110 to provide optimal control (e.g., minimal motion) of the tissues around the sensor geometry, and particularly around the sensing region 112. It may be noted that the second major side 118 has a slight curvature that allows the entire sensor body to be curved. However in some embodiments, the second major side 118 can be designed flat rather than curved; in these embodiments, it may be noted that the sensing region is located on the side opposite the flat surface and there is no concavity therein or thereon. Anchoring material may cover some part or a majority of the first major side 116, may encircle the circumference of the sensor body 117, and/or may cover some part or the entire second major side 118 opposite the sensing region.

Figure 8:
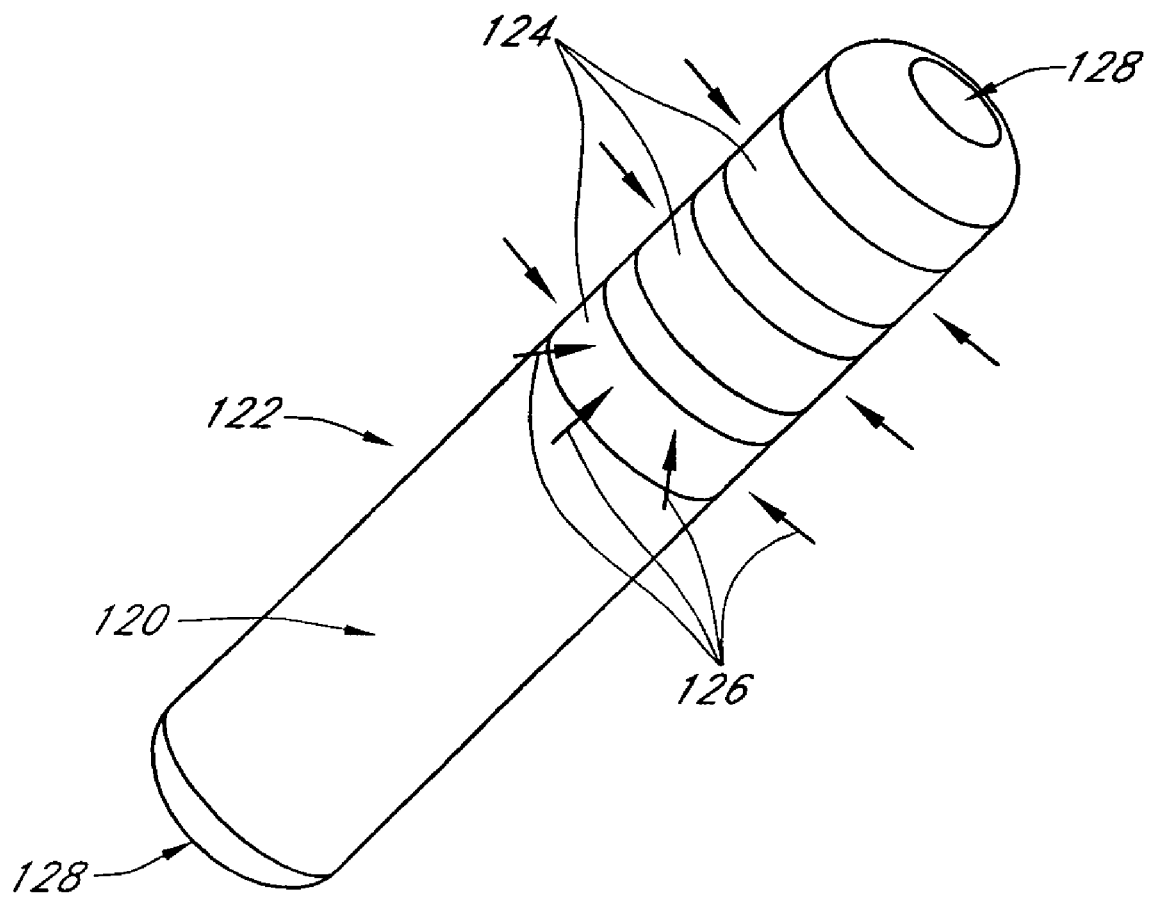
FIG. 8 is a perspective view of sensor geometry in an alternative embodiment including a cylindrical geometry wherein a plurality of sensing regions are located on the curved lateral surface of the sensor body.

FIG. 8 is a perspective view of a sensor 120 in an alternative embodiment including a cylindrical geometry wherein a plurality of sensors 124 are located on the curved lateral surface 122 of the sensor body. Anchoring material (not shown) may cover at least some of the non-electrode surface area of the cylindrical body. The sensor of this embodiment takes advantage of numerous features described herein, including, but not limited to, the following advantages.

As a first noted advantage, the cylindrical geometry of the sensor body 120 allows for discreet placement within or between tissue types when the overall surface area-to-volume ratio can be optimized to provide a maximal surface area with a minimal volume. That is, although the volume of a sensor often depends on the necessary electronics within the sensor body, the evolution of smaller batteries and circuit boards sanctions the design and manufacture of a cylindrical sensor with minimal volume; simultaneously, the surface area inherent in a cylindrical geometry allows for maximal tissue anchoring in vivo (e.g., as compared to a substantially rectangular or oval structure). In one exemplary embodiment, an application specific integrated circuit (ASIC) may be designed to fit within the geometric design of any of the embodiments disclosed herein to maximize the electronic capabilities while minimizing volume requirements as compared to conventional circuit boards. Sensor electronics requirements vary depend on the sensor type, however one example of electronics for a glucose sensor is described in more detail with reference to copending U.S. patent application Ser. No. 10/633,367 filed on Aug. 1, 2003 and entitled "SYSTEM AND METHODS FOR PROCESSING ANALYTE SENSOR DATA," which is incorporated by reference herein in its entirety.

As a second rioted advantage, the curved lateral surface 122 of the cylindrical structure lends itself to a plurality of sensing regions 124 (e.g., electrodes) and allows the sensor to sense a variety of different constituents (e.g., glucose, oxygen, interferants (e.g., ascorbate, urate, etc.)) using one compact sensor body.

As a third noted advantage, when the plurality of sensing regions 124 are configured to sense the same constituent (e.g., glucose) such as shown in FIG. 8, and are spread apart such as shown in FIG. 8, the likelihood of sensor location adjacent an area of the FBC that is optimized for transport of analytes is increased by the amount of increase of the area of the sensing regions 124. For example, inflammatory host response sometimes forms unevenly, therefore a distribution and increased surface area of sensing region(s) increases the likelihood of placement of the sensing region adjacent an area of minimum inflammatory host response and maximum transport of analytes to the sensor.

As a fourth noted advantage, the FBC that forms around the lateral curved surface 122 will create generally uniform forces 126 toward the sensing region 124 and around the entire lateral surface. Furthermore, when the ends 128 of the cylindrical sensor body 120 are designed with a curvature such as shown in the embodiment of FIG. 8, minimal chronic inflammatory foreign body response, and further induce a firm, substantially motion-free hold of the sensor body 120 within the host.

Figure 9A:
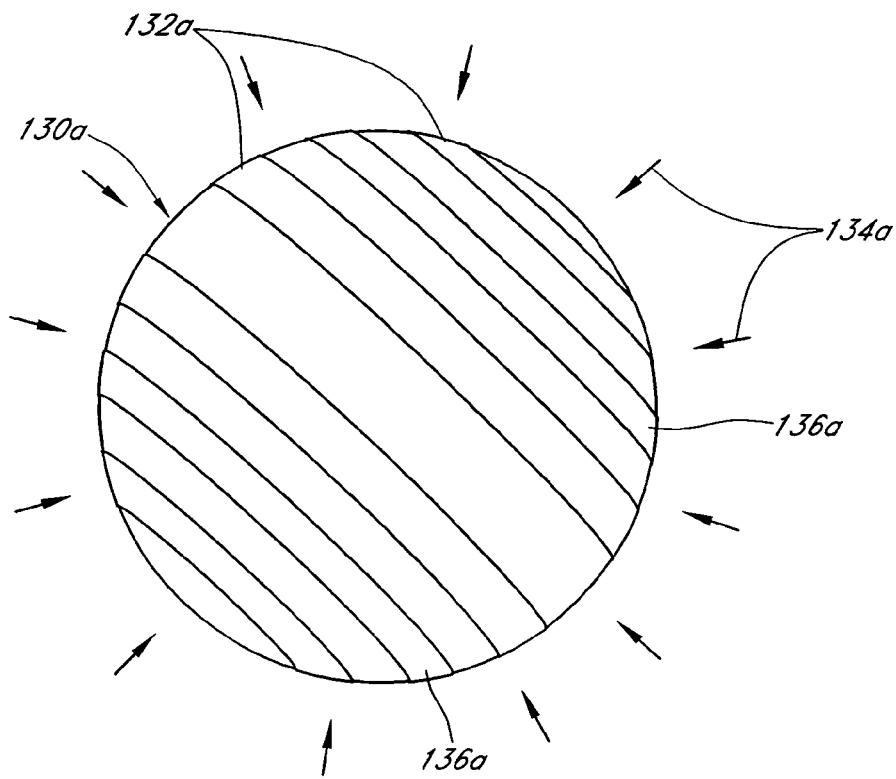
FIG. 9A is a perspective view of sensor geometry in an alternative embodiment including a substantially spherical body wherein a plurality of sensing regions are located about the circumference of the sphere.

FIG. 9A is a perspective view of a sensor geometry in an alternative embodiment including a substantially spherical body. The spherical sensor body 130a has a plurality of sensing regions 132a that encircle the body. However, in some alternative embodiments one or more sensing regions may be provided in a collective location or spread across the surface area of the sphere. Anchoring material is placed on or around the sensor body; for example, the anchoring material 136a may encircle the body in a manner similar to that of the sensing regions 132a. The embodiment of FIG. 9 takes advantage of numerous features described herein, including, but not limited to, the following advantages.

As a first noted advantage, a spherical geometry defines an optimal surface-to-volume ratio when compared to other geometries of devices with a comparable volume (e.g., rectangular, oval, and cylindrical). That is, when volume is a constant, the spherical geometry will provide an optimal surface area for tissue ingrowth in vivo in combination with an optimal curvature for uniform contractile forces from a FBC in vivo as compared to other geometries.

As a second noted advantage, entirely curved surface area of the spherical geometry lends itself to a plurality of sensing regions (e.g., electrodes) 132a and allows the sensor to sense a variety of different constituents (e.g., glucose, oxygen, interferants (e.g., ascorbate, urate, etc.)) using one compact sensor body 130a.

As a third noted advantage, when a plurality of sensing regions 132a that sense the same constituent (e.g., glucose) are spread apart, the likelihood of finding an area of the FBC that is optimized for transport of analytes is increased by the amount of increase of the area of the sensing regions.

As a fourth noted advantage, the FBC that forms around the spherical sensor body will create uniform forces 134a toward the entire surface area, including the sensing regions 132a, which may therefore be located anywhere on the sensor body. Consequently in vivo, a sensor body with a curvature such as shown in the embodiment of FIG. 9A will induce minimal chronic inflammatory foreign body response, and further induce a firm, substantially motion-free hold of the sensor body within the host.

Figure 9B:
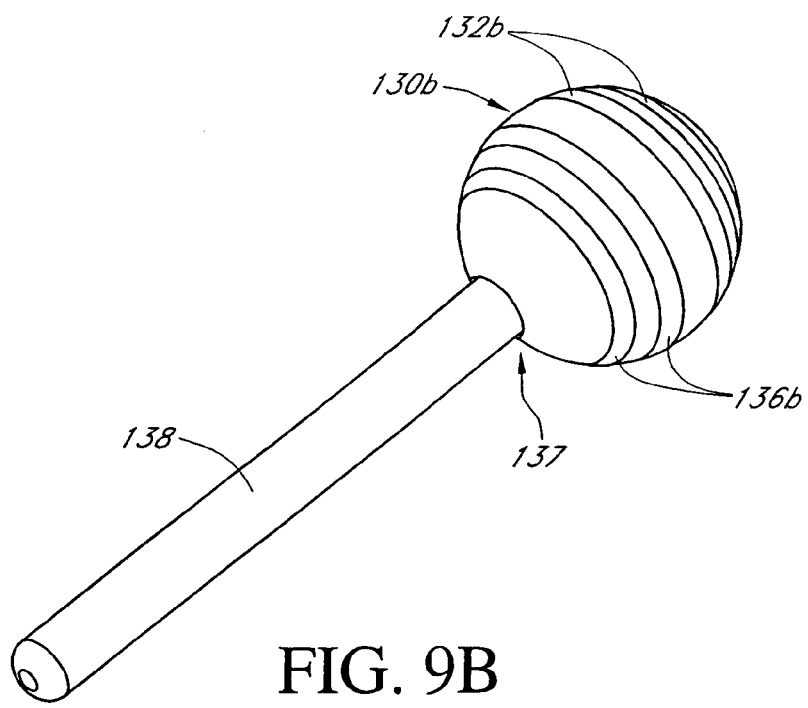
FIG. 9B is a perspective view of a sensor geometry in an alternative embodiment including a substantially spherical body with a rod extending therefrom.

FIG. 9B is a perspective view of a sensor geometry in an alternative embodiment including a substantially spherical body with a rod extending therefrom. The spherical sensing body 130b has a plurality of sensing regions 132b and anchoring material 136b that encircle (or may be otherwise located on) the body such as described with reference to FIG. 9A. However, in contrast to the embodiment of FIG. 9A, a rod 138 is connected to the spherical body 130b and houses some or all of the sensor electronics, which are described with reference to FIG. 8. The embodiment of FIG. 9B takes advantage of numerous features described herein, including those advantages described with reference to FIG. 9A, and further includes the following advantages.

The separation of at least some of the electronics between the sensing body which houses the electrodes, from the rod which may house, for example a cylindrical battery, allows for optimization of the sensing body design by minimizing the volume and/or mass requirements of the sensing body 130b due electronics. The geometric design of the sphere and rod as shown in FIG. 9B enables good formation of a FBC because all surfaces, particularly on the sensing body 130b) are curved, and there are not abrupt or flat turns or edges; that is, the contractile forces created by the FBC will be exerted generally uniformly toward at least the sensing body, and notably toward the sensing region 132b. Additionally, the sensing regions 132b are optimally located on a curved area that can be designed with maximum surface area and minimum mass and/or volume (e.g., some or all sensor electronics account for much of the mass and/or volume are located within the rod). It may be noted that in some alternative embodiments, the rod is removably attachable to the sensing body in vivo such that the electronics and/or sensing body may be individually removed and replaced (e.g., via minimally invasive methods).

Figure 10A:
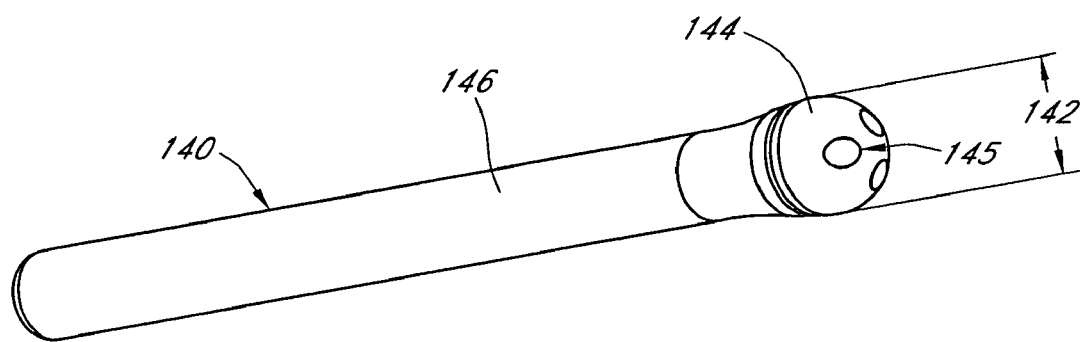
FIGS. 10A to 10D are perspective views of a sensor that has an expandable sensing body in one embodiment.
Figure 10B:
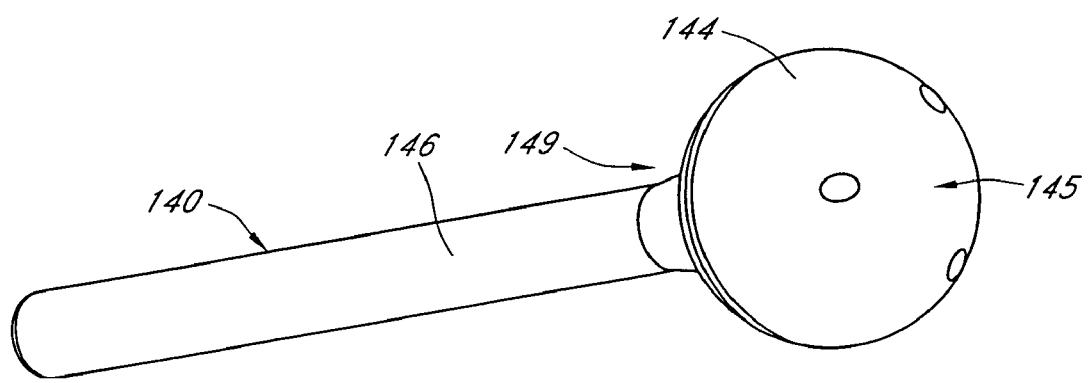
Figure 10C:
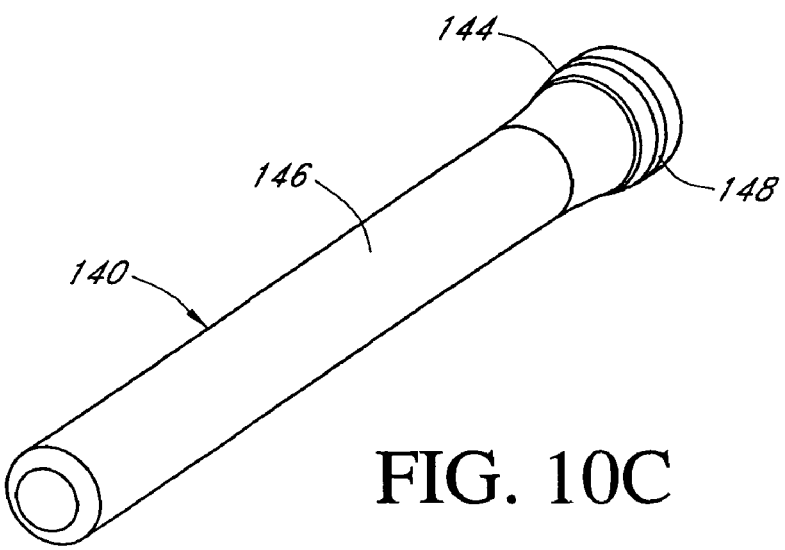
Figure 10D:
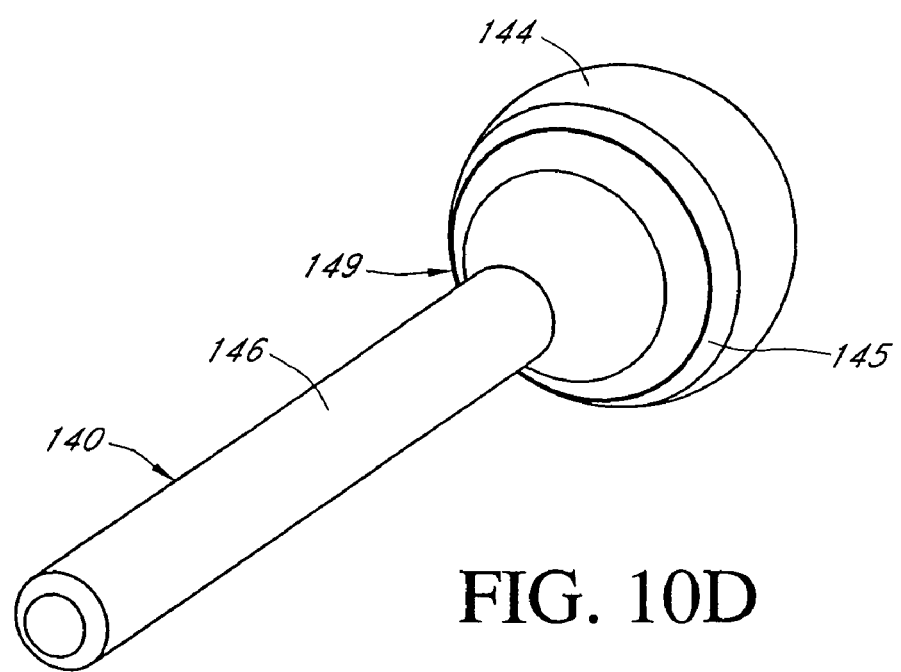

FIGS. 10A to 10D are perspective views of a sensor that has an expandable sensing body in one embodiment. FIGS. 10A and 10C are views of the sensor with the sensing body in a collapsed state, FIGS. 10B and 10D are views of the sensor with the sensing body in an expanded state. An expandable sensor 140 is advantageous in that it can be inserted into the subcutaneous space in a minimally invasive manner (e.g., through a catheter) in its collapsed state. It may be, for example, less than or equal to about 3 mm in diameter 142 and may be designed with a guide wire (not shown) extending through the sensor in some embodiments. Once it has been delivered into the appropriate site in vivo, the sensing body expands to an increased surface area.

The sensor 140 includes a sensing body 144 on which the sensing region 145 is located and an electronics body 146 in which the sensor electronics are located such as described with reference to FIG. 8. In alternative embodiments, some portion of the electronics may be housed within the sensing body. The sensing body 144 is formed from an elastomeric material and adapted for expansion using a liquid (e.g., saline or silicone oil). As an alternative, the sensing body 144 may be formed from a non-elastomeric material (e.g., polyethylene terephthalate) and folded for insertion using a catheter (not shown). As another alternative, the sensing body can be formed from nitinol, or the like, which may be advantageous due to its ability to self-expand and memorize its shape long term. In some embodiments, the expandable sensing body is adapted to fill a particular subcutaneous pocket without leaving spaces in the subcutaneous space and without causing pressure necrosis. In one example a metal framework may be used to hold the sensing body in its expanded state. The sensing region 145 includes electrodes, which are connected to the electronics body via a flexible wire or the like (not shown). Anchoring material 148 encircles (or is otherwise located on) the sensing body 144 in order to anchor the sensing body stably in vivo. The sensor electronics portion may be formed with or without a curvature, with or without anchoring material, and with or without particular concern for its effect on the foreign body capsule in vivo as it relates to the sensing body. Additional advantages of this embodiment correspond to the advantages described with reference to FIG. 9B due to its substantially similar configuration in its expanded state.

FIGS. 11A to 11D are perspective views of sensors wherein one or more sensing bodies are tethered to an electronics body in a variety of alternative embodiments. In each of the embodiments, the sensor 150 includes a sensing body 152 with a sensing region 153 located on a curved portion of the sensing body 152 such that when a foreign body capsule forms around the sensing body 152, the foreign body capsule exerts a contractile force toward the sensing region 153 as described elsewhere herein. Anchoring material 154 is located on at least a portion of the sensing body 152 in any known manner such as described elsewhere herein. Furthermore, in each of these embodiments, the electronics body 156 may include the majority of the mass of the sensor 150, which is remote from the sensing body 152. The electronics body 156 is connected to the sensing body 152 via a tether 158, which may have a variety of configurations such as described herein. As an alternative to the tether, the electronics body 156 may be connected to the sensing body 152 via a wireless RF connection (not shown) such that the electronics body 156 and the sensing body 152 may be separately implanted, explanted, monitored, and/or replaced. It may be noted that in an embodiment that utilizes RF transmission to connect the sensing body to the electronics body, some electronics are housed in the sensing body 152 to enable measurement and transmission of sensor information. Additionally, in some alternative embodiments of the tethered sensor, at least some of the electronics are housed within the sensing body.

In these embodiments wherein the sensing body 152 is tethered to the electronics body 156, the sensing body 152 can be easily optimized for surface area, shape, size, geometry, mass, density, volume, surface area-to-volume, surface area-to-density, and surface area-to-mass as desired. That is, without the mass, size, and volume constraints normally imposed by the electronics portion of a sensor, the sensing body can be optimally designed for a particular implantation site, function, or other parameter. Additionally, the electronics body can be formed from any biocompatible material (e.g., metal, ceramic, or plastic) known in the art. Additionally, it may be hermetically sealed to protect the electronic components. The tether 158 may be formed from a polymeric material or other biocompatible material and encases a conductive wire (e.g., copper) that connects the electronics within the electronics body 156 to the electronics portion of the sensing body 152 (e.g. to electrodes on the sensing region 153).

This tethered sensor design of these embodiments advantageously allows for an optimal design of the sensing body without concern for the effects of the foreign body response caused by the electronics body. The tether can be design shorter or longer, and stiffer or more flexible, in order to optimize the isolation, strain relief, and/or implantation issues.

Figure 11A:
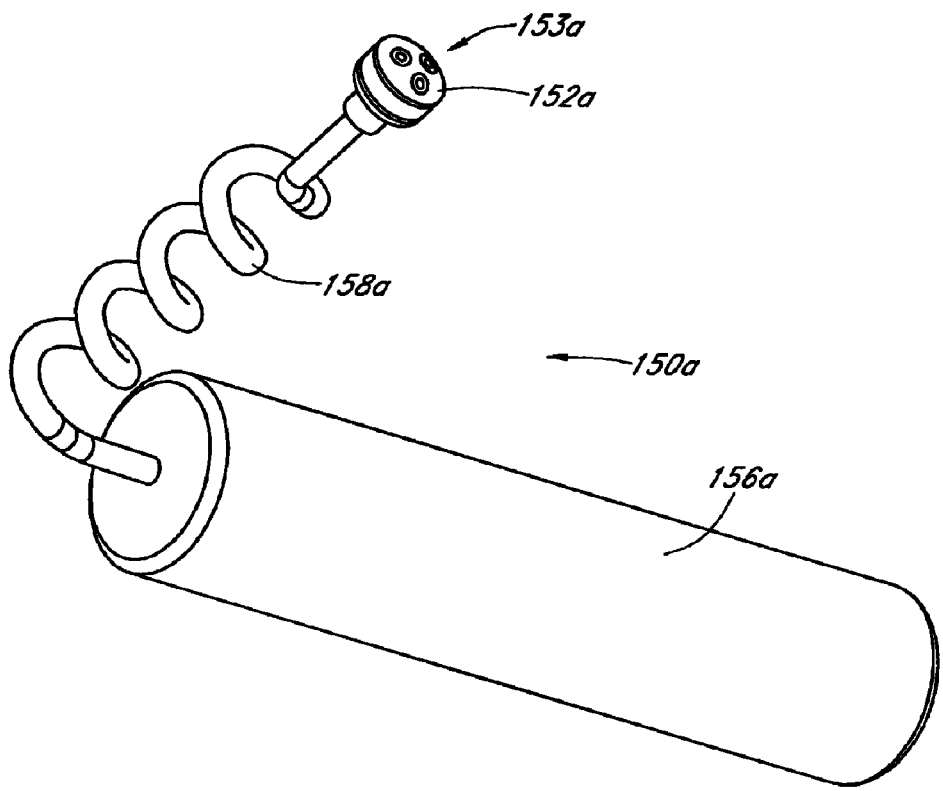
FIGS. 11A to 11D are perspective views of sensors wherein one or more sensing bodies are tethered to an electronics body in a variety of alternative embodiments.

FIG. 11A illustrates a tethered sensor 150a includes a sensing body 152a, a flexible tether 158a, and an electronics body 156a. In this exemplary embodiment, the sensing body 152a is disk-like with a curved surface on which the sensing region 153a is located. An anchoring material 154a encircles the sensing body for anchoring to the tissue. The tether acts as a strain relief, isolating the adverse effects of the FBC that forms around the electronics body 156a from the FBC that forms around the sensing body 152a.

Figure 11B:
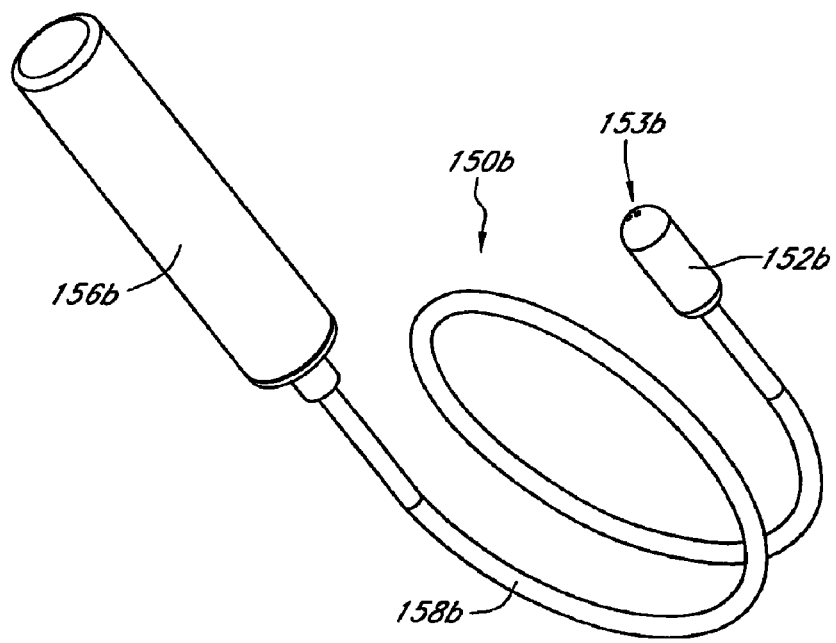

FIG. 11B illustrates an alternative tethered sensor 150b that includes a sensing body 152b, a flexible tether 158b, and an electronics body 156b. In this exemplary embodiment, the sensing body 152b comprises a cylindrical body with the sensing region 153b on a curved end. The tether 158b is formed from a flexible material and may be formed shorter or longer to adapt to an implantation site. It may be noted that a longer tether may better isolate the adverse effects of the FBC that forms around the electronics body 156b from the FBC that forms around the sensing body 152b, however a shorter tether may simplify the implantation considerations.

Figure 11C:
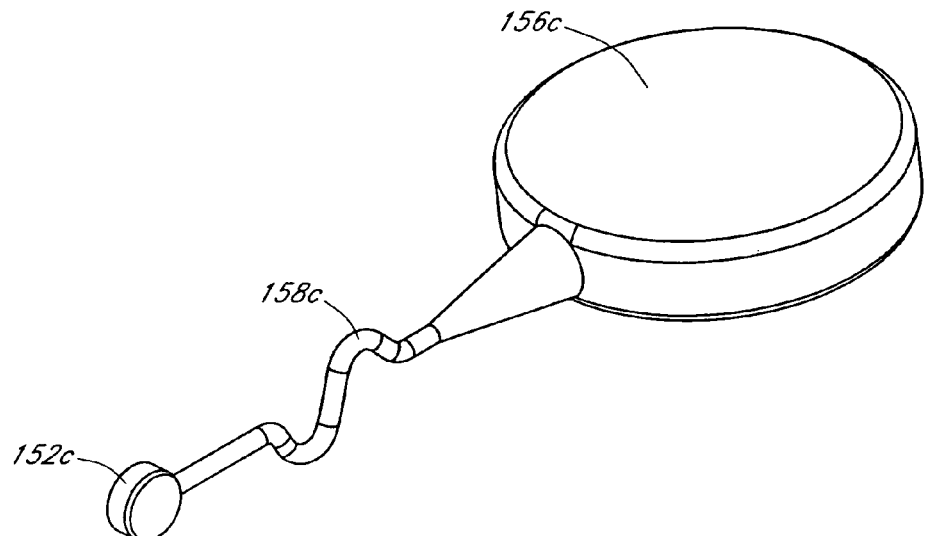

FIG. 11C illustrates an alternative tethered sensor 150c that includes a sensing body 152c, a tether 158c, and an electronics body 156c. In this exemplary embodiment, the tether may be formed from a slightly flexible to somewhat rigid material. A more rigid material may be advantageous in controlling the positioning of the sensing body 152c in vivo, a more flexible material may act as a better strain relief in vivo.

Figure 11D:
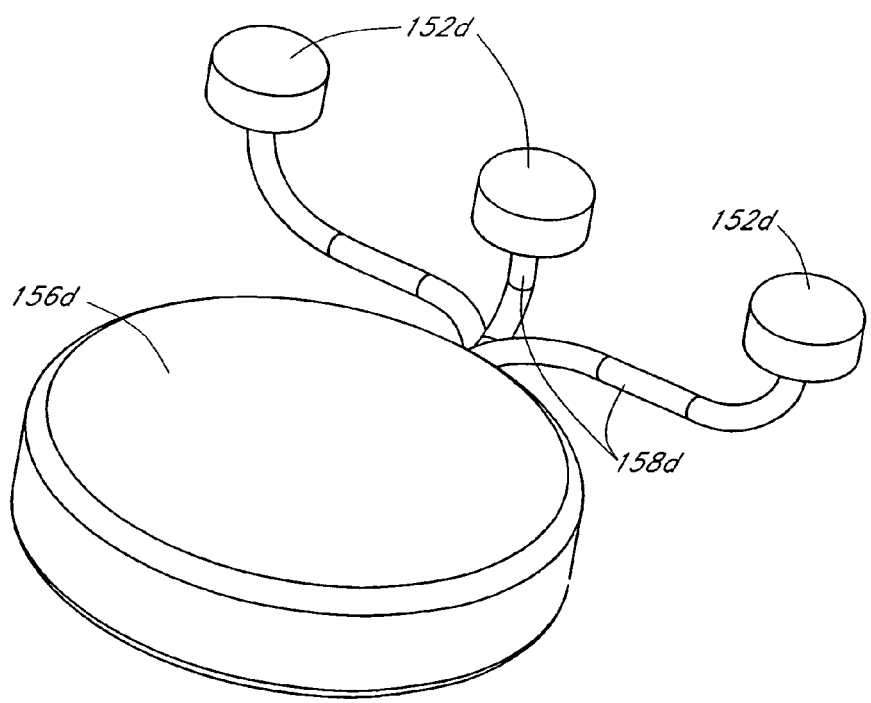

FIG. 11D illustrates an alternative tethered sensor 150d that includes a plurality of sensing bodies 152d, a tether 158d, and an electronics body 156d. In this exemplary embodiment, the plurality of sensing bodies 152d with sensing regions on a curved portion of the sensing body and anchoring material such as described elsewhere herein, however may provide additional advantages including for example, the ability to remotely turn on/off one or more of the sensing bodies 152c, the ability to determine which sensing body 152d is performing more optimally and/or consistently for optimizing accuracy and implantation site, and the ability to have a "back up" sensing body 152d in the event one or more of the sensing bodies fails to function as required.

Figure 12A:
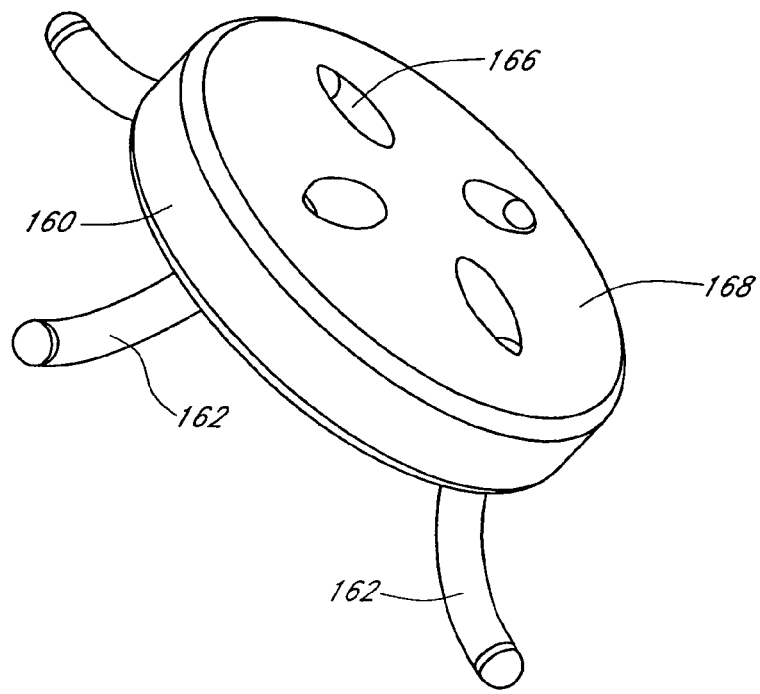
FIGS. 12A to 12B are perspective views of a sensor in an alternative embodiment wherein an electronics body is independent of the sensing bodies in a preassembled state and wherein the sensing bodies are independently inserted (and operatively connected) to the electronics body in a minimally invasive manner.
Figure 12B:
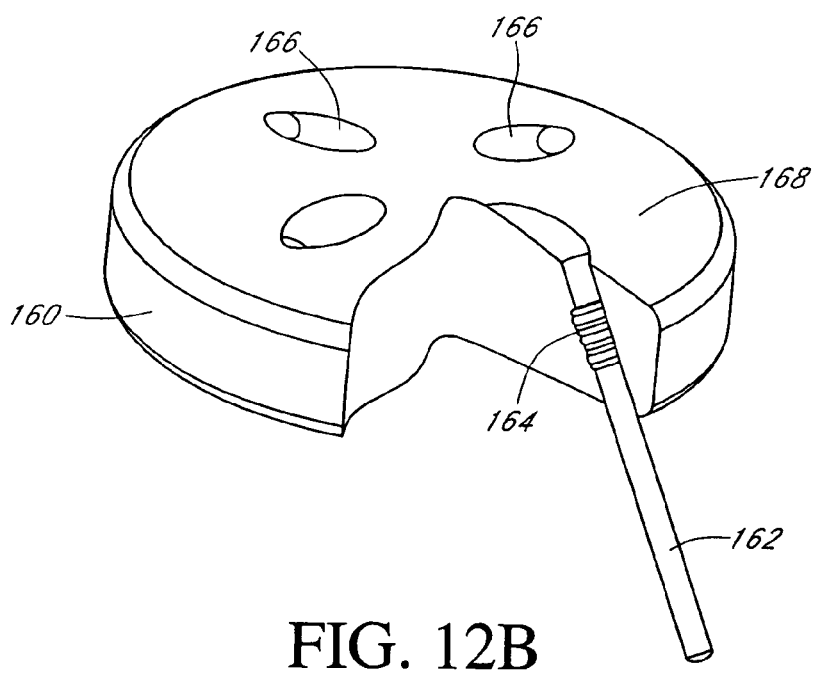

FIGS. 12A to 12B are perspective views of a sensor in an alternative embodiment wherein an electronics body is independent of the sensing bodies in a preassembled state and wherein the sensing bodies are independently inserted (and operatively connected) to the electronics body in a minimally invasive manner. Particularly, FIG. 12A illustrates the sensor wherein all four sensing bodies have been inserted and locked within the ports of the electronics body; FIG. 12B includes a cut-away portion to illustrate how the sensing body locks into electrical contact within a port of the electronics body. In this embodiment, the sensor 160 includes a plurality of independent sensing bodies 162, also referred to as biointerface probes, and include any necessary components (e.g., electrodes, biointerface materials, etc.) to sense an analyte of interest. The sensing bodies 162 further comprise electrical contacts 164 that allow the sensing bodies to operatively connect (and lock) within the multiple (optionally inclined) ports 166 of the electronics body 168. The sensing bodies 162 may be somewhat flexible and configured with a curvature and anchoring material such as described elsewhere herein.

In practice, the electronics body 168 may be implanted in the subcutaneous tissue without particular concern for the design (e.g., anchoring material, curvature, etc) and its effect on the formation of a FBC. After the FBC has healed around the electronics body 168, the sensing bodies 162 can be individually inserted in a minimally invasive manner (e.g., guide wire introduced with needle and sheath) as needed. Advantageously, each sensing body 162 functions up to about one year or more in vivo. Accordingly, when a sensing body fails to function as needed, another sensing body 162 may be inserted into another port 166 of the electronics body 168.

It may be noted that the sensors of preferred embodiments may be rigid or flexible, and of any suitable shape, including but not limited to rectangular, cylindrical, square, elliptical, oval, spherical, circular, ellipsoidal, ovoid, hourglass, bullet-shaped, porpoise-nosed, flat sheet, accordion, or any other suitable symmetrical or irregular shape. Corners may range from sharp to slightly round, to substantially round. While the sensors of preferred embodiments are preferably employed to determine the presence of an analyte, devices of preferred geometries may also be constructed for drug delivery, immunoisolation, cell transplantation, and the like. For example, the preferred device configurations can be suitable for use in fabricating an artificial pancreas.

In addition to a simple circular curvature, the curvature can also be elliptical or parabolic. The curvature can be perfectly symmetrical about the sensor head, or can possess some degree of asymmetry. While a true curvature is generally preferred, in certain embodiments a triangular profile or other polygonal profile with rounded edges may also be employed. While a smooth surface is generally preferred, in certain embodiments it may be desired to incorporate local features, such as bumps, dimples, ridges, and the like, while maintaining an overall curvature. It is generally preferred that each surface is convex, or less preferably flat but not concave. However, in certain embodiments a slightly concave or recessed surface may be acceptable presuming it is located sufficiently far from the sensing region that any chronic inflammatory response will not translate to the area adjacent the sensor head. The sensor head preferably protrudes above the radius of curvature or is flush with the radius of curvature. A recessed sensor head is generally not preferred. However, in certain embodiments such a configuration may be acceptable.

The sensor head may be positioned on any convenient location of on the device. Particularly preferred locations are the geometric center of a surface of the device, or offset to one side. In certain embodiments it may be desirable to incorporate multiple sensor heads on a single device. Such sensor heads may be spaced apart so as to maximize the distance between the sensor heads, or grouped together at one location on the device.

Manufacture of Sensor Body

In a preferred embodiment, the sensor is formed by substantially entirely epoxy encapsulating the sensor electronics; that is, the sensor body, outside the sensor head, is comprises an epoxy resin body. During the manufacture of the sensor body of the preferred embodiment, the sensitive electronic parts (e.g. battery, antenna, and circuit board, such as described in copending U.S. patent application Ser. No. 10/633,367 filed on Aug. 1, 2003 and entitled "SYSTEM AND METHODS FOR PROCESSING ANALYTE SEN- SOR DATA") are substantially entirely encapsulated in epoxy, with the exception of the sensor head. In some molding processes, the epoxy body may be formed with a curvature on a portion thereof. After the epoxy has completely cured, additional curvature may be machined, milled, laser-etched, or otherwise processed into the epoxy body to form the final geometric shape. In alternative embodiments, a light epoxy coating may be applied to the sensitive electronic parts, after which injection molding or reaction injection molding (RIM) may be used to form the final shape of the epoxy body. While a preferred sensor is constructed of epoxy resin, a non-conductive metal, ceramic or other suitable material may be used.

Anchoring Material & Implantation

In one embodiment, the entire surface of the sensor is covered with an anchoring material to provide for strong attachment to the tissues. In another embodiment, only the sensor head side of the sensor incorporates anchoring material, with the other sides of the sensor lacking fibers or porous anchoring structures and instead presenting a very smooth, non-reactive biomaterial surface to prevent attachment to tissue and to support the formation of a thicker capsule. The anchoring material may be selected from the group consisting of: polyester, polypropylene cloth, polytetrafluoroethylene felts, expanded polytetrafluoroethylene, and porous silicone.

Figure 13A:
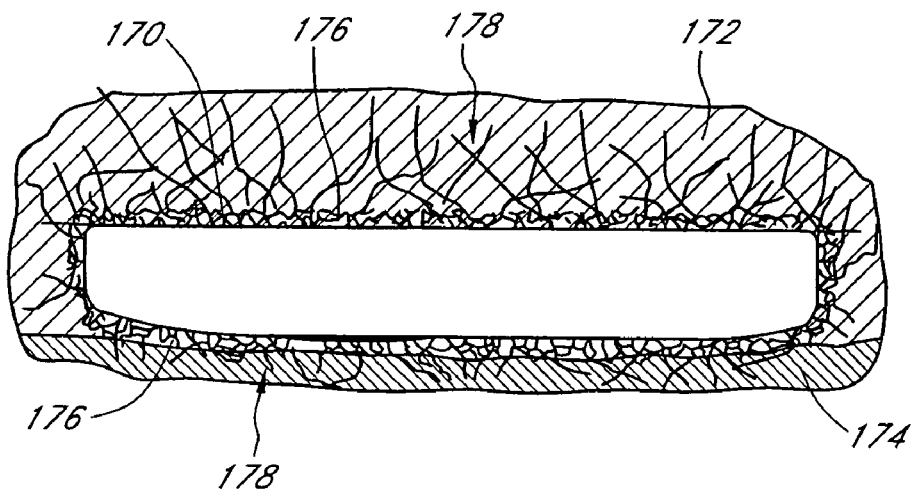
FIG. 13A is a side schematic view of an analyte sensor with anchoring material on a first and second major surface of the device, including the surface on which the sensing region is located, wherein the analyte sensor is implanted subcutaneously and is ingrown with fibrous, vascularized tissue.
Figure 13B:
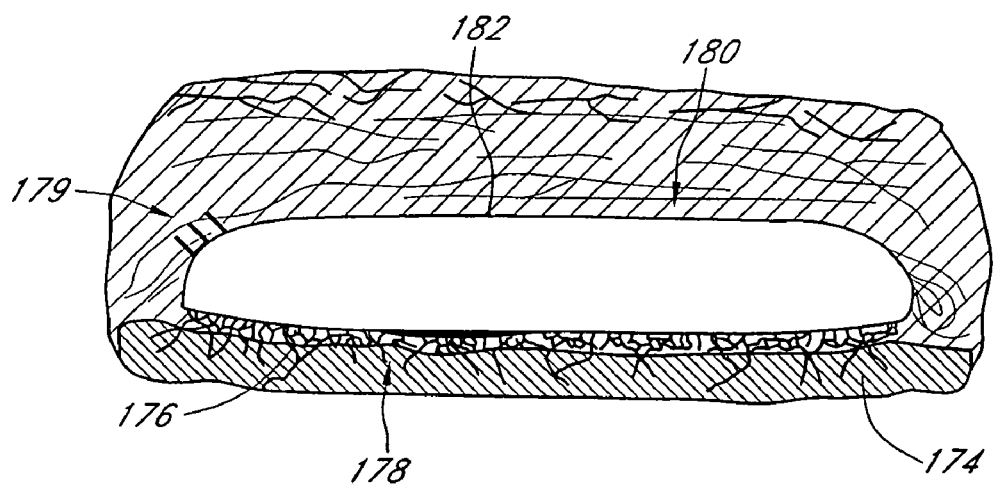

FIG. 13A is a side view of an analyte sensor with anchoring material on a first and second major surface of the device, including the surface on which the sensing region is located, wherein the analyte sensor is implanted subcutaneously and is ingrown with fibrous, vascularized tissue. FIG. 13B is a side view of an analyte sensor with anchoring material on a first major surface on which the sensing region is located, and wherein a second major surface is substantially smooth.

While these configurations of anchoring materials are particularly preferred, other configurations may also be suitable for use in certain embodiments, including configurations with different degrees of surface coverage. For example, from less than about 5, 10, 15, 20, 25, 30, 35, 40, 45, or 50% to more than about 55, 60, 65, 70, 75, 80, 85, 90, or 95% of the surface of the device may be covered with anchoring material. The anchoring material may cover one side, two sides, three sides, four sides, five sides, or six sides. The anchoring material may cover only a portion of one or more sides, for example, strips, dots, weaves, fibers, meshes, and other configurations or shapes of anchoring material may cover one or more sides. Likewise, while silicone and polyester fibers are particularly preferred, any biocompatible material capable of facilitating anchoring of tissue to the device may be employed.

It may be noted that the optimum amount of anchoring material that may be used for any particular sensor is dependent upon one or more of the following parameters: implantation site (e.g., location in the host), surface area, shape, size, geometry, mass, density, volume, surface area-to-volume, surface area-to-density, and surface area-to-mass. For example, a device with a greater mass as compared to a device with a lesser mass may require more anchoring material to support the greater mass differential.

In preferred embodiments, the sensor of the described geometry is implanted at the interface between two kinds of tissue, and is preferably anchored to the more robust tissue type. For example, the sensor may be placed adjacent to an organ (for example, a kidney, the liver, or the peritoneal wall), or adjacent to the fascia below adipose tissue. When implanted in such a fashion, the sensor geometry minimizes force transference, permitting non-anchored tissue to move over the smooth surface of the sensor, thereby minimizing the force transferred to the underlying tissue to which the sensor is anchored. While it is generally preferred to anchor the sensor to the more robust tissue type, in certain embodiments it may be preferred to anchor the sensor to the less robust tissue type, permitting the more robust tissue to move over the smooth surface of the sensor. While the sensor geometries of preferred embodiments are particularly preferred for use at tissue interfaces, such sensors are also suitable for use when implanted into a single type of tissue, for example, muscle tissue or adipose tissue. In such embodiments, however, the sensor geometry may not confer any benefit, or only a minimal benefit, in terms of force transference. Other benefits may be observed, however. In another embodiment, the sensor may be suspended, with or without sutures, in a single tissue type, or be placed between two tissue types, and anchoring material covering substantially the entire surface of the device may be employed.

In some alternative embodiments, a mechanical anchoring mechanism, such as prongs, spines, barbs, wings, hooks, helical surface topography, gradually changing diameter, or the like, may be used instead of or in combination with anchoring material such as described herein. For example when an oblong or cylindrical type sensor is implanted within the subcutaneous tissue, it may tend to slip along the pocket that was formed during implantation, particularly if some additional space exists within the pocket. This slippage can lead to increased inflammatory response and/or movement of the sensor prior to or during tissue ingrowth. Accordingly, a mechanical mechanism can aid in immobilizing the sensor in place, particularly prior to formation of a mature foreign body capsule. One example of mechanical anchoring means is shown on FIG. 13B, at 179; however, it should be noted that the placement and configuration of a mechanical anchoring mechanism is broad in scope as described herein.

FIG. 13A illustrates the surface of the sensor 140 in mechanical contact with the overlying tissue 172, as well as the underlying muscle fascia 174, due to the ingrowth of the fibrous tissue and vasculature. In this embodiment, any surface of the sensor 170 covered with anchoring material 176 is typically ingrown with fibrous, vascularized tissue 178, which aids in anchoring the sensor and mitigating motion artifact. It may be noted however, that in some cases, forces applied laterally to this tissue may be translated to the sensor, and likewise to the fascia side of the sensor, causing potential disruption of the interface with the fascia. Therefore, although the radial profile of the side of the sensor incorporating the sensor head assists in preventing forces in the distal subcutaneous tissue from exerting forces on the sensor head side, which is attached to the muscle fascia by an anchoring material, complete coverage of the device with anchoring material may not be preferred in certain embodiments.

An anchoring material covering the sensor may also make it difficult to remove the sensor for maintenance, repair, or permanent removal if its function is no longer necessary. It is generally difficult to cut down through the surrounding tissue to the surface of the sensor without also cutting into the anchoring material and leaving some of it behind in the patient's tissues. Leaving a portion of the sensor free of anchoring material enables the sensor to be more easily removed by locating the smooth surface, grasping the sensor with a holding tool, and then cutting along the plane of the anchoring material to fully remove the sensor. In certain embodiments, however, it may be desirable for the entire surface of the sensor, or a substantial portion thereof, to be covered with an anchoring material. For example, when implanted into a single tissue type (subcutaneous adipose tissue, or muscle tissue), it may be desirable to have anchoring over all or substantially the entire surface of the sensor. In still other embodiments, no anchoring at all may be preferred, for example, in sensors having very small dimensions. One contiguous sheet of anchoring material can be employed, or two or more different sheets may be employed, for example, an array of dots, stripes, mesh, or other suitable configuration of anchoring material.

FIG. 13B illustrates a preferred embodiment wherein the surface 180 of the sensor facing away from the muscle fascia 174 (e.g., surface opposite the sensing region) is not covered with anchoring material, but instead is a smooth, biocompatible material that is non-adhesive to tissues 182. It is also generally preferred that the surface 180 facing away from the fascia have a radius of curvature, although in certain embodiments it may also be acceptable for the surface to have another shape, for example, a flat surface. When mechanical force is applied to the overlying tissue, the force is dissipated in the elastic foreign body response overlying the sensor, and is not effectively translated through the sensor to the biointerface with the fascia. This preferred configuration decreases damage to the biointerface caused by external forces. Moreover, for sensor removal, the surgeon can easily find the outermost surface of the sensor without cutting into it. The outermost aspect of the sensor is surrounded by a thick foreign body capsule, which substantially frees the sensor when it is cut free. Once the sensor is located and grasped by the surgeon, complete removal by careful dissection of the face of the sensor associated with the fascia can be readily accomplished. Transference of lateral force around a sensor with anchoring material covering the entire surface compared to sensors with anchoring materials covering only the face with the sensor head are depicted in FIG. 13A and FIG. 13B, respectively.

In other words, in FIG. 13A, vascular and fibrous tissues 178 intertwine with the anchoring material 176. When a force is applied to tissue overlying the sensor of FIG. 13A, it may be translated into the sensor because of the mechanical attachment of the sensor to the fibrous tissue, which grows into the interstices of the anchoring material. In contrast, the sensor of FIG. 13B is smooth on the side opposite the fascia. When mechanical energy is applied to the overlying tissue, it is not effectively transferred to the sensor because the tissue is not attached to the sensor nor intertwined with it.

It may be noted that the smoothness of the surface of the device can be measured by any suitable method, for example, by profilometry as described in U.S. Pat. No. 6,517,571, the contents of which is hereby incorporated by reference in its entirety. Measurements are preferably taken from representative areas (for example, square areas of 500 microns length on each side) of the smooth surface of the device. A surface is generally considered "smooth" if it has a smoothness of less than 1.80 microns RMS. Surfaces with a smoothness greater than or equal to 1.80 microns RMS are generally considered "rough." In certain embodiments, however, the cut-off between "rough" and "smooth" may be higher or lower than 1.80 microns RMS.

Profilometry measurements can be performed with a Tencor Profiler Model P-10, measuring samples of square areas of 500-micron length per side. Surface data measurements can be made using the Tencor Profiler Model P-10 with a MicroHead or Exchangeable Measurement Head (stylus tip radius of 2.0 microns with an angle of 60°). Preferred menu recipe settings for the profilometer are as follows:

| | |
|---|---|
| Scan length: | 500 microns |
| Scan speed: | 50 microns/second |
| Sampling rate: | 200 Hz |
| No. of traces: | 50 |
| Spacing between traces: | 10 microns |
| No. of points/trace: | 2000 |
| Point interval: | 0.25 microns |
| Stylus force: | 5 mg |
| Range/resolution: | 65 microns/0.04 Angstroms |
| Profile type: | Peaks and valleys |
| Waviness filter: | 45 mm/1.8 in. |

Cursors can be set at each end of the length of each area to be sampled, for example, at 0 microns and at 500 microns. Scans can be performed in the longitudinal direction of tubular samples, or in any convenient direction for samples of other shapes. A parameter correlating to roughness of surfaces of the devices of preferred embodiments is Rq, which is the Root-Mean-Square (RMS) roughness, defined as the geometric average of the roughness profile from the mean line measured in the sampling length, expressed in units of microns RMS.

The use of an alternative (finer) waviness filter during profilometry allows for materials that include gross surface non-uniformities, such as corrugated surfaces made from microscopically smooth materials.

In certain embodiments it is preferred that the smooth surfaces of the device are smooth in their entirety, namely, along the entire length of the surface. For surfaces of relatively uniform smoothness along their entire length, surface measurements are preferably made at three points along the length of the surface, specifically at points beginning at one fourth, one half and three fourths of the length of the surface as measured from one end of device to the other. For surfaces of non-uniform surface character along their entire length, five samples equally spaced along the length are preferably considered. The measurements from these 3-5 sample areas are then averaged to obtain the surface value for the smooth surface. In other embodiments, however, other methods of obtaining measurements may be employed.

An article entitled "Atomic force microscopy for characterization of the biomaterial interface" describes the use of AFM for consideration of surface smoothness (Siedlecki and Marchant, Biomaterials 19 (1998), pp. 441-454). AFM may be usefully employed for the smoothness evaluation of device surfaces where the resolution of profilometry is marginally adequate for extremely smooth surfaces. However, for purposes of the preferred embodiments, profilometry measurements made using the above-described Tencor profilometer are generally adequate for determining the smoothness of the device surface

EXAMPLES

Weekly infusion studies were conducted for four-weeks to investigate the effects of sensor geometries of preferred embodiments on the functional performance of glucose sensors. A first group of sensors (n=5) included a cylindrical geometry similar to that described with reference to FIG. 4. A second group of sensors (n=6) included a thin, oblong geometry similar to that described with reference to FIG. 5. The functional aspects of each sensor were constructed in a similar manner, such as described in Published Patent Application No. 2003/0032874, which is incorporated herein by reference. The sensors were then implanted into the subcutaneous tissue in dogs between the fascia and adipose tissues, and sensor function evaluated by weekly glucose infusion tests.

The implantation entailed making a 1-inch incision, then forming a pocket lateral to the incision by blunt dissection. After placement of the device with the sensing region facing towards the fascia, a suture was placed by pulling the connective tissue together at the end of the device proximal to the incision. It is believed that the sutures held effectively during wound healing and device integration with tissues.

FIG. 14A is a graph showing the percentage of functional sensors from the two different sensor geometry groups. The x-axis represents time in weeks; the y-axis represents percentage of functional sensors for each group during the weekly infusion studies. It is known that an initial startup period exists for sensors implanted in the subcutaneous space, between about one and three weeks, during which delayed sensor functionality may be related to the amount and speed of tissue ingrowth into the biointerface, as described with reference to copending U.S. patent application Ser. No. 10/647,065 filed Aug. 22, 2003 and entitled "POROUS MEMBRANE FOR USE WITH IMPLANTABLE DEVICES." Interestingly, both sensor geometries functioned substantially as expected in that the majority of devices were functional by week four. However, the sensors of the thin, oblong sensor geometry group showed faster start-up times as evidenced by a higher percentage of functional sensors at weeks two and three.

The delayed start-up of the cylindrical group as compared to the thin, oblong group is believed to be due to delayed ingrowth of tissues or lack of ingrowth of tissues, which effects device function through lack of glucose sensitivity, compromised function after start-up, low sensitivity, and long time lags. One cause for this delay of or lack of tissue ingrowth in the cylindrical group is believed to be the placement of the sensing region on the device. Particularly, when a sensor is implanted in the subcutaneous space between two tissue types, such as the adipose subcutaneous tissue and the fascia, optimal tissue ingrowth may occur when the sensor is directly adjacent and fully engaged with the fascia, such as described with reference in FIG. 5B. In contrast to the sensors of the thin, oblong geometry group, when the sensors of the cylindrical are implanted in the pocket formed between the two tissue types, a space may exist adjacent at least a portion of the sensing region between the two tissue types creating delayed or lack of tissue ingrowth due to spacing from soft tissue. Accordingly, it may be advantageous to design the sensing region on a sensor body such that the entire sensing region is directly adjacent to the fascia or similar tissue immediately after implantation.

Some additional observations may be directly related to the delayed sensor function in the cylindrical sensors of this study. For example, the thin, oblong geometry as compared to the cylindrical geometry does not protrude from the host as much and is less amenable to accidental bumping or movement, and less available for patient "fiddling." Thus, it may be inferred that overall dimensions may effect sensor geometry such that by increasing the discreetness of the geometry (e.g., mass, shape, dimensions), sensor functionality may improve. As another example, the thin, oblong geometry as compared to the cylindrical geometry is less susceptible to torsion and/or rotational forces, which may create motion artifact and therefore chronic inflammatory response at the device-tissue interface. In other words, with the sensor head oriented down towards the fascia, and nearer to the center of the sensor, downward pressure on either end is not transferred as shear force to the sensor head; even if the sensor is moved, the sensor head more likely remains adjacent to the tissue so that it may heal in a favorable fashion, unlike the sensors wherein the tip is positioned on an end of the sensor body, which can leave a space after lateral movement. From this observation, it may be hypothesized that surface area-to-volume ratio may effect the function of the sensor. Particularly, an increased surface area-to-volume ratio, particularly as a consequence of reducing the volume of the sensor, may decrease the effects of forces (e.g., torsion, rotational, and shearing) caused by behavioral and environment movement. Similarly, optimization of surface area-to-mass and surface area-to-density ratios may impact healing.

FIG. 14B is a graph showing the average R-value of sensors from a study of the two different sensor geometries implanted in a host. The x-axis represents time in weeks; the y-axis represents average R-value for each group of sensors during each weekly infusion study. R-values were obtained by correlating sensor output to the externally derived meter values, and performing a least squares analysis, such as described with reference to copending U.S. patent application Ser. No. 10/633,367 filed on Aug. 1, 2003 and entitled "SYSTEM AND METHODS FOR PROCESSING ANALYTE SENSOR DATA."

It may be observed that both geometry groups performed with sufficient accuracy by week three (e.g., greater than 0.79 R-value constitutes sufficient accuracy in one example). It may also be observed that the sensors of the thin, oblong group increased in accuracy and were more consistent than the sensors of the cylindrical group. It is believed that the slightly improved performance of the thin, oblong group as compared to the cylindrical group may be due to a variety of factors, including those described with reference to FIG. 11A, and additional factors such as surface area, size, mass, density, volume, surface area-to-volume, surface area-to-density, and surface area-to-mass.

From the observations of the above described study, optimization of the sensor geometry may additionally include: 1) density optimization to better correspond to the density of tissue (e.g., fascia or adipose), 2) surface area-to-volume optimization by increasing the surface area-to-volume ratio of the sensor, 3) size optimization by decreasing the overall size, mass, and/or volume of the sensor, and 4) surface area-to-mass optimization by increasing the surface area-to-mass ratio of the sensor, for example.

Table 1 illustrates additional analysis from the above described infusion study, including a comparison of average R-value at week 4 and standard deviation at week 4 for the two groups of sensors.

TABLE 1

| Results of Geometry Study | Cylindrical Geometry with sensor on curved end | Thin, oblong geometry with sensor on curved major surface |
|---|---|---|
| Average R-value at Week 4 | 0.73 | 0.87 |
| Standard Deviation at Week 4 | 0.41 | 0.08 |

As described above with reference to FIG. 11B, the average R-value at week 4 was better for the thin, oblong group as compared to the cylindrical group. Additionally the average standard deviation of the thin, oblong group as compared to the cylindrical group was much lower, indicating greater consistency and tighter tolerances with the thin, oblong group. As described above with reference to FIGS. 11A and 11B, this performance differential may be due to additional geometric factors such as surface area-to-volume ratio, size, mass, and surface area-to-density ratio, for example.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention as embodied in the attached claims. All patents, applications, and other references cited herein are hereby incorporated by reference in their entirety.

What is claimed is:

1. An implantable sensor for use in measuring a concentration of an analyte in a bodily fluid, the sensor comprising: a body comprising an electrochemical sensing region adapted for transport of an analyte between the electrochemical sensing region and a bodily fluid, wherein the electrochemical sensing region comprises one or more electrodes, wherein the body comprises a first major surface and a second major surface, wherein the one or more electrodes are situated approximately at a center of the first major surface, wherein the electrochemical sensing region is located on a curved portion of the first major surface configured such that when a foreign body capsule forms around the sensor, a contractile force is exerted by the foreign body capsule toward the sensing region, and wherein the sensor is a subcutaneous sensor configured for implantation in a soft tissue of a host.

2. The sensor of claim 1, wherein the electrochemical sensing region comprises a plurality of electrodes.

3. The sensor of claim 1, wherein the second major surface is flat.

4. The sensor of claim 1, wherein the second major surface has a curvature.

5. The sensor of claim 1, wherein the first major surface, when viewed from a direction perpendicular to a center of the first major surface, has a substantially oval profile.

6. The sensor of claim 1, wherein the first major surface, when viewed from a direction perpendicular to a center of the first major surface, has a substantially circular profile.

7. The sensor of claim 1, wherein at least one of the first major surface or the second major surface has a non-electrode surface area comprising an anchoring material for supporting tissue ingrowth.

8. The sensor of claim 1, further comprising a mechanical anchoring mechanism formed on the body.

9. The sensor of claim 1, wherein the curved portion of the first major surface has a plurality of radii of curvature.

10. The sensor of claim 1, wherein the curved portion of the first major surface has a radius of curvature of from about 0.5 mm to about 10 cm.

11. The sensor of claim 1, wherein the first major surface and the second major surface together account for at least about 40% of the surface area of the body.

12. The sensor of claim 1, wherein edges of the first major surface are rounded and transition smoothly away from the first major surface.

13. The sensor of claim 1, wherein the body defines a surface area, and wherein from 10% to 100% of the surface area is convexly curved.

14. The sensor of claim 1, wherein the body comprises plastic.

15. The sensor of claim 14, wherein the plastic is selected from the group consisting of thermoplastic and thermoset.

16. The sensor of claim 15, wherein the thermoset is selected from the group consisting of epoxy, silicone, and polyurethane.

17. The sensor of claim 1, wherein the body comprises a material selected from the group consisting of metal, ceramic, and glass.

18. The sensor of claim 1, further comprising a porous biointerface material that covers at least a portion of the sensing region.

19. The sensor of claim 18, wherein the biointerface material comprises interconnected cavities dimensioned and arranged to interfere with formation of occlusive cells.

20. The sensor of claim 1, wherein the sensor is a glucose sensor.

21. The sensor of claim 1, wherein the electrochemical sensing region comprises a multi-region membrane covering one or more of the one or more electrodes.

22. The sensor of claim 21, wherein the multi-region membrane comprises an enzyme.

23. The sensor of claim 1, wherein the first major surface and the second major surface together account for at least about 50% of a total surface area of the body.

24. The sensor of claim 1, wherein the electrochemical sensing region comprises a silicone-containing material covering one or more of the one or more electrodes.

25. A wholly implantable sensor adapted to measure a concentration of an analyte in a bodily fluid, comprising: a wholly implantable body comprising an electrochemical sensing region comprising one or more electrodes, wherein the one or more electrodes are located on a curved portion of a first major surface of the body, wherein the body further comprises a second major surface, wherein the sensing region is situated approximately at a center of the first major surface, wherein the sensor is a subcutaneous sensor suitable for implantation in a soft tissue of a host, and wherein a non-electrode surface area of the body comprises a porous anchoring material for supporting tissue ingrowth.

26. The sensor of claim 25, wherein the electrochemical sensing region comprises a plurality of electrodes.

27. The sensor of claim 25, wherein the electrochemical sensing region comprises a multi-region membrane covering one or more of the one or more electrodes.

28. The sensor of claim 27, wherein the multi-region membrane comprises an enzyme.

29. The sensor of claim 25, wherein the first major surface and the second major surface together account for at least about 50% of the surface area of the body.

30. The sensor of claim 25, wherein a non-electrode surface area of the body comprises a porous anchoring material for supporting tissue ingrowth.

31. The sensor of claim 25, wherein the electrochemical sensing region comprises a silicone-containing material covering one or more of the one or more electrodes.

32. The sensor of claim 25, wherein the curved portion of the first major surface has a plurality of radii of curvature.

33. The sensor of claim 25, wherein the curved portion of the first major surface has a radius of curvature of from about 0.5 mm to about 10 cm.

34. The sensor of claim 25, wherein the sensor is a glucose sensor.

35. An implantable sensor adapted to measure a concentration of an analyte in a bodily fluid, comprising: a body having a first major surface and, opposite thereto, a second major surface, wherein the first major surface is generally planar, slightly convex, and has rounded edges, with an electrochemical sensing region comprising one or more electrodes located on the first major surface, wherein the electrochemical sensing region is spaced away from the rounded edges and approximately at a center of the first major surface, wherein the electrochemical sensing region comprises a silicone-containing material, wherein the first major surface is configured to be sufficiently convex that when a foreign body capsule forms around the sensor, contractile forces are exerted thereby generally uniformly towards the electrochemical sensing region, and wherein the sensor is a subcutaneous sensor configured for implantation in a soft tissue of a host.

36. The sensor of claim 35, wherein the electrochemical sensing region comprises a plurality of electrodes.

37. The sensor of claim 35, wherein the electrochemical sensing region comprises a multi-region membrane covering one or more of the one or more electrodes.

38. The sensor of claim 37, wherein the multi-region membrane comprises an enzyme.

39. The sensor of claim 35, wherein the first major surface and the second major surface together account for at least about 50% of the surface area of the body.

40. The sensor of claim 35, wherein a non-electrode surface area of the body comprises a porous anchoring material for supporting tissue ingrowth.

41. The sensor of claim 35, wherein the electrochemical sensing region comprises a silicone-containing material covering one or more of the one or more electrodes.

42. The sensor of claim 35, wherein the first major surface has a plurality of radii of curvature.

43. The sensor of claim 35, wherein the first major surface has a radius of curvature of from about 0.5 mm to about 10 cm.

44. The sensor of claim 35, wherein the sensor is a glucose sensor.

* * * * *

UNITED STATES PATENT AND TRADEMARK OFFICE
CERTIFICATE OF CORRECTION

PATENT NO. : 7,881,763 B2
APPLICATION NO. : 11/415631
DATED : February 1, 2011
INVENTOR(S) : Brauker et al.

It is certified that error appears in the above-identified patent and that said Letters Patent is hereby corrected as shown below:

| Issued Patent | | Description of Discrepancy |
|---|---|---|
| Column | Line | |
| (Item 56) Page 3 Col. 2 | 72 | Under U.S. Patent Documents, change "Colvin et al." to --Colvin, Jr. et al.--. |
| (Item 56) Page 4 Col. 1 | 30 | Under U.S. Patent Documents, change "King et al." to --Zhong et al.--. |
| (Item 56) Page 4 Col. 1 | 40 | Under U.S. Patent Documents, change "Berner et al." to --Kim et al.--. |
| (Item 56) Page 4 Col. 1 | 52 | Under U.S. Patent Documents, change "Ono et al." to --Kunimoto et al.--. |
| (Item 56) Page 6 Col. 1 | 13 | Under Other Publications, change "at" to --et--. |
| (Item 56) Page 6 Col. 1 | 15 | Under Other Publications, change "at" to --et--. |
| (Item 56) Page 6 Col. 1 | 20 | Under Other Publications, change "at" to --et--. |
| (Item 56) Page 6 Col. 1 | 54 | Under Other Publications, change "at" to --et--. |
| (Item 56) Page 6 Col. 1 | 64 | Under Other Publications, change "Aniodic" to --Anodic--. |

Signed and Sealed this
Twenty-sixth Day of July, 2011

David J. Kappos
*Director of the United States Patent and Trademark Office*

| | | |
|---|---|---|
| (Item 56)<br>Page 6<br>Col. 2 | 59 | Under Other Publications,<br>change "at" to --et--. |
| (Item 56)<br>Page 7<br>Col. 1 | 24 | Under Other Publications,<br>change "at" to --et--. |
| (Item 56)<br>Page 7<br>Col. 1 | 38 | Under Other Publications,<br>change "at" to --et--. |
| (Item 56)<br>Page 7<br>Col. 1 | 54 | Under Other Publications,<br>change "nonirnmunosuppressed"<br>to --nonimmunosuppressed--. |
| (Item 56)<br>Page 7<br>Col. 1 | 62 | Under Other Publications,<br>after "(FBC).""<br>insert --Fraser, D.M. (Ed.).--. |
| (Item 56)<br>Page 7<br>Col. 1 | 64 | Under Other Publications,<br>change "Lts.," to --Ltd.,--. |
| (Item 56)<br>Page 7<br>Col. 1 | 71 | Under Other Publications,<br>change "Aced" to --Acad--. |
| (Item 56)<br>Page 7<br>Col. 2 | 1 | Under Other Publications,<br>change "at" to --et--. |
| (Item 56)<br>Page 7<br>Col. 2 | 7 | Under Other Publications,<br>change "at" to --et--. |
| (Item 56)<br>Page 9<br>Col. 1 | 65 | Under Other Publications,<br>change "basedon" to --based on--. |
| (Item 56)<br>Page 9<br>Col. 2 | 15 | Under Other Publications,<br>change "reliablity" to --reliability--. |
| (Item 56)<br>Page 9<br>Col. 2 | 26 | Under Other Publications,<br>change "Enzymlology,"<br>to --Enzymology,--. |
| (Item 56)<br>Page 9<br>Col. 2 | 38 | Under Other Publications,<br>change "artifical" to --artificial--. |
| (Item 56)<br>Page 9<br>Col. 2 | 51 | Under Other Publications,<br>change "for your" to --for you--. |
| (Item 56)<br>Page 9<br>Col. 2 | 62 | Under Other Publications,<br>change "glocuse" to --glucose--. |

CERTIFICATE OF CORRECTION (continued)
U.S. Pat. No. 7,881,763 B2

| | | |
|---|---|---|
| (Item 56) Page 9 Col. 2 | 63 | Under Other Publications, change "Diabetese" to --Diabetes--. |
| (Item 56) Page 10 Col. 1 | 13 | Under Other Publications, change "Diabetese" to --Diabetes--. |
| (Item 56) Page 10 Col. 1 | 28 | Under Other Publications, change "inactiviation" to -- inactivation--. |
| (Item 56) Page 10 Col. 1 | 36 | Under Other Publications, change "patents" to --patients--. |
| (Item 56) Page 10 Col. 2 | 36 | Under Other Publications, change "activitiy," to --activity,--. |
| (Item 56) Page 10 Col. 2 | 47 | Under Other Publications, change "Beioelectronics," to --Bioelectronics,--. |
| (Item 56) Page 10 Col. 2 | 48 | Under Other Publications, change "glocuse" to --glucose--. |
| (Item 56) Page 10 Col. 2 | 61 | Under Other Publications, change "valication" to --validation--. |
| (Item 56) Page 10 Col. 2 | 62 | Under Other Publications, change "iunsulin interaaction in tyhpe" to --insulin interaction in type--. |
| (Item 56) Page 11 Col. 1 | 10 | Under Other Publications, change "artifical" to --artificial--. |
| (Item 56) Page 11 Col. 1 | 16 | Under Other Publications, change "amperometeric" to --amperometric--. |
| (Item 56) Page 11 Col. 1 | 53 | Under Other Publications, change "termistor" to --thermistor--. |
| (Item 56) Page 11 Col. 1 | 54 | Under Other Publications, change "metobolites," to --metabolites,--. |
| (Item 56) Page 11 Col. 1 | 56 | Under Other Publications, change "cholesteral and cholesteral" to --cholesterol and cholesterol--. |
| (Item 56) Page 11 Col. 1 | 58 | Under Other Publications, change "Apllied" to --Applied--. |

| | | |
|---|---|---|
| (Item 56) Page 11 Col. 2 | 49 | Under Other Publications, change "Subcutaenous" to --Subcutaneous--. |
| (Item 56) Page 11 Col. 2 | 55 | Under Other Publications, change "assitance" to --assistance--. |
| (Item 56) Page 11 Col. 2 | 59 | Under Other Publications, change "ilI" to --ill--. |
| (Item 56) Page 12 Col. 1 | 6 | Under Other Publications, change "Aced" to --Acad--. |
| (Item 56) Page 12 Col. 1 | 23 | Under Other Publications, change "pancrease" to --pancreas--. |
| (Item 56) Page 12 Col. 1 | 51 | Under Other Publications, change "Membrance" to --Membrane--. |
| (Item 56) Page 12 Col. 1 | 53 | Under Other Publications, change "cholesteral" to --cholesterol--. |
| (Item 56) Page 12 Col. 1 | 60 | Under Other Publications, change "Deabetes" to --Diabetes--. |
| (Item 56) Page 12 Col. 2 | 7 | Under Other Publications, change "Tranducers" to --Transducers--. |
| 6 | 45 | Change "environment" to --embodiment--. |
| 7 | 15 | Change "13B" to --FIG. 13B--. |
| 8 | 2 | Change "diptheria" to --diphtheria--. |
| 8 | 10 | Change "perioxidase;" to --peroxidase;--. |
| 8 | 23 | Change "duodenalisa," to --duodenalis,--. |
| 8 | 31 | Change "Trepenoma pallidium," to --Treponema pallidum,--. |
| 8 | 32 | Change "stomatis" to --stomatitis--. |
| 8 | 52 | Change "(barbituates," to --(barbiturates,--. |
| 11 | 5 | Change "capsule" to --capsule.--. |
| 20 | 17 | Change "rioted" to --noted--. |
| 28 | 53 | Change "surface" to --surface.--. |